US009845495B2

(12) United States Patent
Komiya

(10) Patent No.: US 9,845,495 B2
(45) Date of Patent: Dec. 19, 2017

(54) METHOD AND KIT FOR DETECTING TARGET NUCLEIC ACID

(75) Inventor: Ken Komiya, Yokohama (JP)

(73) Assignees: Abbott Laboratories, Abbott Park, IL (US); Tokyo Institute of Technology, Tokyo (JP)

( * ) Notice: Subject to any disclaimer, the term of this patent is extended or adjusted under 35 U.S.C. 154(b) by 239 days.

(21) Appl. No.: 13/992,058

(22) PCT Filed: Dec. 12, 2011

(86) PCT No.: PCT/JP2011/078717
§ 371 (c)(1),
(2), (4) Date: Aug. 26, 2013

(87) PCT Pub. No.: WO2012/077819
PCT Pub. Date: Jun. 14, 2012

(65) Prior Publication Data
US 2014/0017692 A1 Jan. 16, 2014

(30) Foreign Application Priority Data
Dec. 10, 2010 (JP) ................................. 2010-275948

(51) Int. Cl.
*C12Q 1/68* (2006.01)
(52) U.S. Cl.
CPC ........... *C12Q 1/6844* (2013.01); *C12Q 1/682* (2013.01); *C12Q 1/6816* (2013.01)
(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 5,958,700 | A | 9/1999 | Nadeau et al. |
| 2003/0082590 | A1* | 5/2003 | Van Ness ............ C12Q 1/6809 435/6.12 |
| 2003/0165911 | A1 | 9/2003 | Van Ness et al. |
| 2004/0259102 | A1 | 12/2004 | Kool |
| 2005/0059005 | A1 | 3/2005 | Tuschl et al. |
| 2008/0311564 | A1 | 12/2008 | Fort |
| 2009/0017453 | A1 | 1/2009 | Maples et al. |
| 2009/0081670 | A1 | 3/2009 | Maples et al. |
| 2010/0129822 | A1 | 5/2010 | Siva |
| 2015/0197823 | A1 | 7/2015 | Komiya et al. |
| 2016/0102339 | A1 | 4/2016 | Komiya et al. |
| 2016/0102345 | A1 | 4/2016 | Komiya et al. |

FOREIGN PATENT DOCUMENTS

| | | |
|---|---|---|
| CN | 103789435 | 5/2014 |
| EP | 1500710 | 1/2005 |
| JP | H07-114718 B | 5/1995 |
| JP | H07-114718 B | 12/1995 |
| JP | 2005-516610 A | 6/2005 |
| WO | 00/28082 A | 5/2000 |
| WO | 02/16639 A | 2/2002 |
| WO | 03-066802 A3 | 8/2003 |
| WO | 2003-066802 A3 | 8/2003 |
| WO | 2004-067726 A2 | 8/2004 |
| WO | 2004-067764 A2 | 8/2004 |
| WO | 2004-067765 A2 | 8/2004 |
| WO | WO 2004067764 A2 * | 8/2004 ........... C12Q 1/6869 |
| WO | WO 2004067765 A2 * | 8/2004 ........... C12Q 1/6888 |
| WO | 2008/001376 A | 1/2008 |
| WO | 2009-012246 A2 | 1/2009 |
| WO | 2012/077819 | 6/2012 |
| WO | 2015114469 | 8/2015 |
| WO | 2016059473 | 4/2016 |
| WO | 2016059474 | 4/2016 |

OTHER PUBLICATIONS

Lai et al. (Calibration curves for real-time PCR, Clin Chem. Jul. 2005;51(7):1132-6).*
Van Ness et al. (Isothermal reactions for the amplification of oligonucleotides, PNAS, Apr. 15, 2003, vol. 100, No. 8, 4504-4509).*
G.T.Walker,M.C.Little,J.G.Nadeau and D. D.Shank,Proc.Natl. Acad.Sci.USA,89,392-396(1992).
Y.Weizmann,M.K.Beissenhirtz, Z.Cheglakov,R.Nowarski and I.Willner, Angew. Chem.Int.Ed.,45,7384-7388(2006).
International Preliminary Report, PCT/JP2011/078717, International Filing Date Dec. 12, 2011 (Tokyo Institute of Technology).
J. Van Ness, L.K. Ness, and D.J. Galas, Proc. Natl. Acad. Sci. USA, 100 (8):4504-4509 (Apr. 15, 2003).
Dirks, Robert M., Pierce, Niles A., PNAS, Oct. 26, 2004, vol. 101, No. 43, 15275-15278.
Huang, Jin, Wu, Yanrong, Chen, Yan, Zhu, Zhi, Yang, Xiaohai, Yang, Chaoyong James, Wang, Kemin, Tan, Weihong, Angew. Chem.Int.Ed. 2011, 50, 401-404.
Niu, Shuyan, Jiang, Yu, Zhang, Susheng, Chem. Commun., 2010, 46, 3089-3091 (2010).
International Search Report, PCT/JP2011/078717, International Filing Date Dec. 12, 2011 (Tokyo Institute of Technology).

(Continued)

Primary Examiner — Aaron Priest
(74) Attorney, Agent, or Firm — McAndrews, Held & Malloy, Ltd; Audrey L. Bartnicki

(57) ABSTRACT

[Problem] To provide a method for detecting a nucleic acid (such as DNA and RNA) under isothermal conditions, in particular a method by which a short-chain nucleic acid can be directly detected. [Solution] A method for detecting a target nucleic acid in a sample of the present invention comprises: (a) a step of preparing a first oligonucleotide which comprises, in the direction from 5' to 3', a first arbitrary sequence, an endonuclease recognition site that is used in a nicking reaction, and a sequence complementary to the target nucleic acid; (b) a step of carrying out a nucleic acid amplification reaction using the target nucleic acid contained in the sample as a primer in the presence of an endonuclease which recognizes the endonuclease recognition site that is used in a nicking reaction; and (c) a step of detecting an oligonucleotide which is obtained by the nucleic acid amplification reaction and comprises a sequence complementary to the first arbitrary sequence.

18 Claims, 39 Drawing Sheets

(56) References Cited

OTHER PUBLICATIONS

Tan, E. et al., "Isothermal DNA Amplification with Gold Nanosphere-Based Visual Colorimetric Readout for Herpes Simplex Virus Detection", Clinical Chemistry, 53, No. 11, pp. 2017-2020 (2007).
Tan, E. et al., "Isothermal DNA Amplification Coupled with DNA Nanosphere-Based Colorimetric Detection", Analytical Chemistry, vol. 77, No. 24, pp. 7984-7992 (Dec. 15, 2005).
Tan, E. et al., "Specific versus Nonspecific Isothermal DNA Amplification through Thermophilic Polymerase and Nicking Enzyme Activities", Biochemistry, vol. 47, No. 38, pp. 9987-9999 (2008).
International Search Report and Written Opinion of PCT Patent Application No. PCT/IB2015/000726, mailed Sep. 10, 2015, 12 pages.
Gill, et al. "Nucleic Acid Isothermal Amplification Technologies—A Review", Nucleosides, Nucleotides and Nucleic Acids, Taylor & Francis, US, vol. 27, No. 3, Mar. 1, 2008, pp. 224-243.
PCT International Search Report and Written Opinion dated Mar. 29, 2016 for PCT Patent Application No. PCT/IB2015/002145, 6 pages.
Veedu et al.,, "Locked Nucleic Acids: Promising Nucleic Acid Analogs for Therapeutic Applications," Chemistry & Biodiversity, vol. 7, 2010, 7 pages.
Yang et al., "Synthesis and investigation of deoxyribonucleic acid/locked nucleic acid chimeric molecular beacons," Nucleic Acids Research, vol. 35, 2007, 9 pages.
Vester et al., "LNA (Locked Nucleic Acid): High-Affinity Targeting of Complementary RNA and DNA," Biochemistry, vol. 43, 2004, 12 pages.
PCT, Notification of Transmittal of the International Search Report and the Written Opinion of the International Searching Authority, or the Declaration, in International Application No. PCT/IB2015/059986, dated Jun. 3, 2016 (16 pages).
Haiyun Liu et al., "High Specific and Ultrasensitive Isothermal Detection of MicroRNA by Paddlock Prob-Based Exponential Rolling Circle Amplification", Analytical Chemistry, vol. 85, No. 16, Aug. 20, 2013 (Aug. 20, 2013), pp. 7941-7947, XP055272748, ISSN: 0003-2700, DOI:10.1021/ac401715k abstract (7 pages).
Bin-Cheng Yin et al., "Sensitive Detection of MicroRNA in Complex Biological Samples via Enzymatic Signal Amplification Using DNA Polymerase Coupled with Nicking Endonuclease" Analytical Chemistry, vol. 85, No. 23, Dec. 3, 2013 (Dec. 3, 2013), pp. 11487-11493, XP055272740, ISSN: 0003-2700, DOI: 10.1021/ac403302a abstract (7 pages).
International Search Report and Written Opinion of PCT Patent Application No. PCT/IB2015/002141, mailed Apr. 6, 2016, 8 pages.
International Bureau, "International Preliminary Report on Patentability", issued in connection with Application No. PCT/IB2015/002141, Apr. 18, 2017, 6 pages.
International Bureau, "International Preliminary Report on Patentability", issued in connection with Application No. PCT/IB2015/002145, Apr. 18, 2017, 10 pages.

* cited by examiner

[Figure 1]
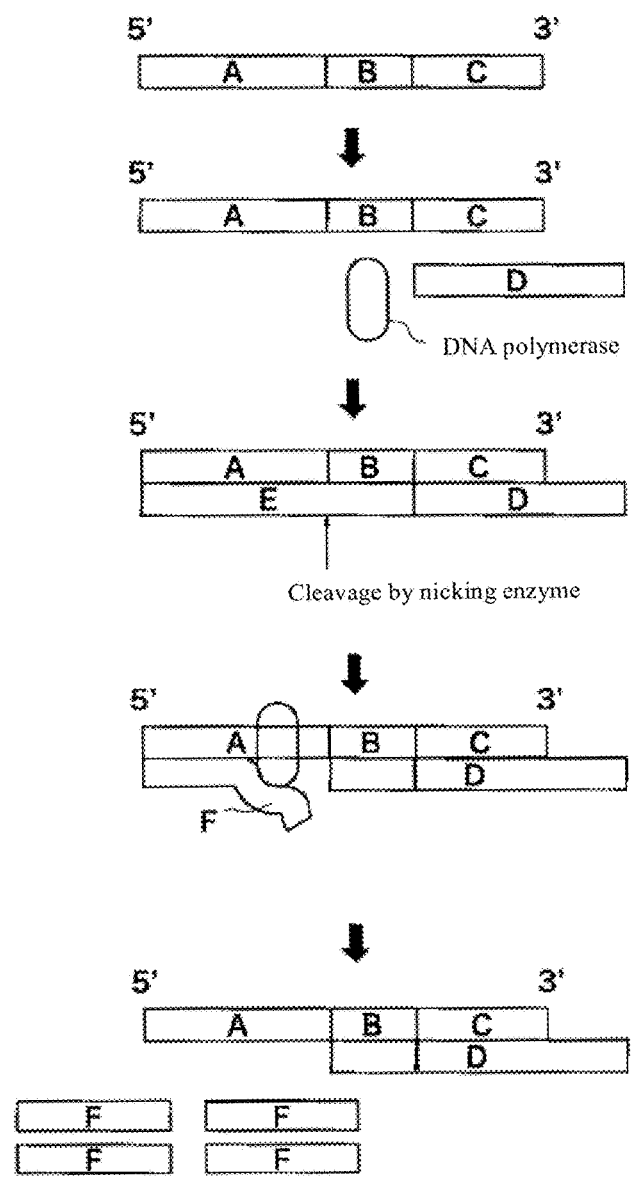

[Figure 2]
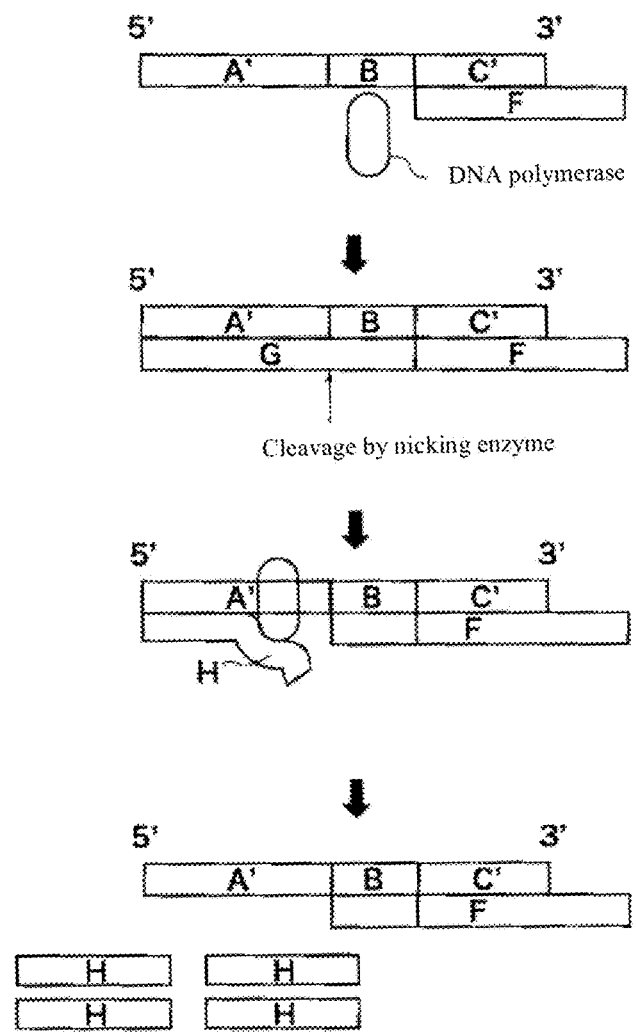

[Figure 3]
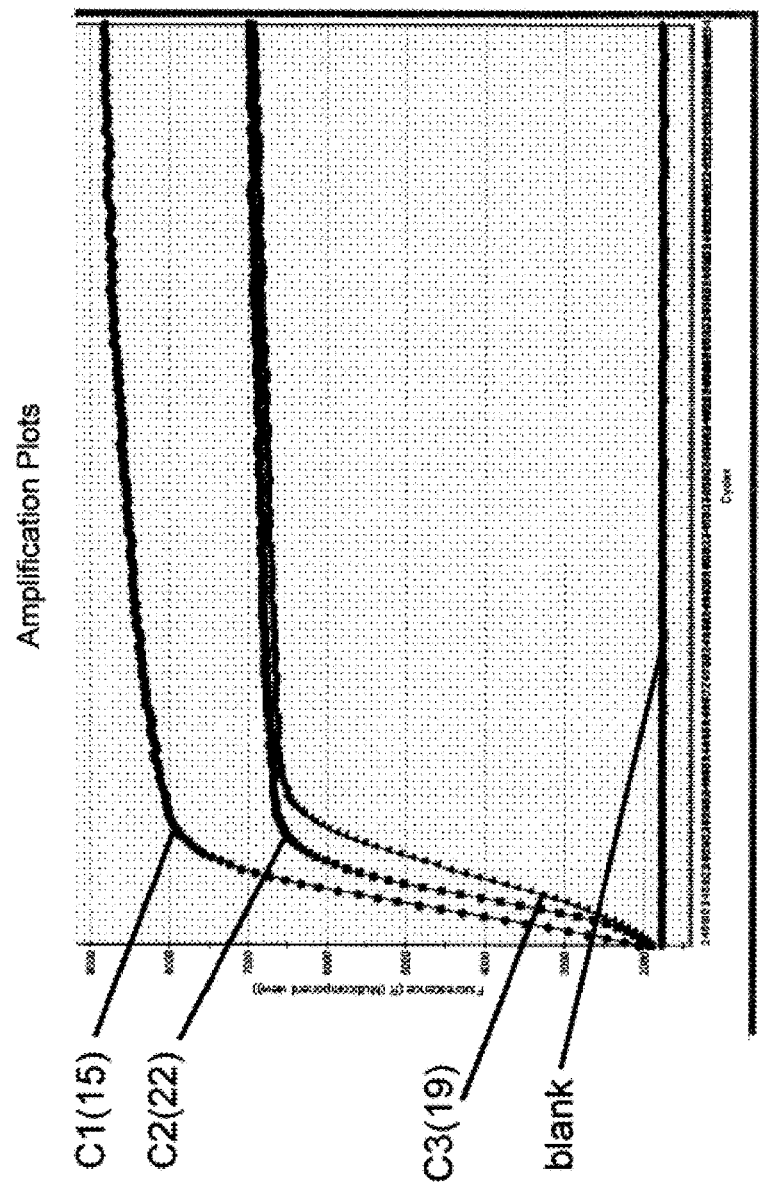

[Figure 4]
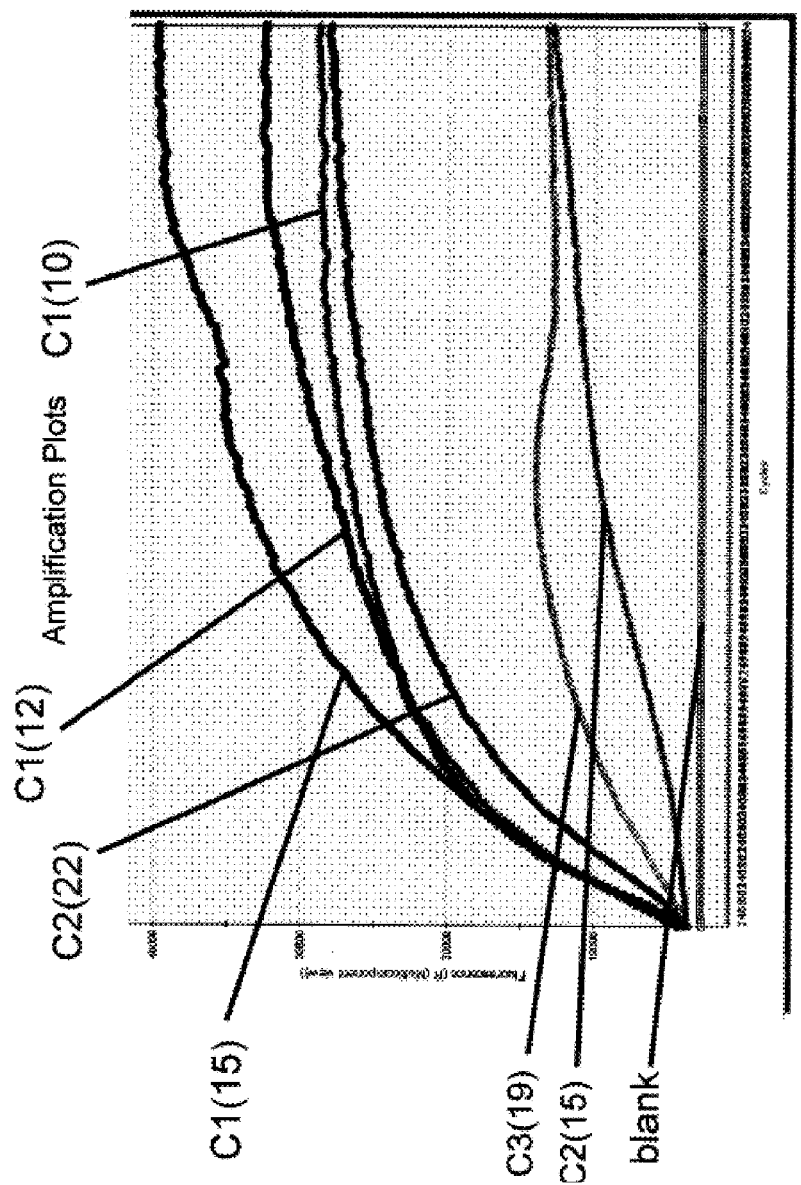

[Figure 5]
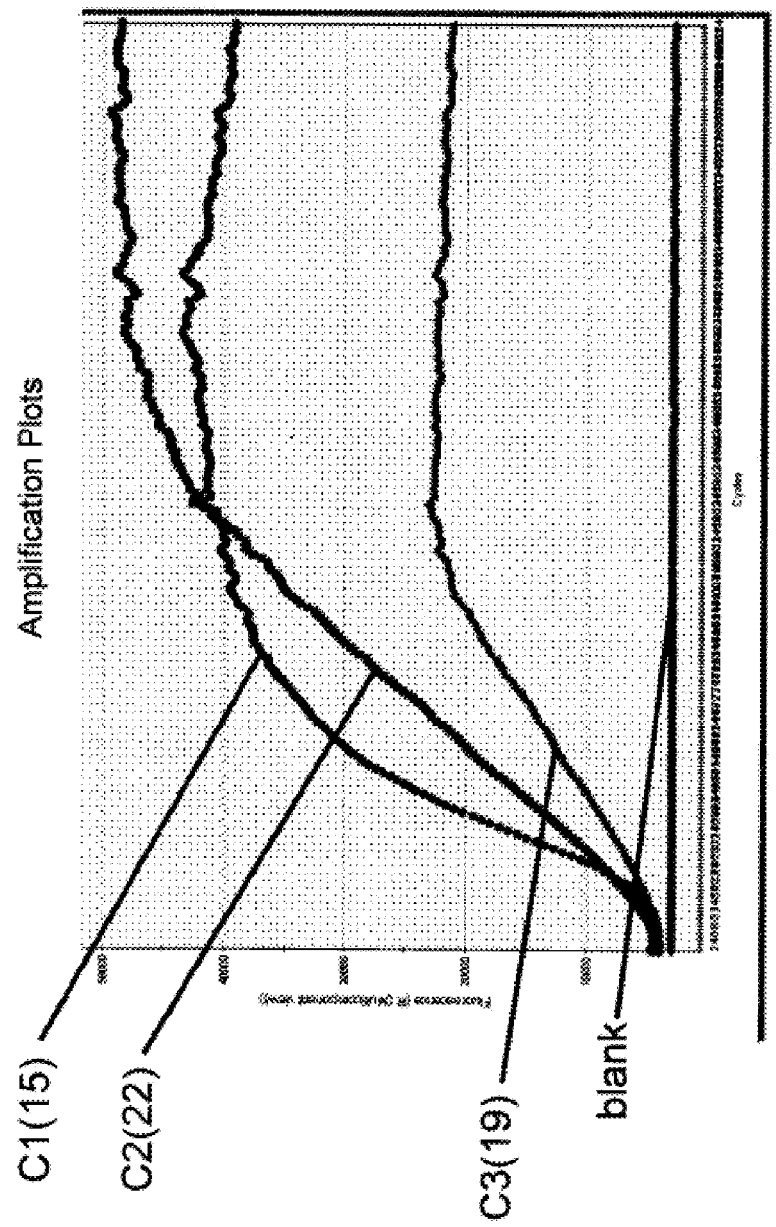

[Figure 6]
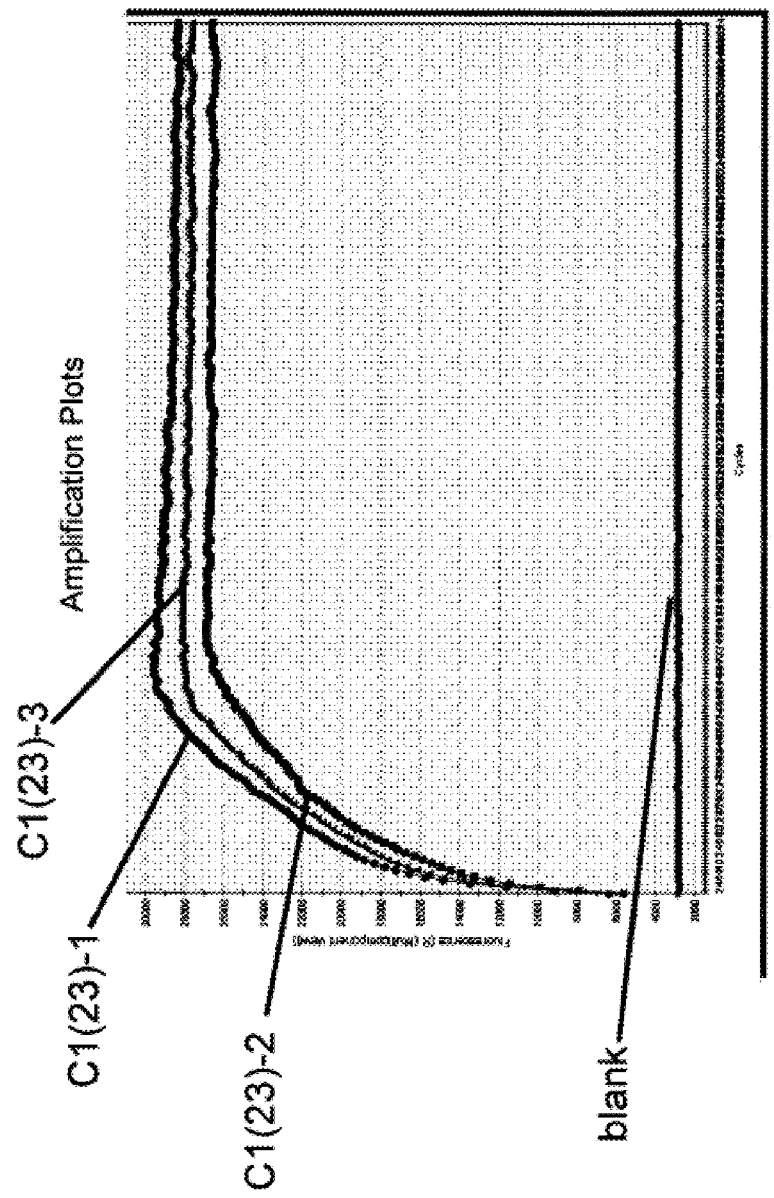

[Figure 7]
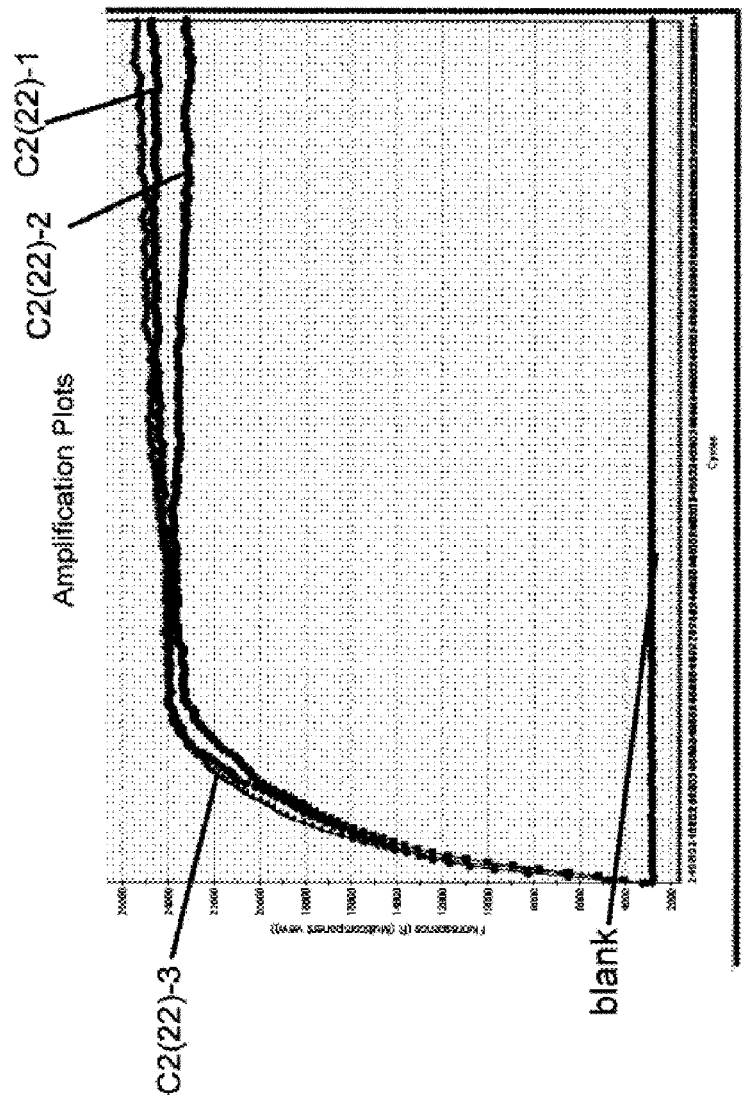

[Figure 8]
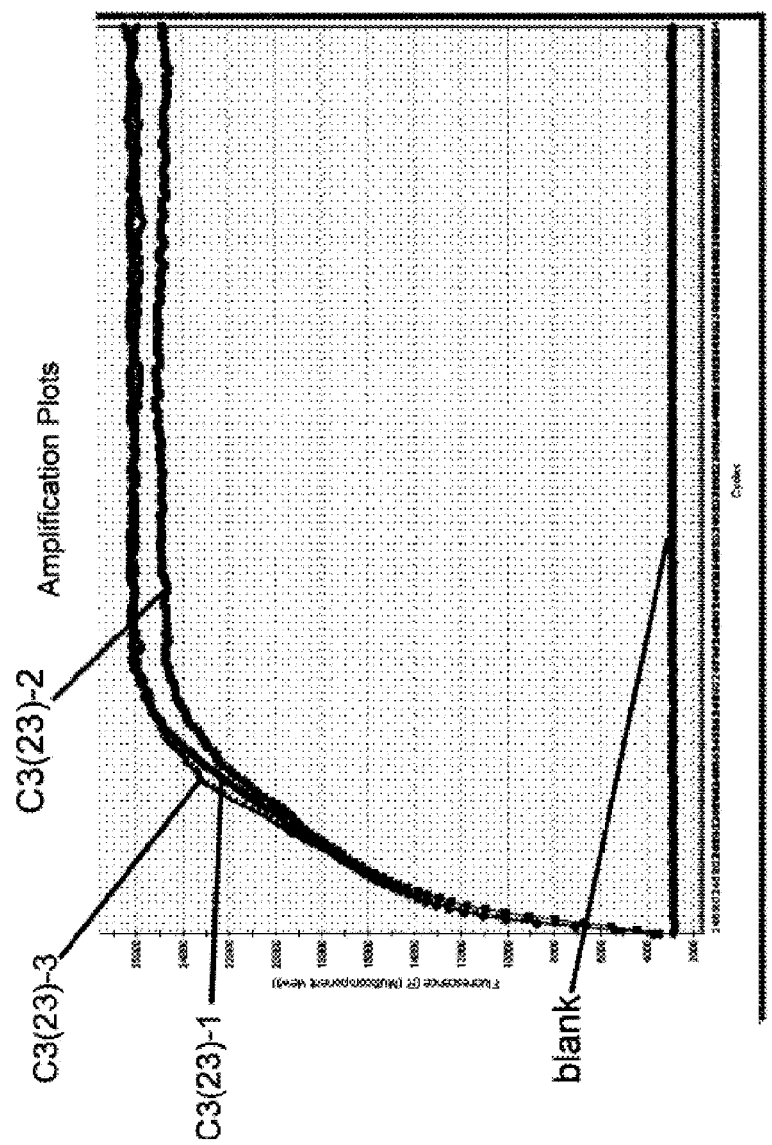

[Figure 9]
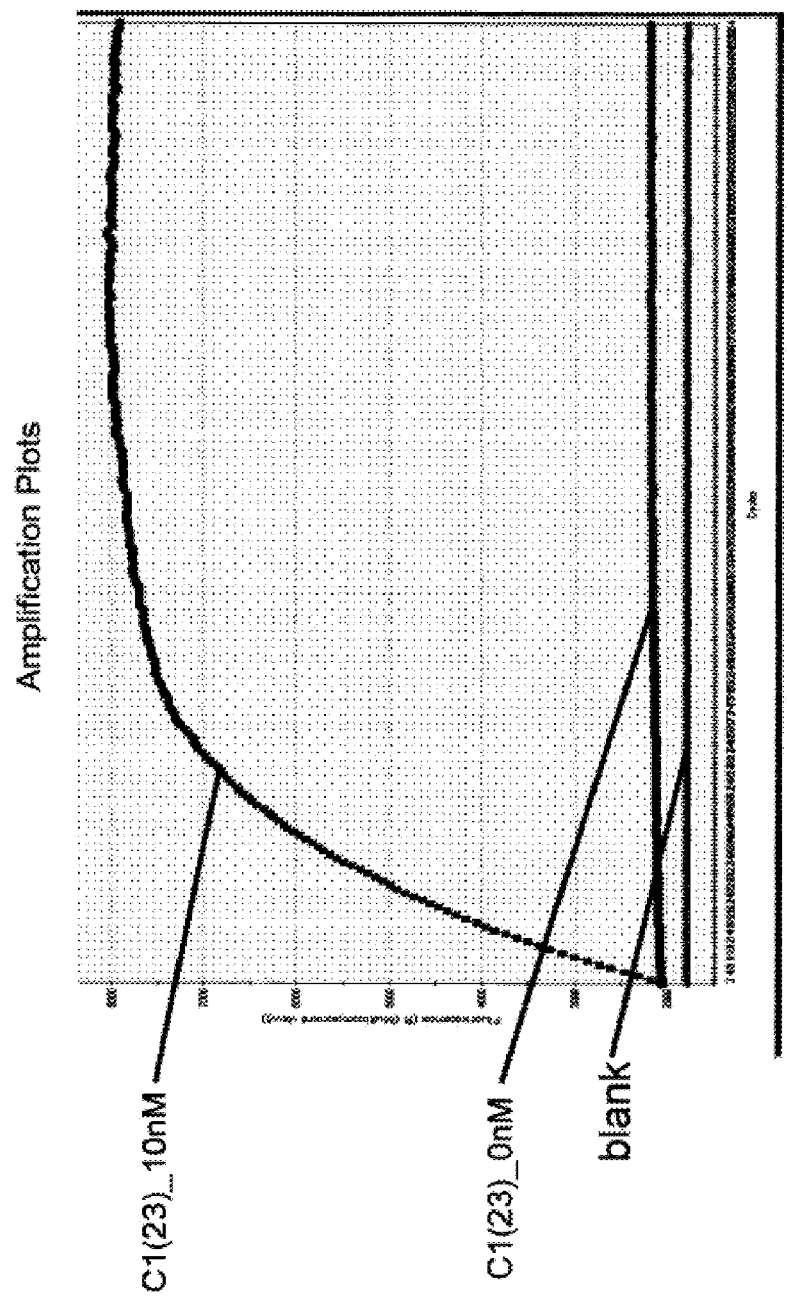

[Figure 10]
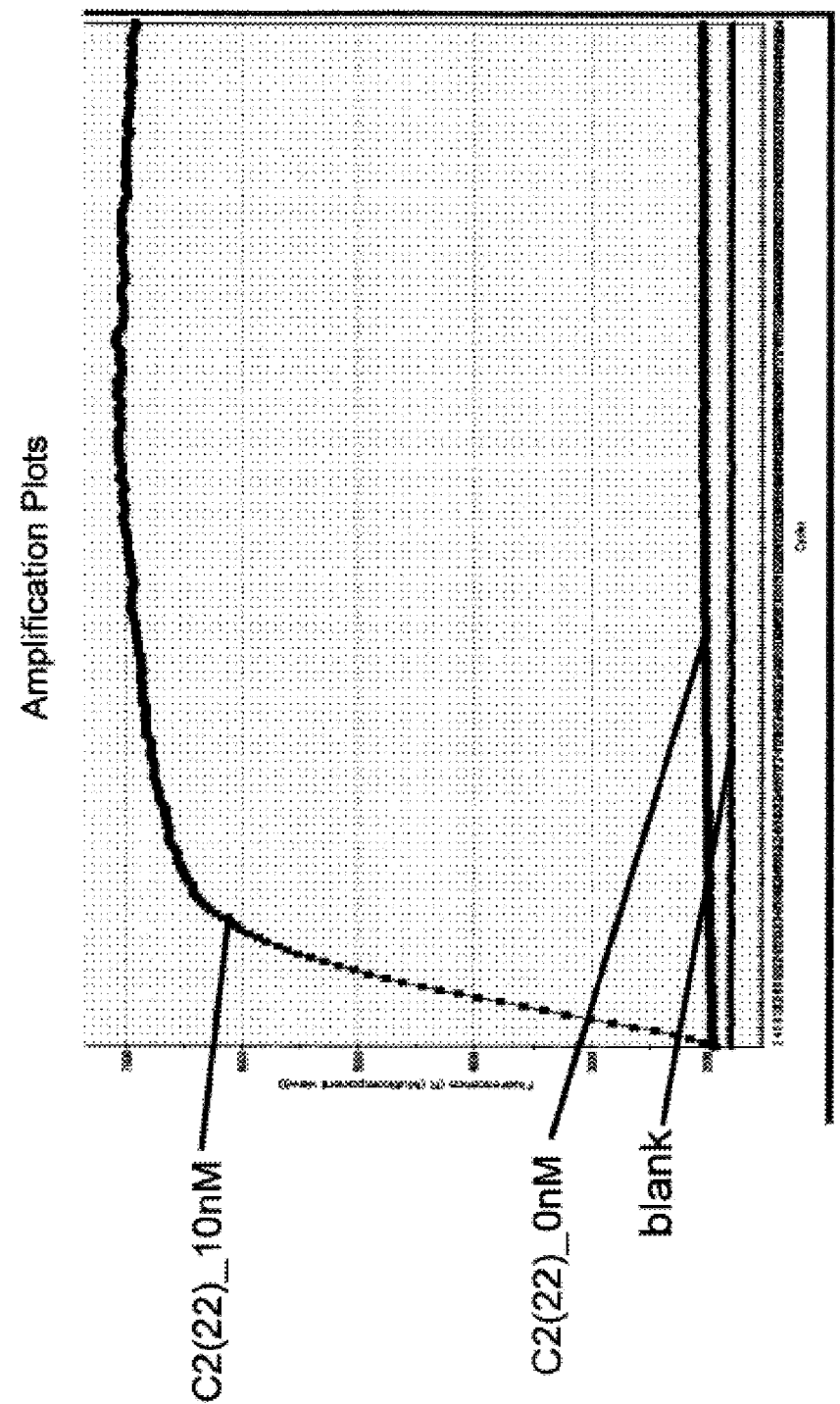

[Figure 11]
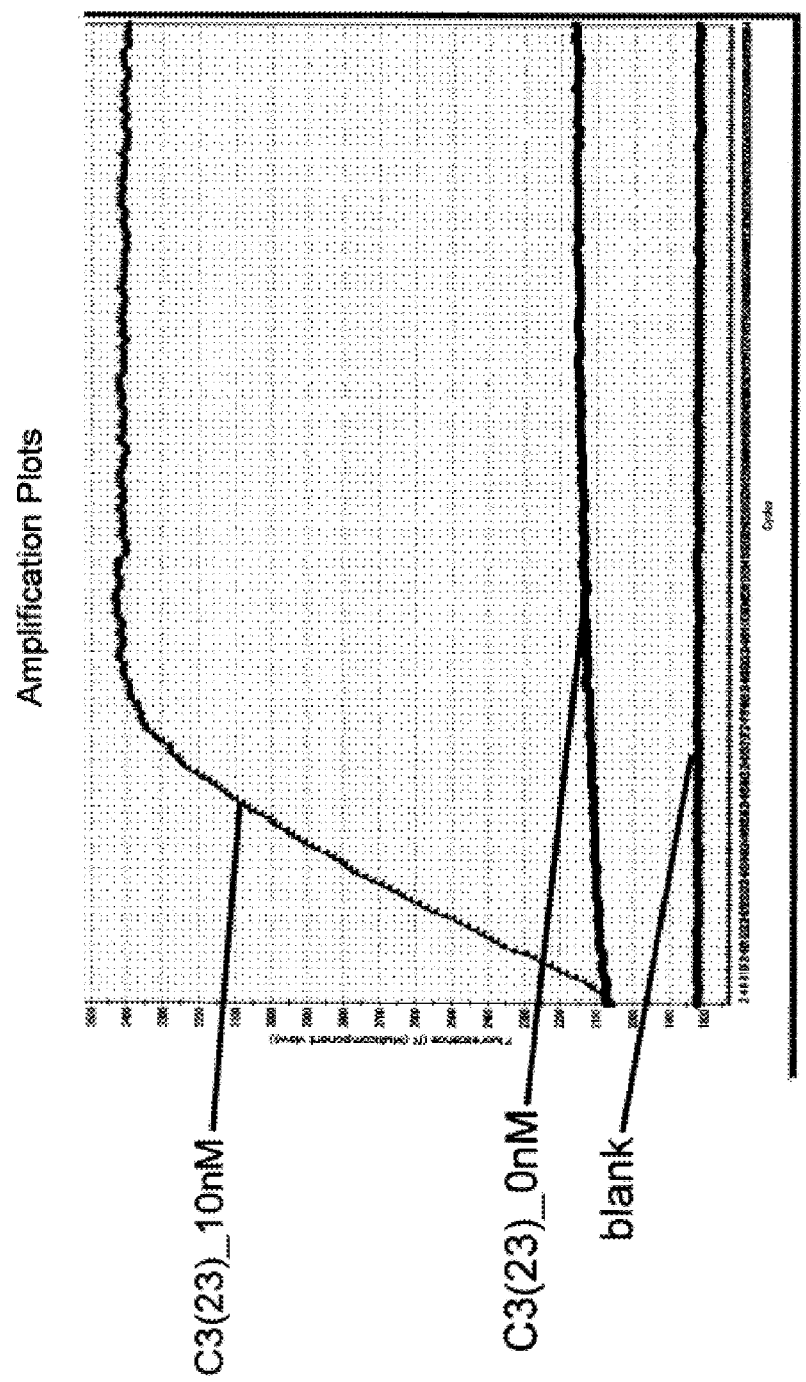

[Figure 12]
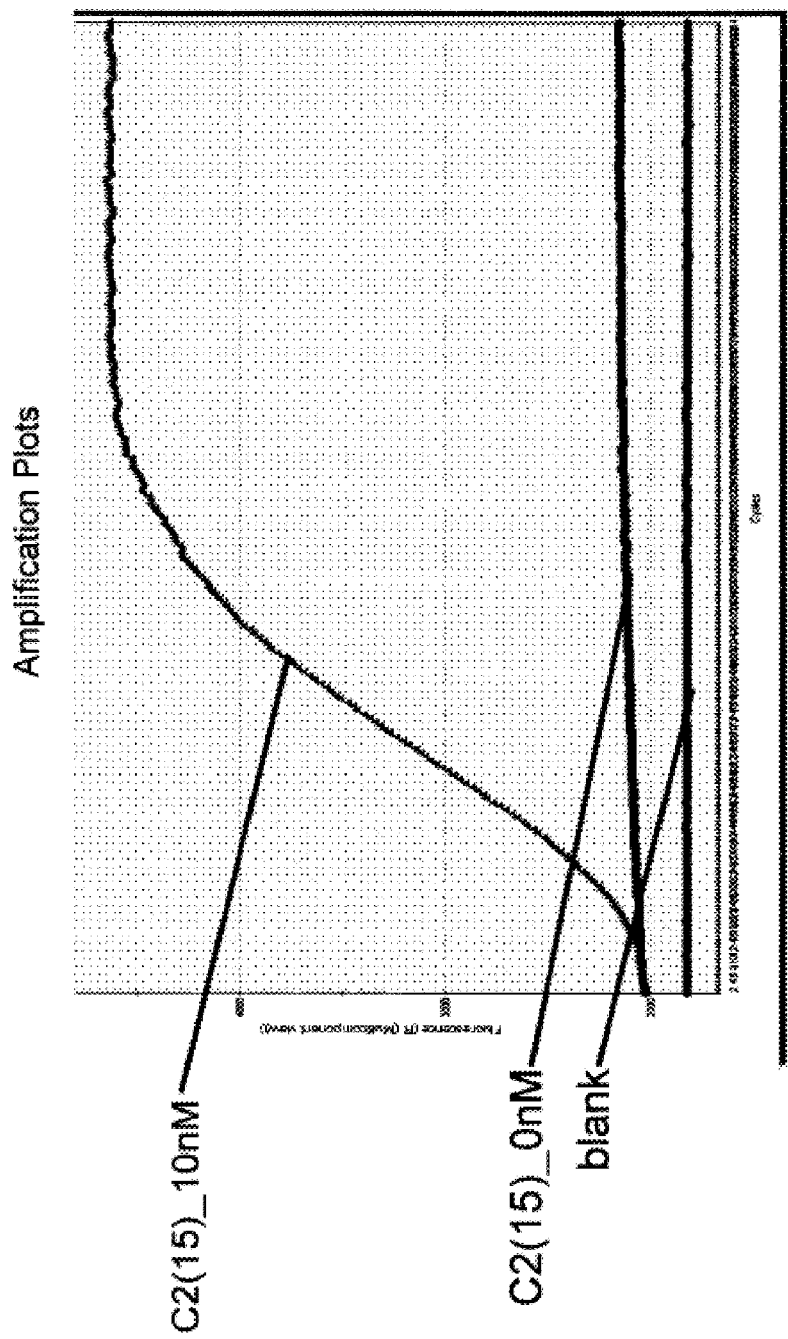

[Figure 13]
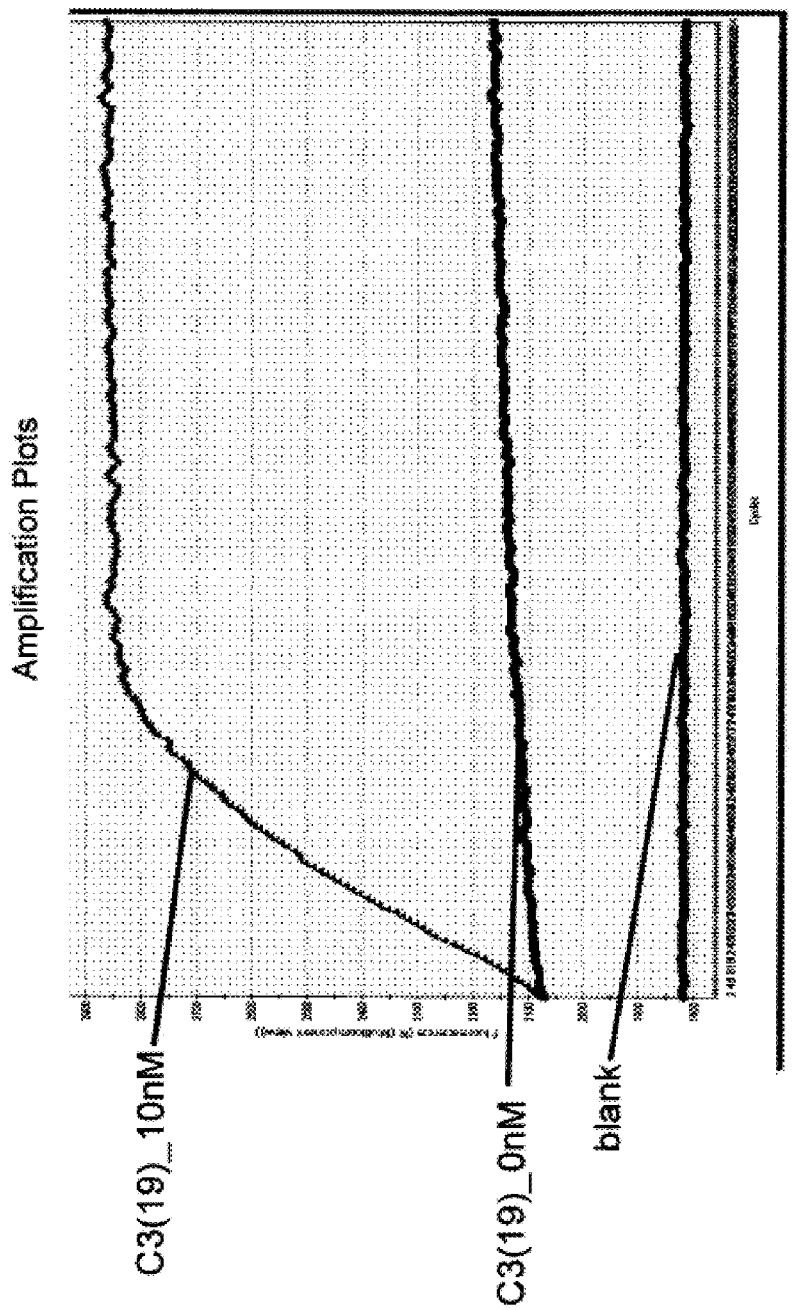

[Figure 14]
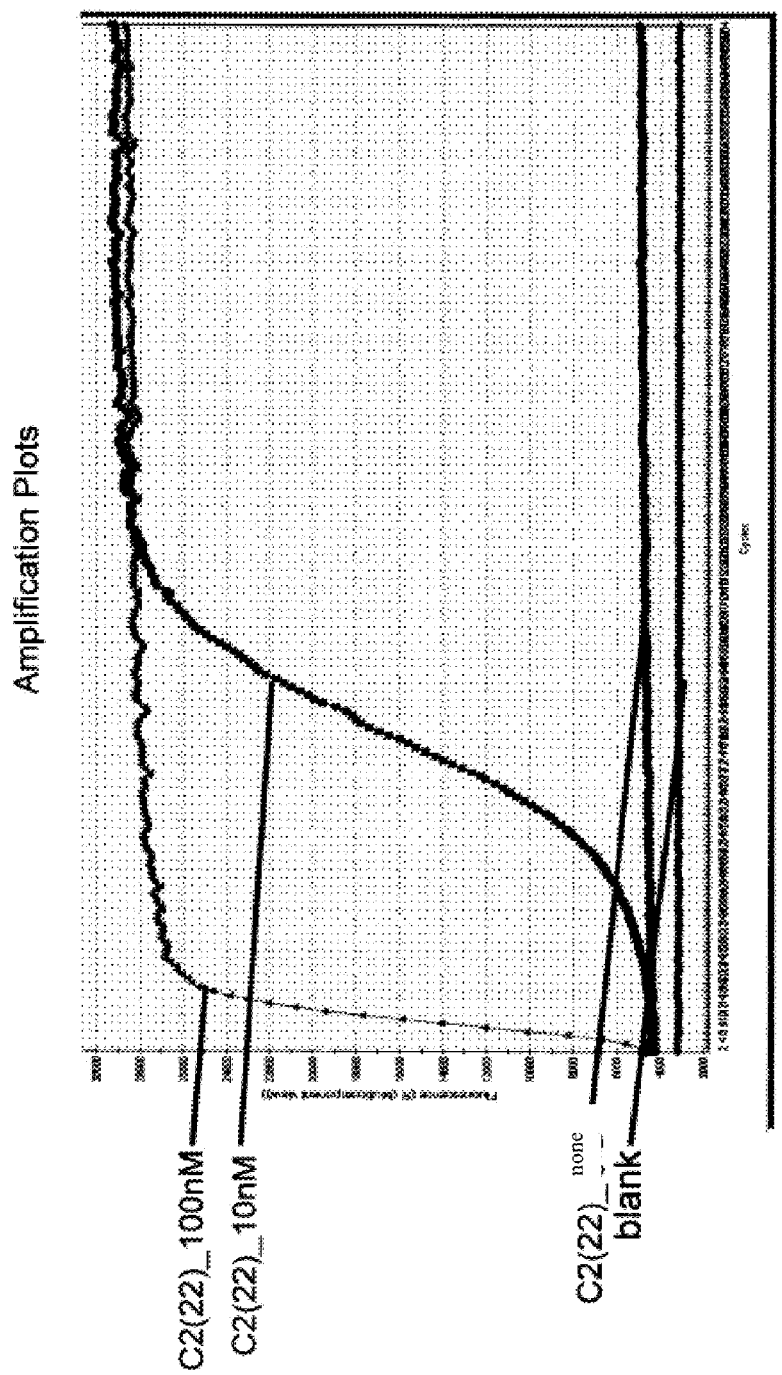

[Figure 15]
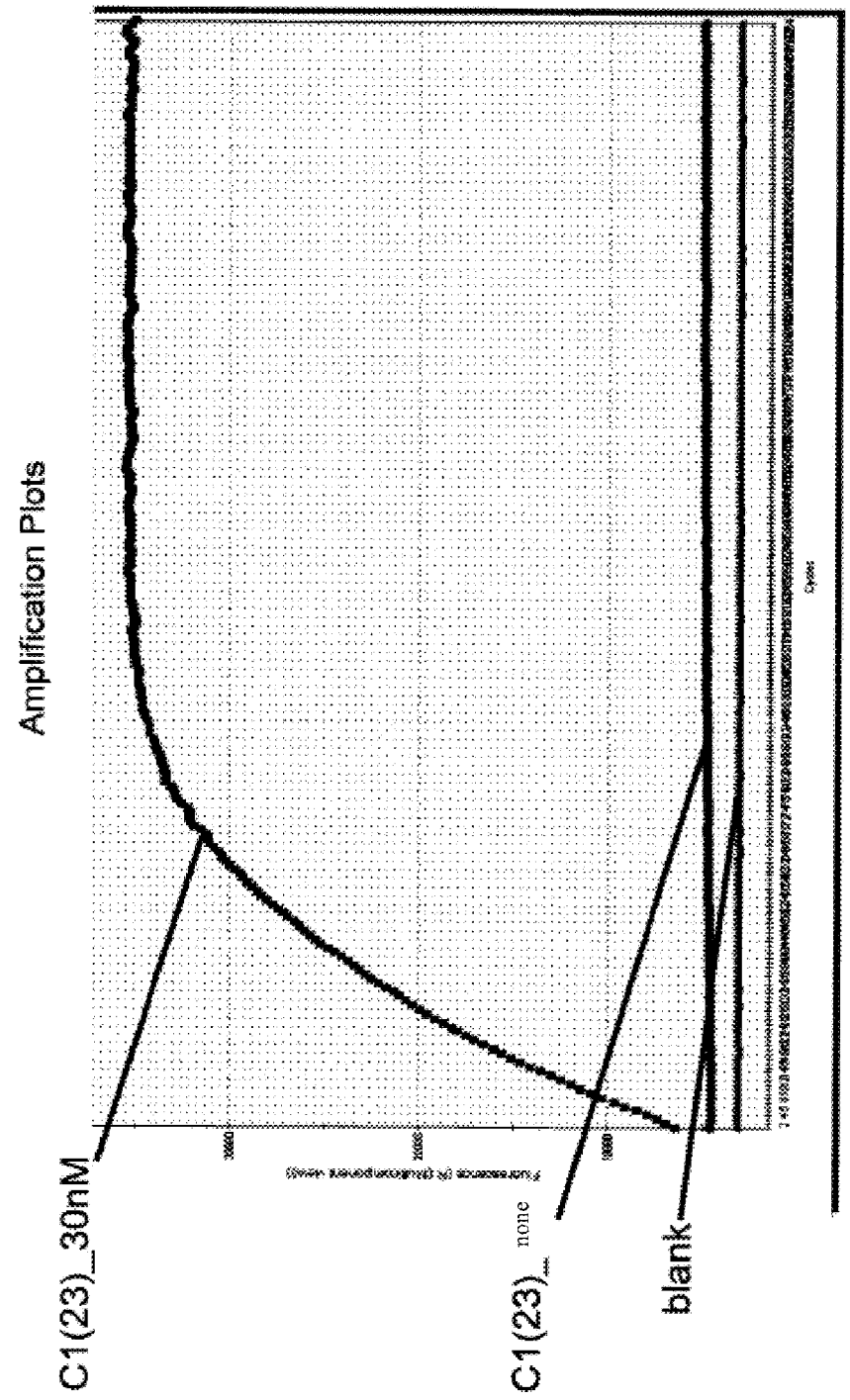

[Figure 16]
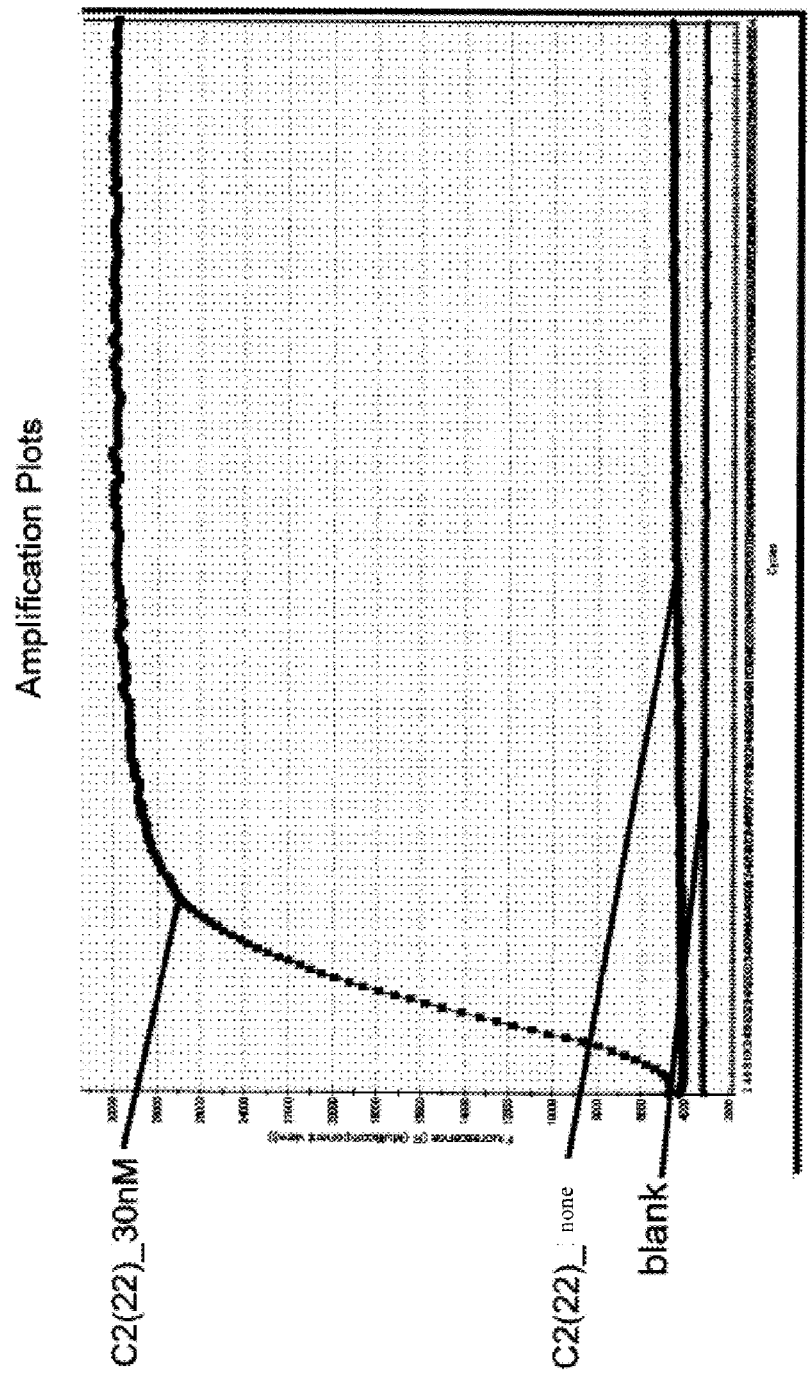

[Figure 17]
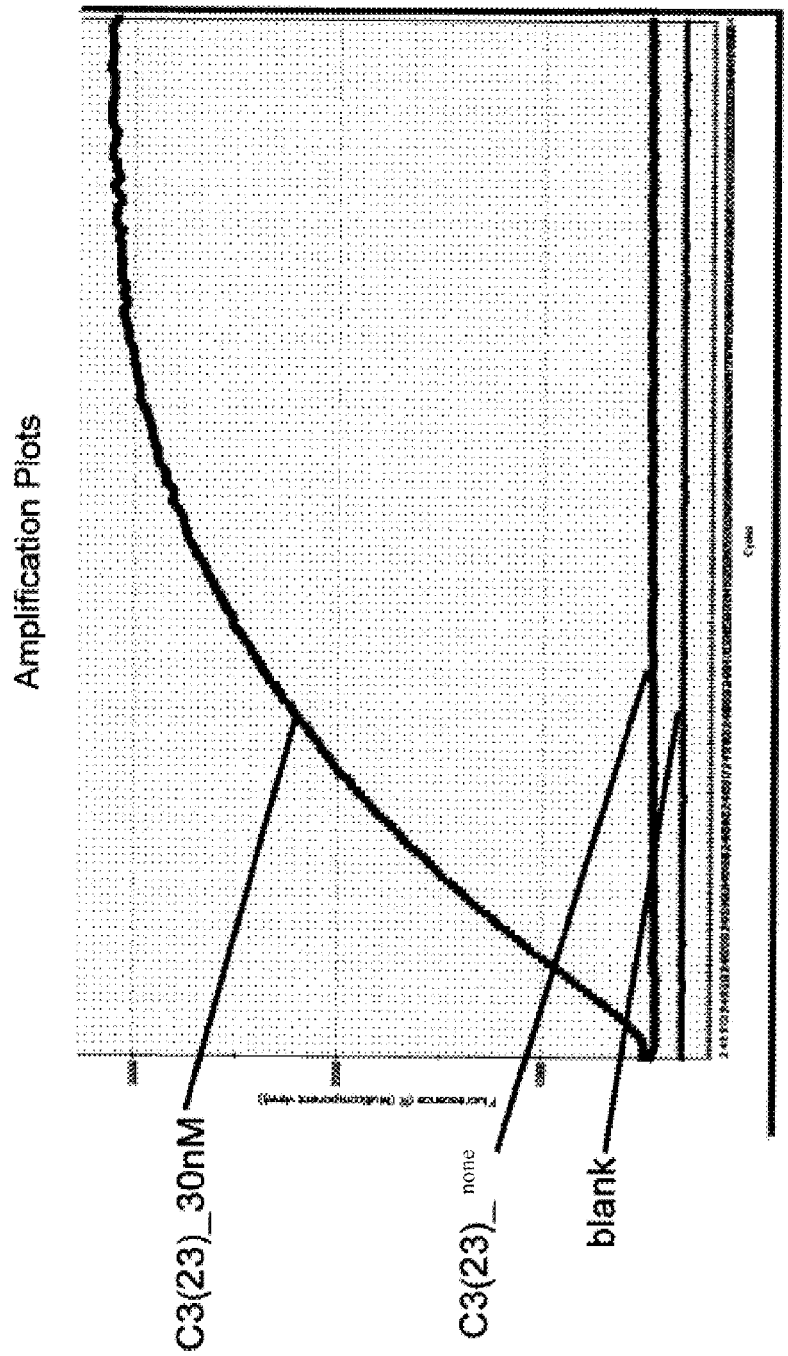

[Figure 18]
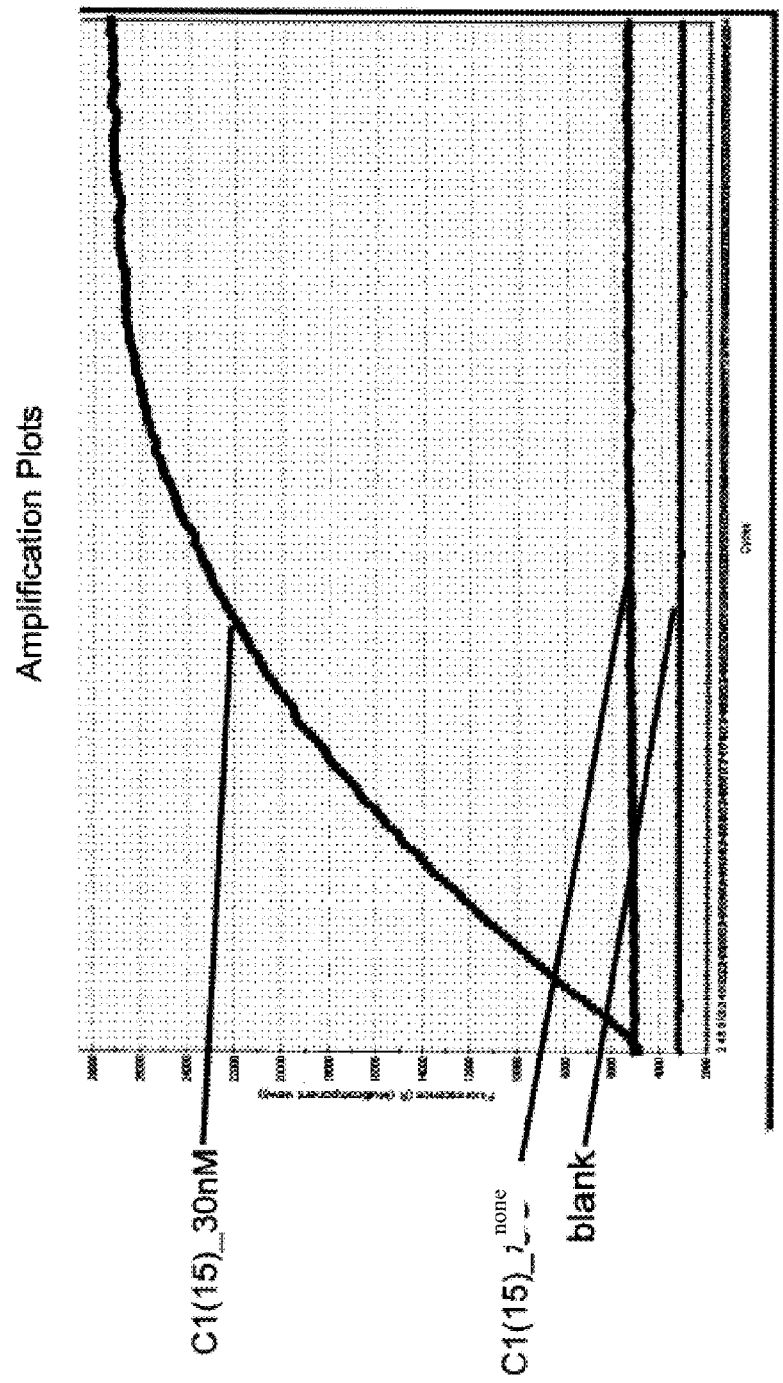

[Figure 19]
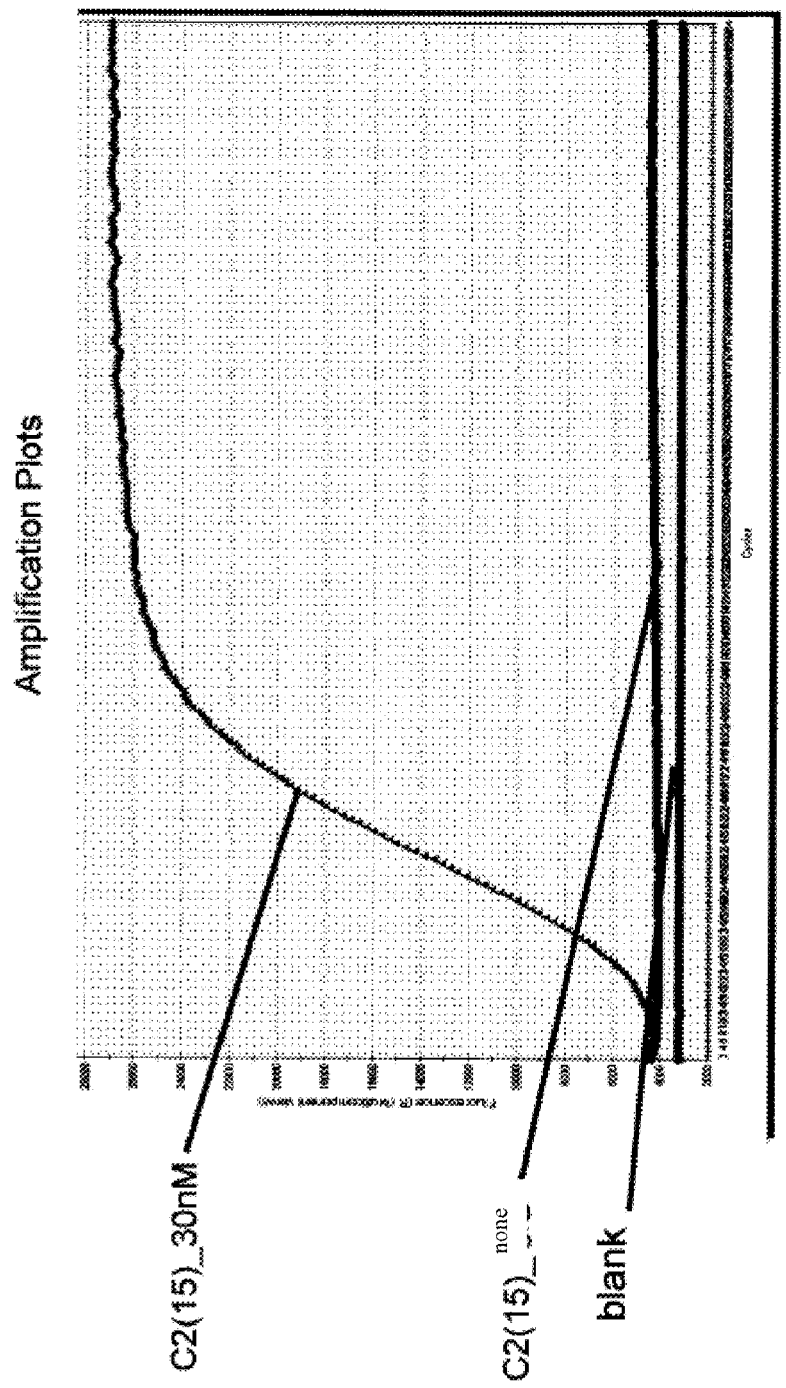

[Figure 20]
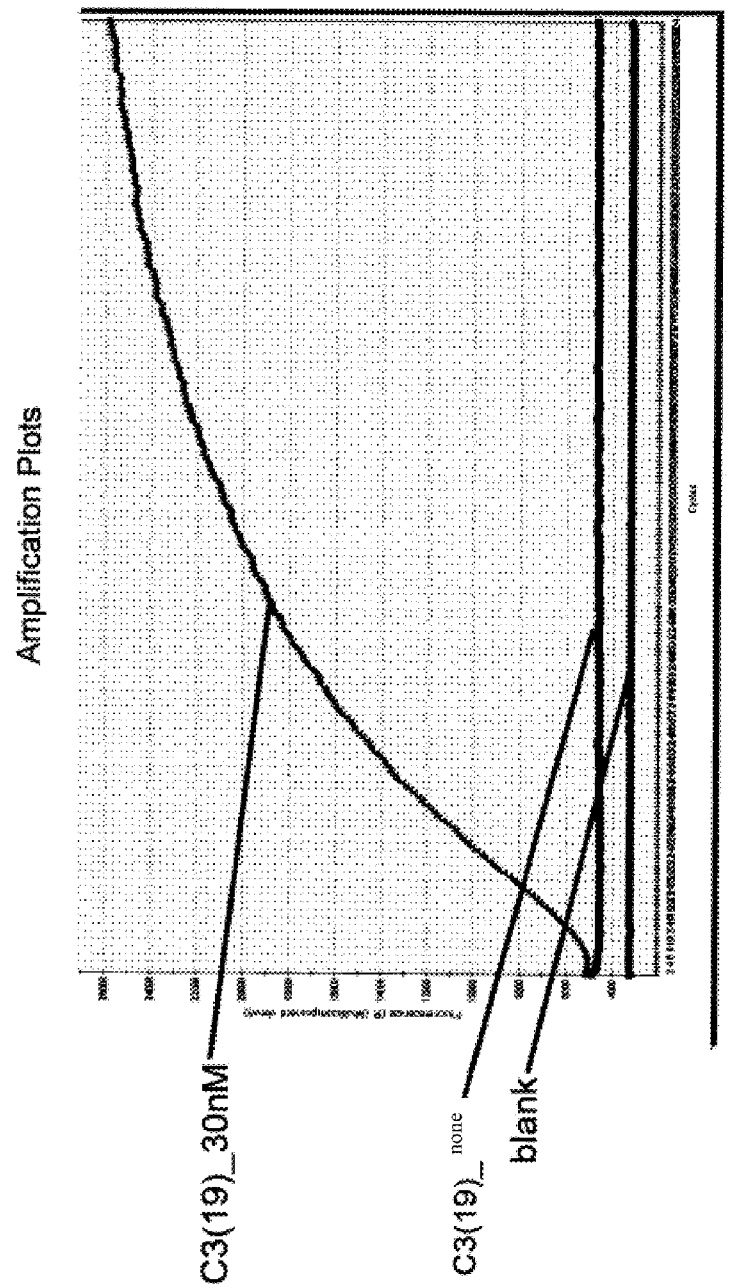

[Figure 21]
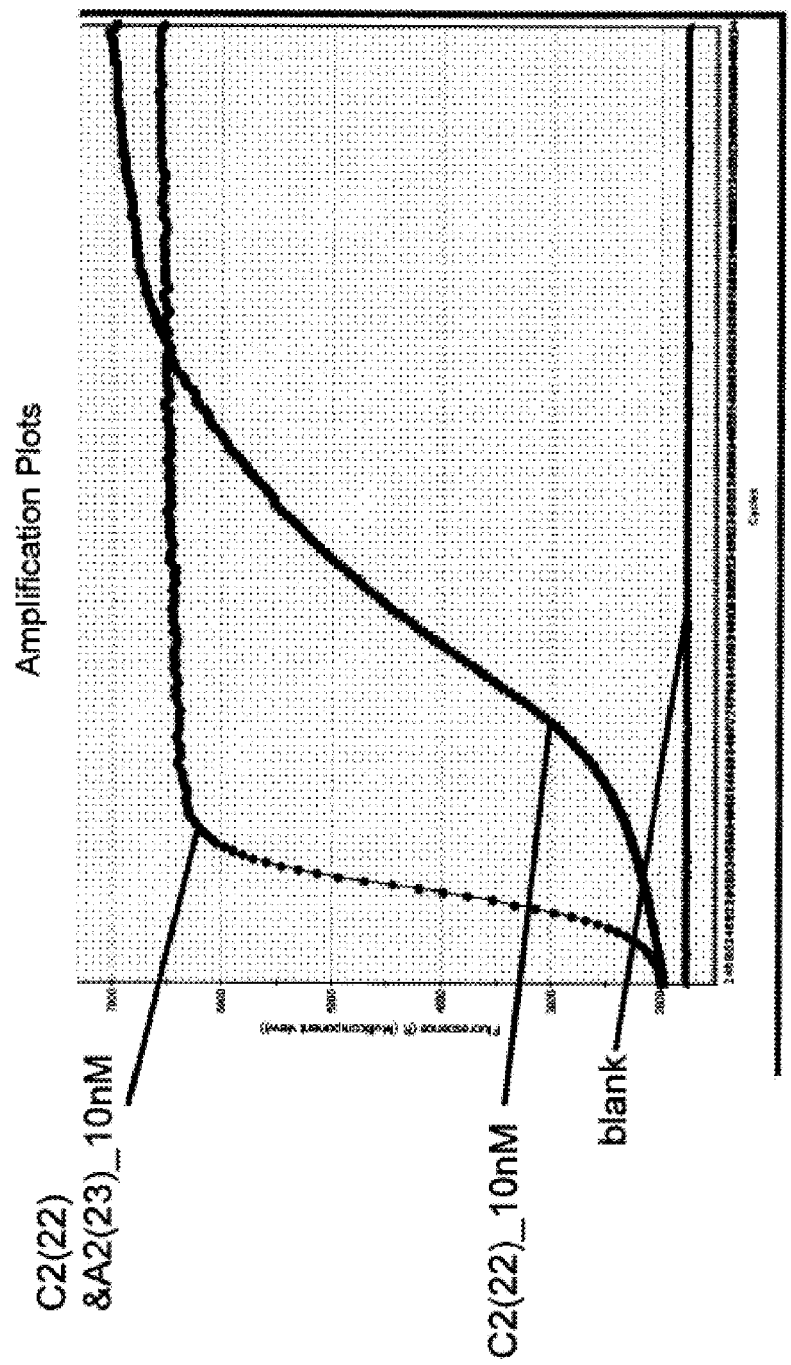

[Figure 22]
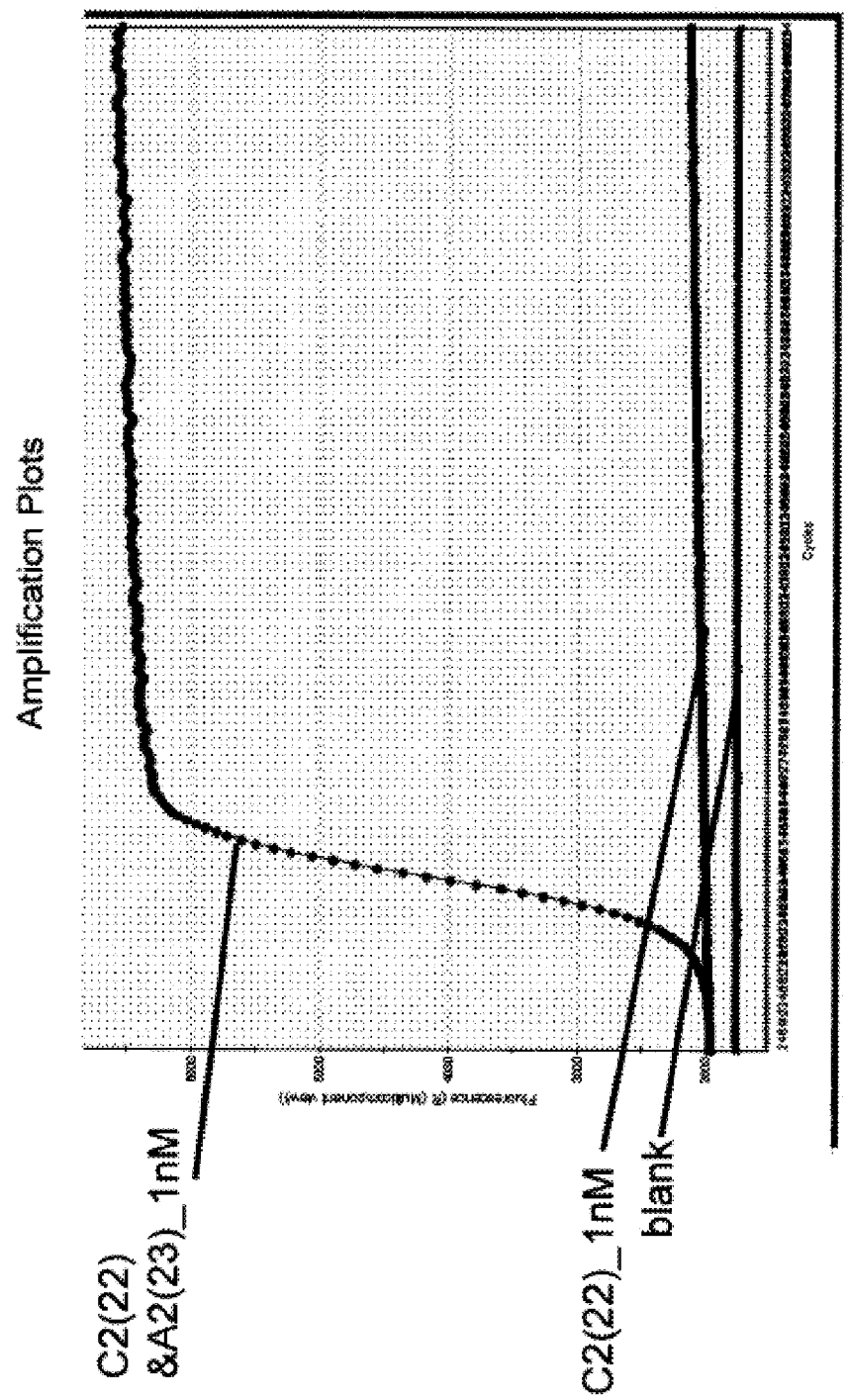

[Figure 23]
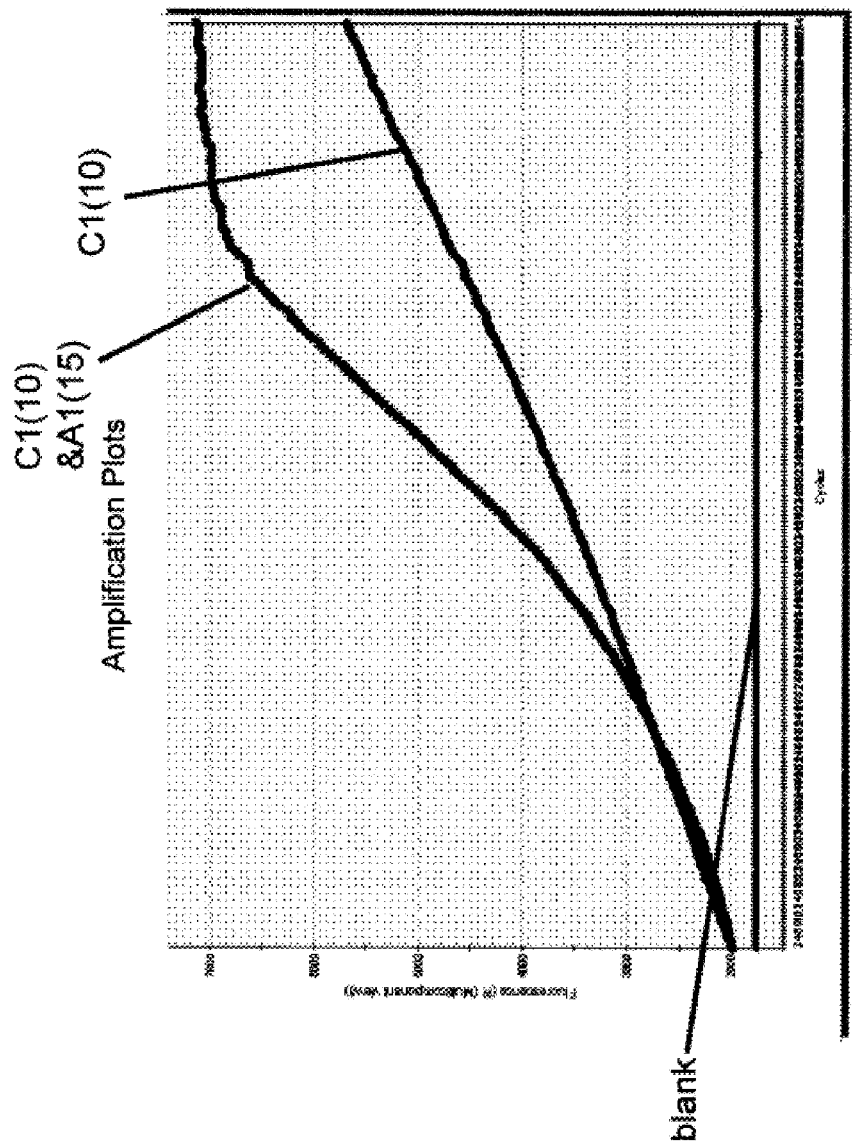

[Figure 24]
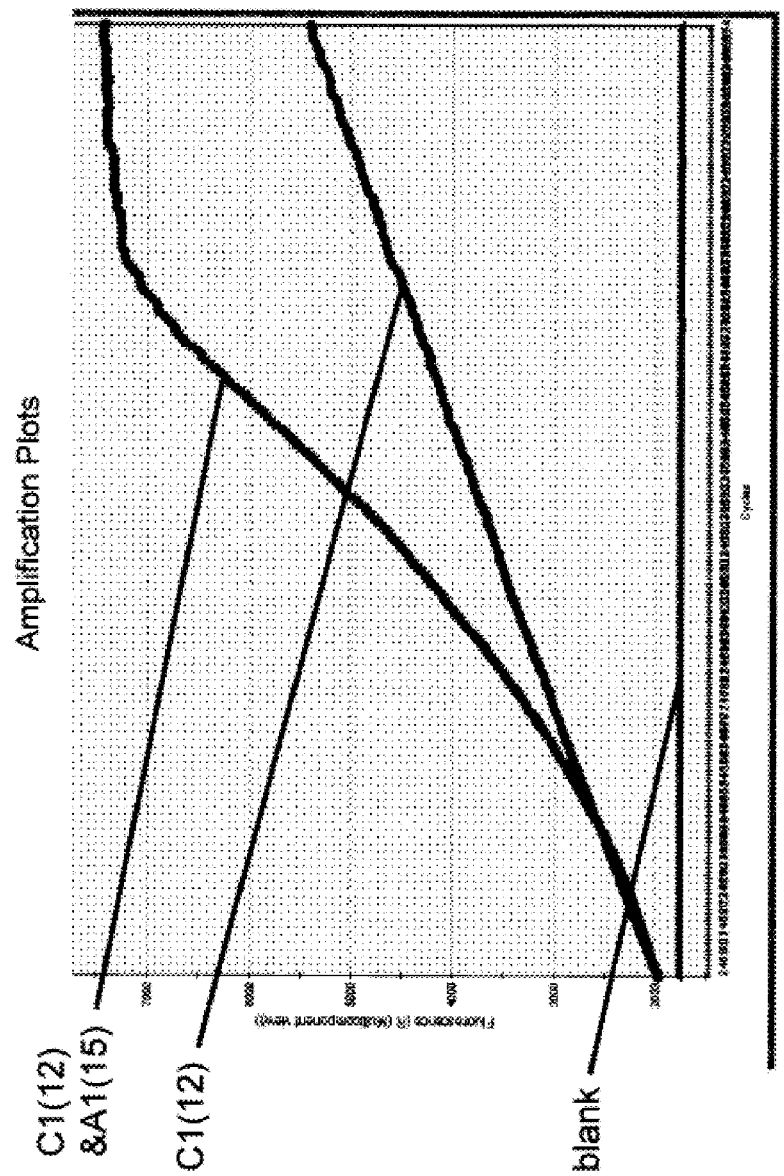

[Figure 25]

[Figure 26]
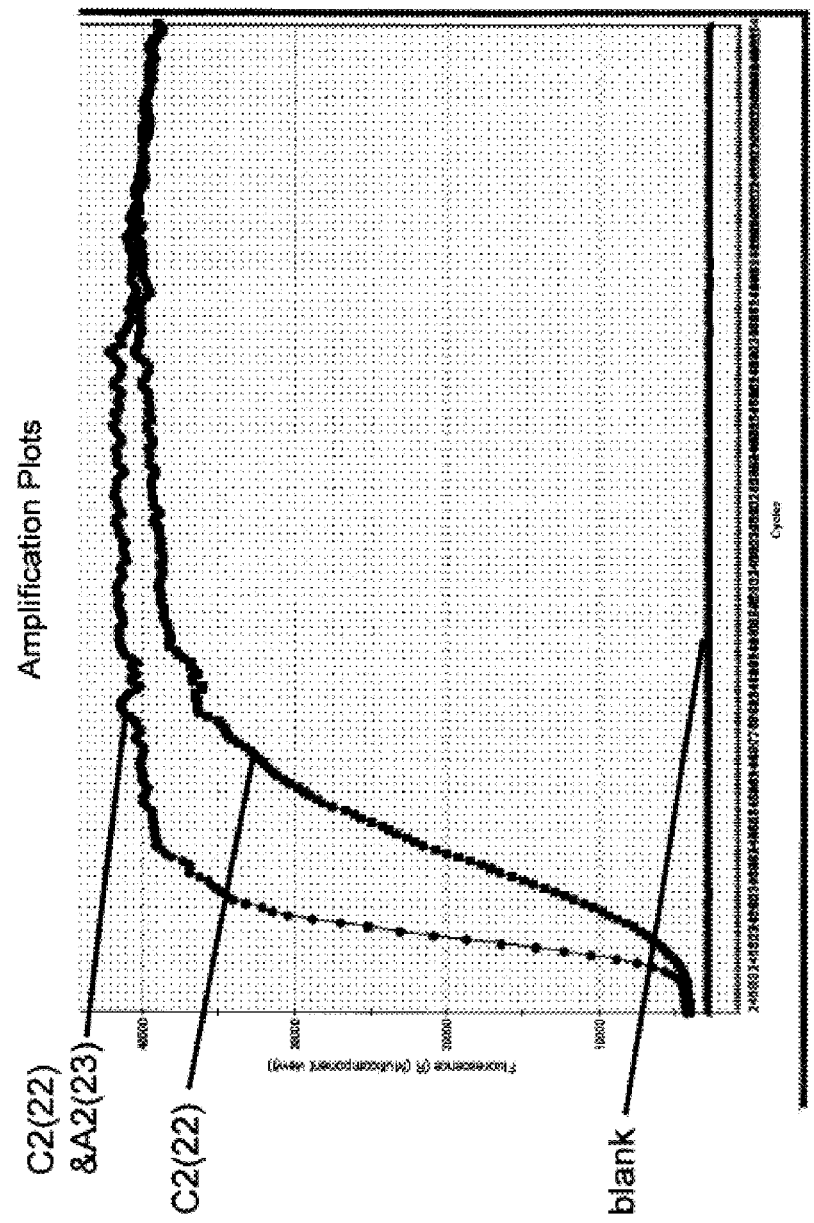

[Figure 27]
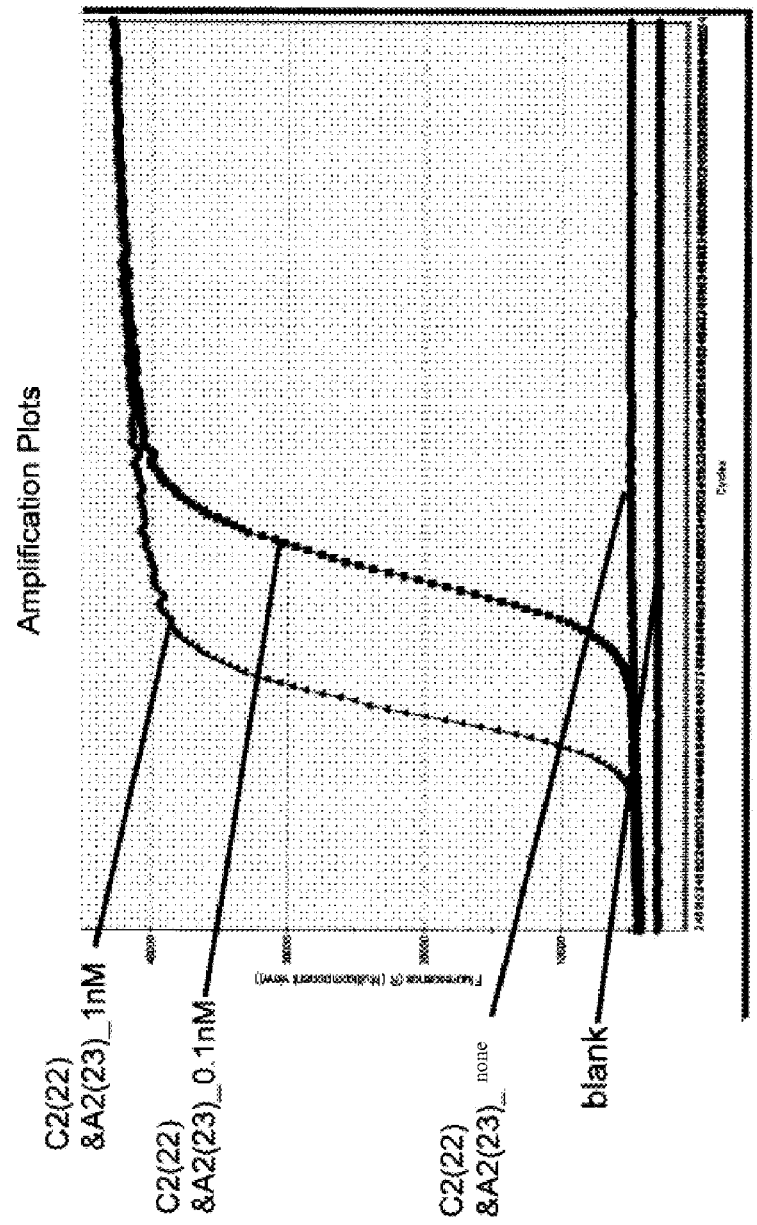

[Figure 28]
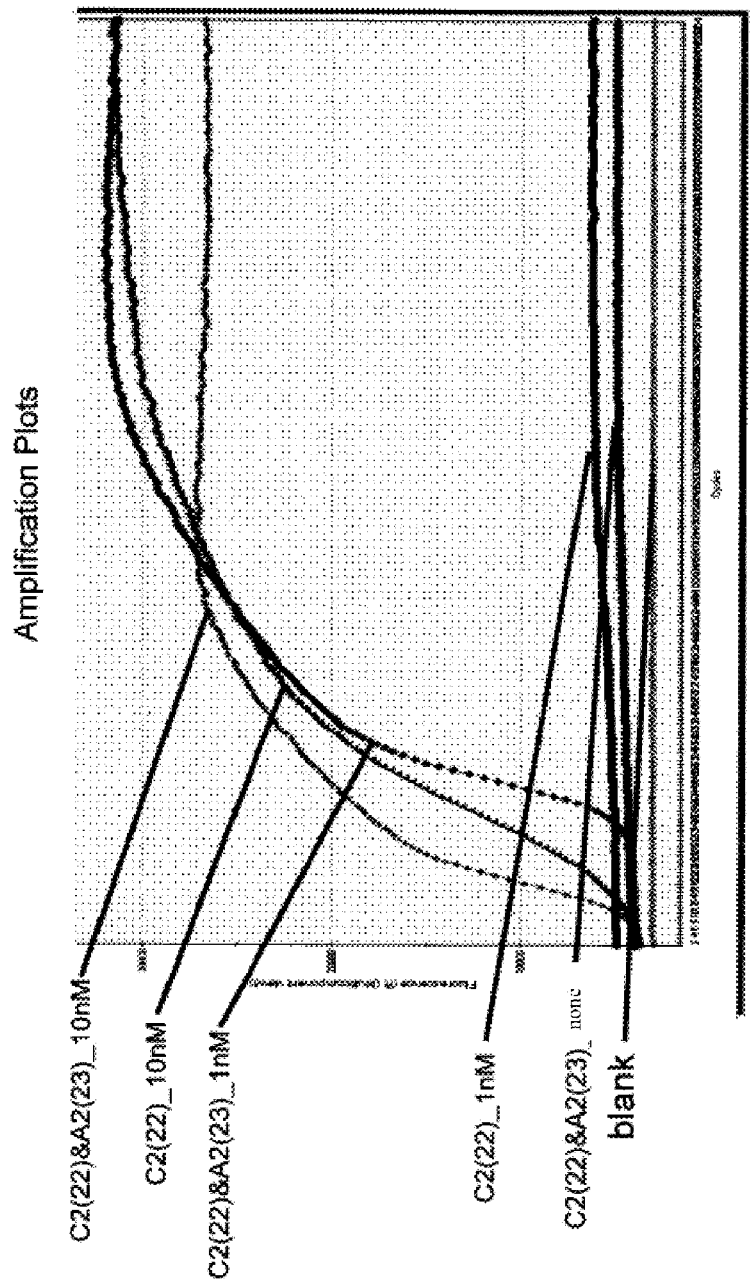

[Figure 29]
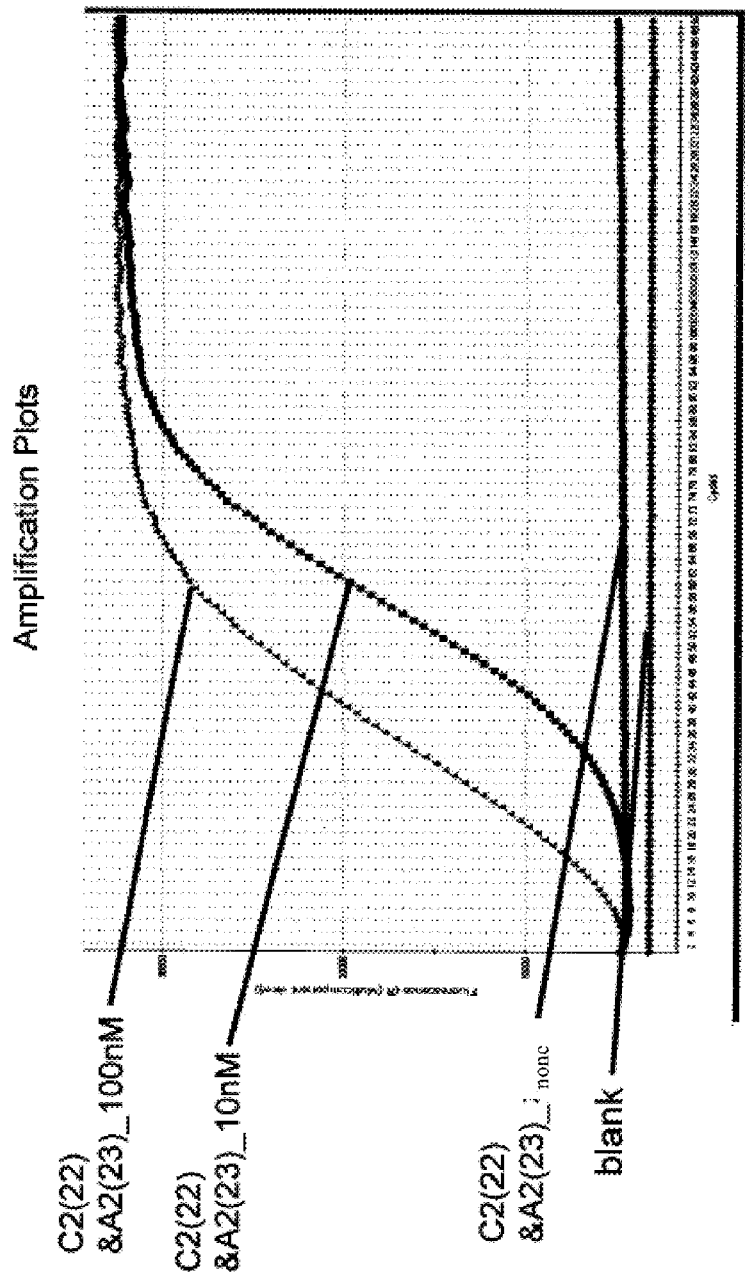

[Figure 30]
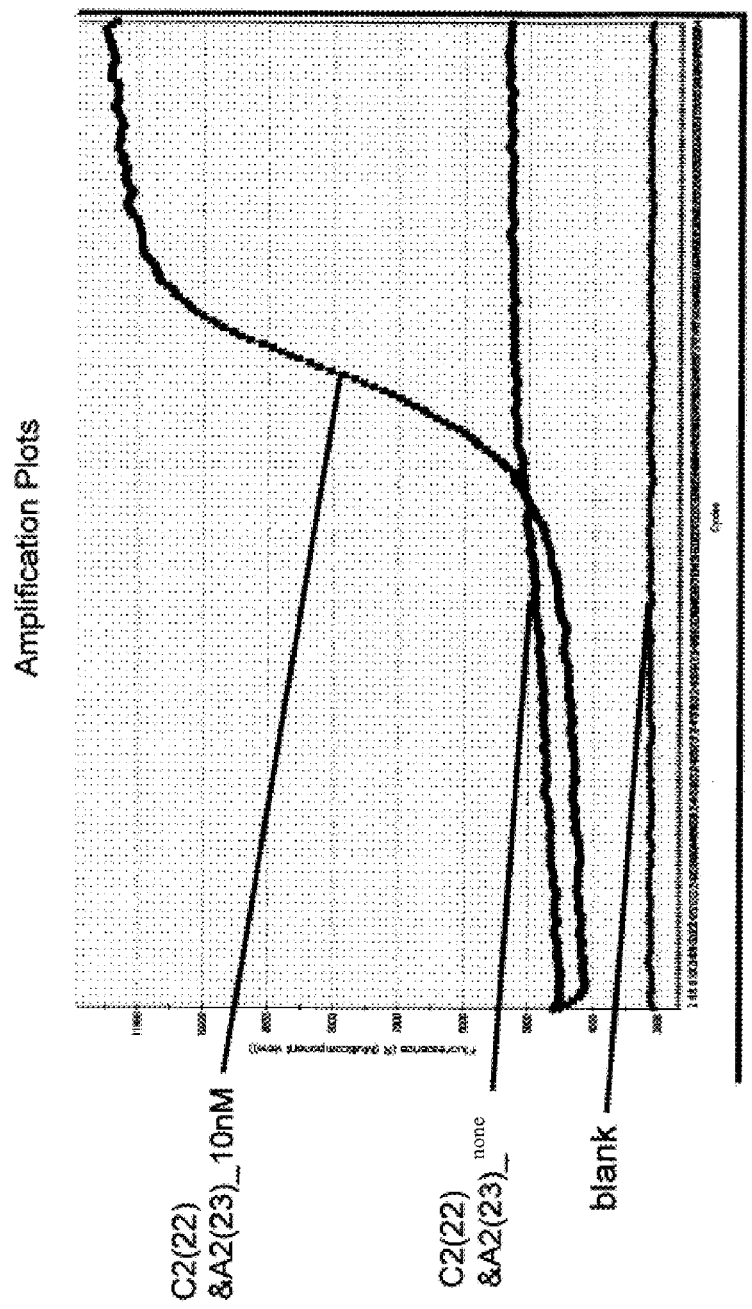

[Figure 31]
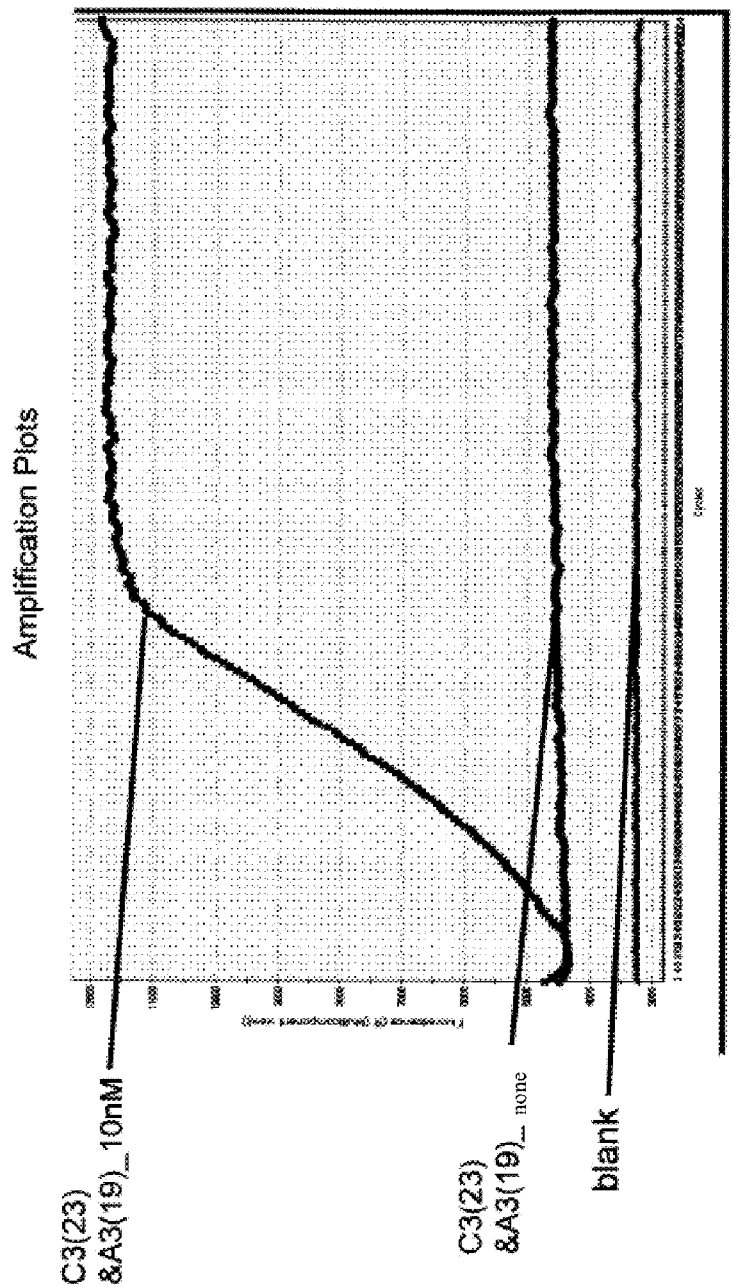

[Figure 32]
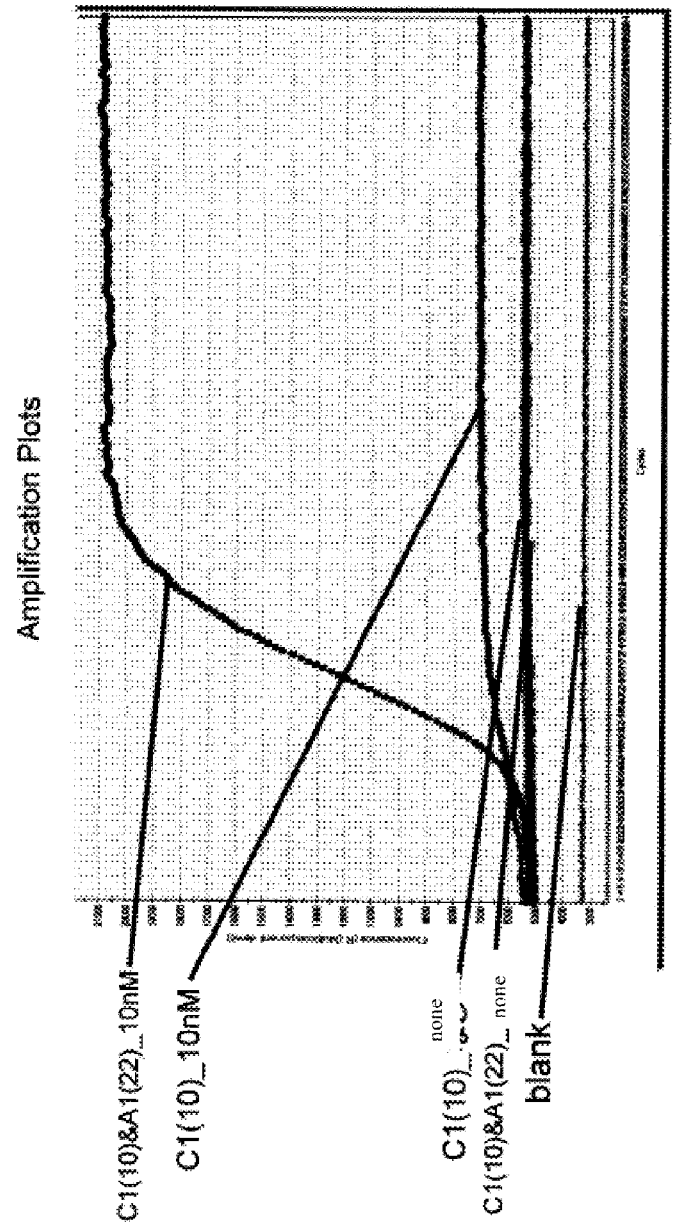

[Figure 33]
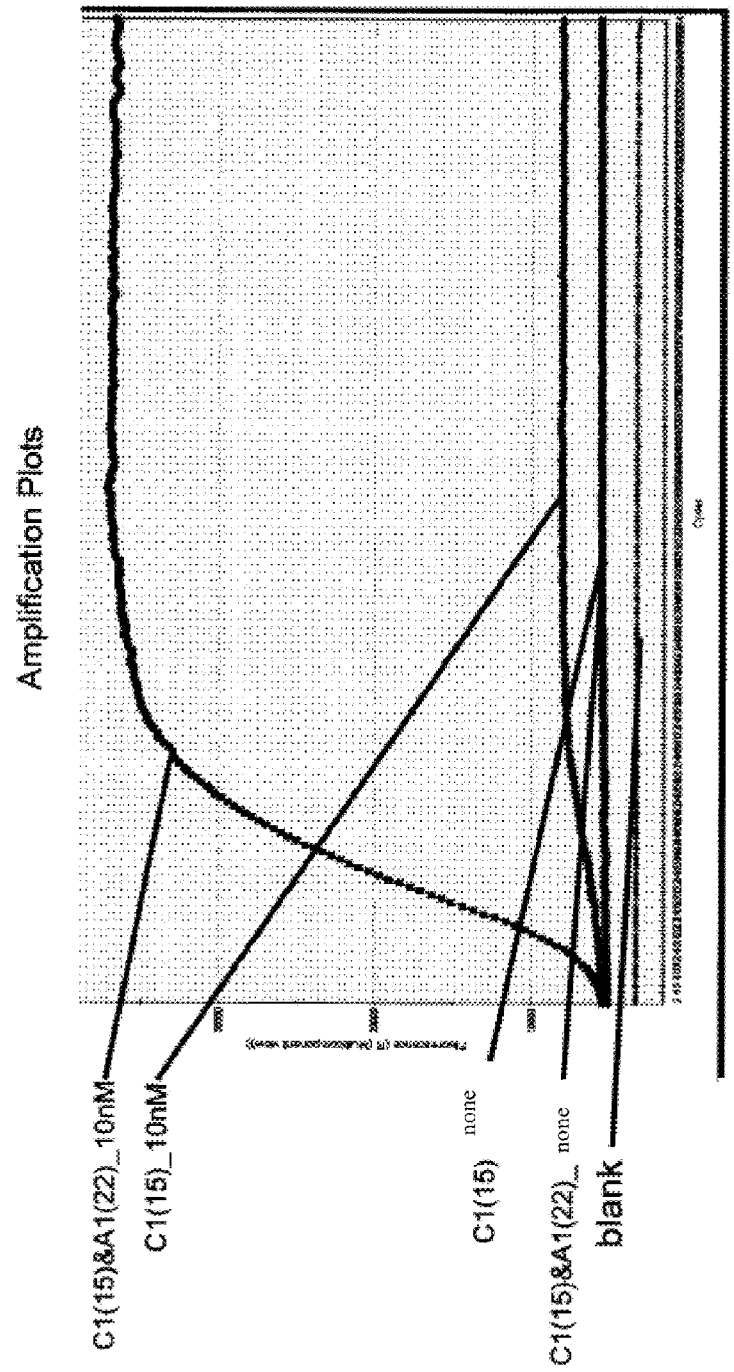

[Figure 34]
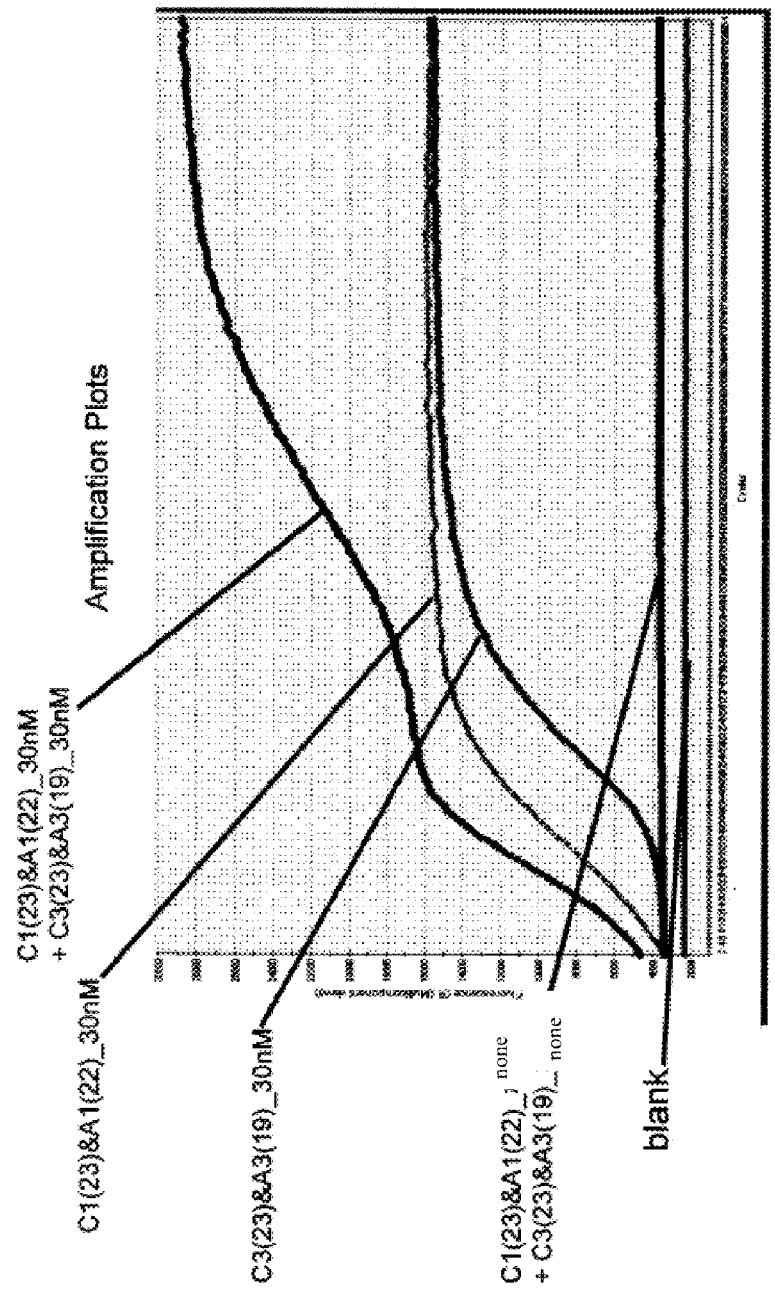

[Figure 35]
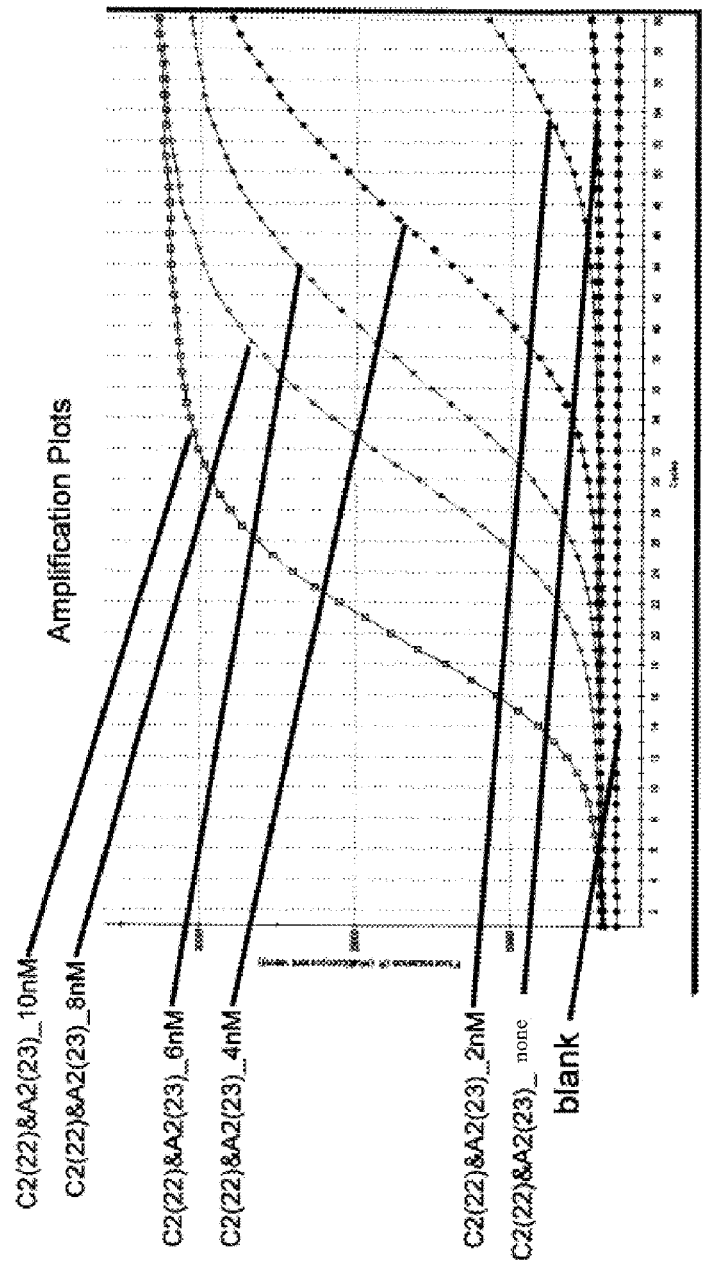

[Figure 36]
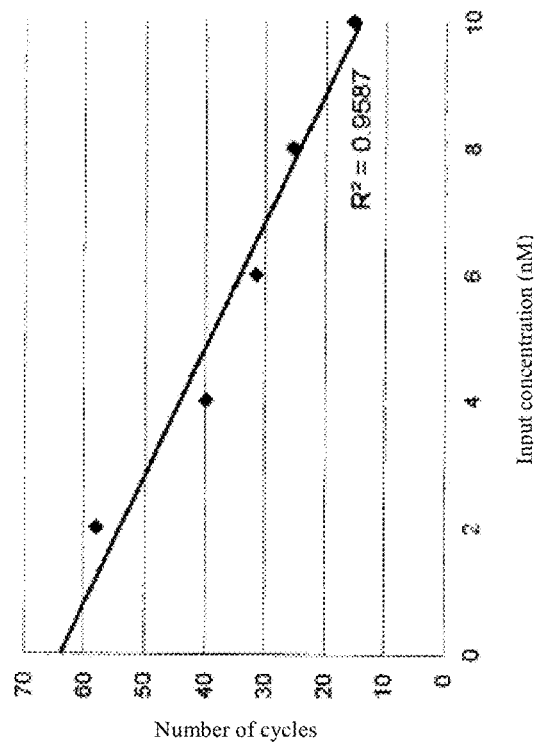

[Figure 37]
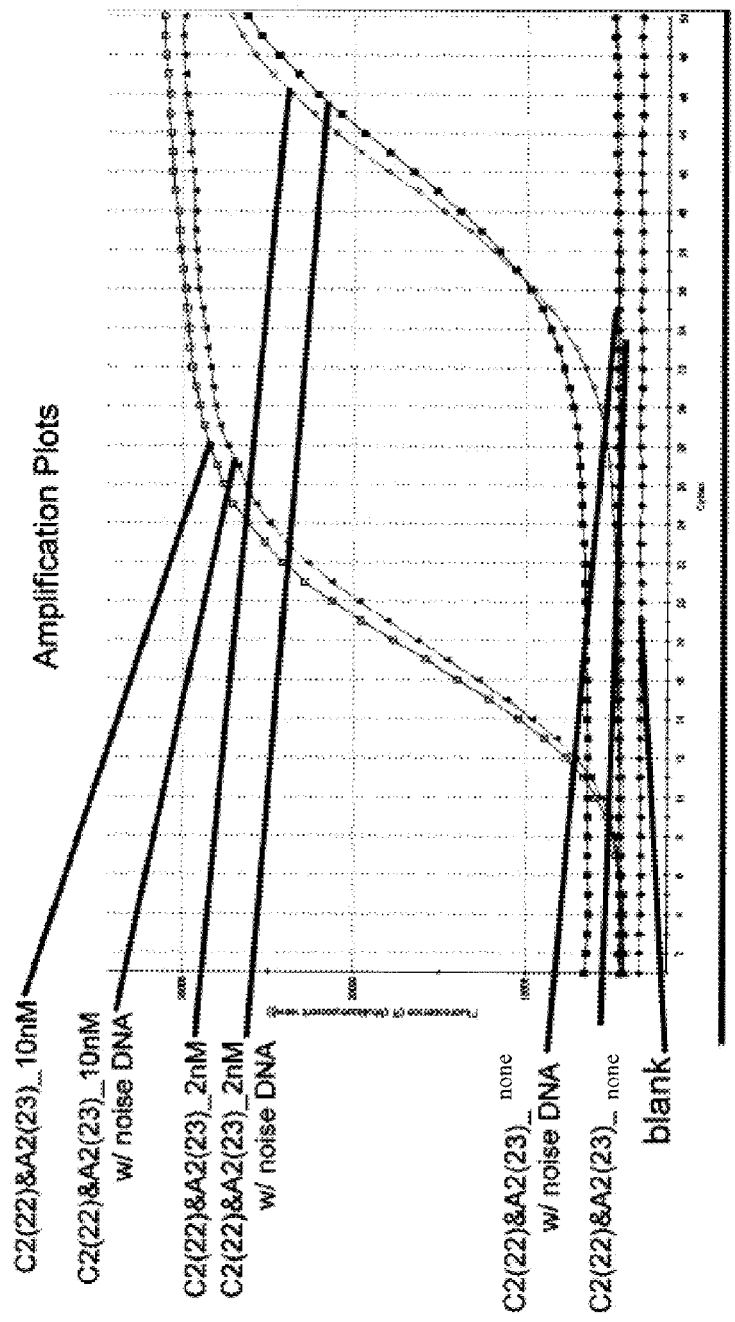

[Figure 38]
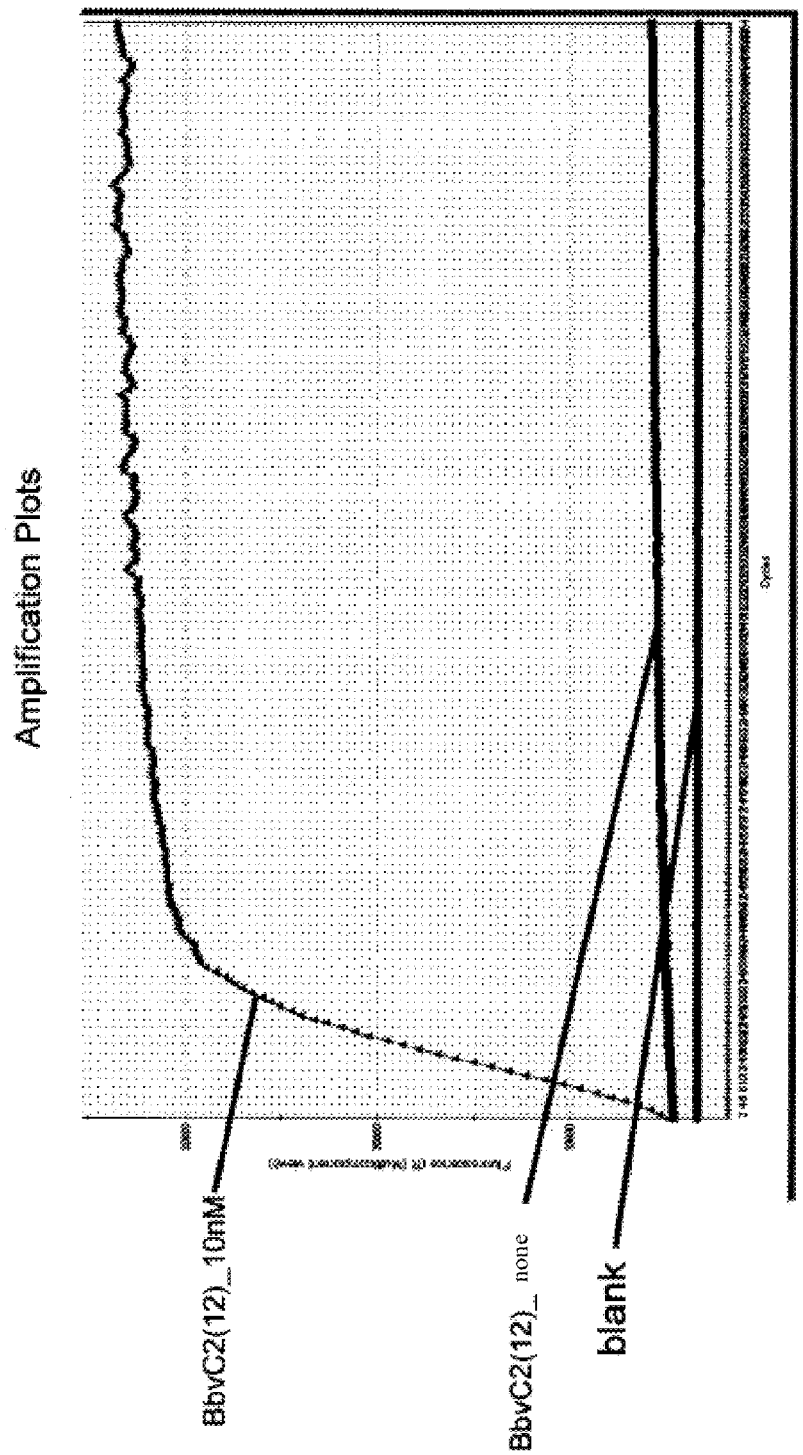

[Figure 39]
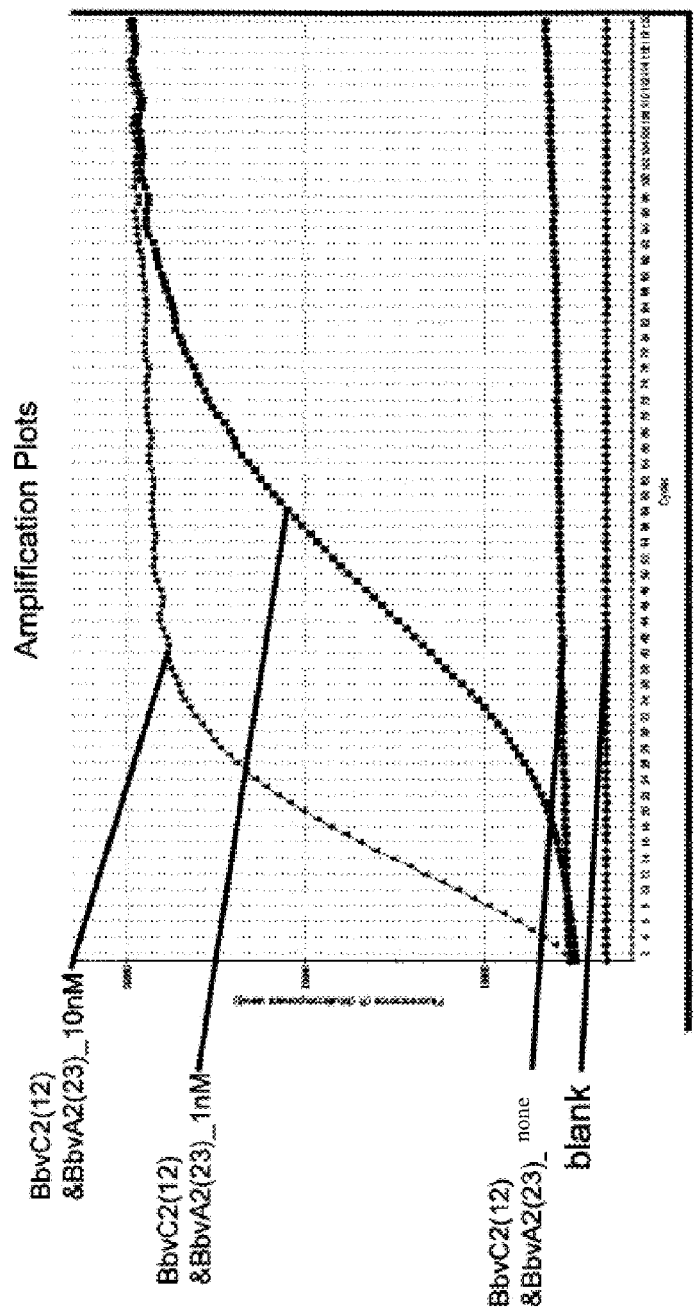

METHOD AND KIT FOR DETECTING TARGET NUCLEIC ACID

TECHNICAL FIELD

The present invention relates to a method for detecting a nucleic acid (DNA or RNA) useful for, for example, genetic analysis. More specifically, the invention relates to a method that can detect even a short-chain nucleic acid.

BACKGROUND ART

Detection of Nucleic acids (such as DNA and RNA) is important in various fields and uses, including medicine and biology, such as the evaluation of the existence of microorganisms, diagnosis of infection, evaluation of gene polymorphism, and patient profiling, as well as in food examination, environment evaluation, and forensic medicine. Moreover, in recent years, many short-chain nucleic acids (such as miRNA) that perform important roles in vital activities have been discovered, and a need for a means of detecting such short-chain nucleic acids has been increasing.

PCR amplification is generally performed as a method for specifically detecting a nucleic acid with high sensitivity (e.g., U.S. Pat. Nos. 4,683,195, 4,683,202, and 4,800,159). In the PCR, a nucleic acid is amplified, for example, through a reaction consisting of three steps: dissociation (denaturation) of a double-stranded template DNA into single strands, annealing of primers to the single-stranded template DNAs, and synthesis (extension) of a complementary strand from each primer. In usual PCR, the denaturation process, the annealing process, and the extension process are carried out at different temperatures with a thermal cycler. Consequently, expensive temperature cycle control equipment is necessary to perform such a reaction, resulting in a problem that the method is prevented from being employed in field examinations, point-of-care (bedside) diagnoses, and inexpensive examinations. Moreover, since the reaction is carried out at three different temperatures, the reaction has problems that the temperature control is troublesome and that the time loss increases in proportion to the number of cycles. Additionally, the exponential amplification requires multiple primers, and a short-chain nucleic acid that cannot ensure a primer binding sequence cannot be directly detected. Accordingly, it has been proposed to carry out amplification in combination with another reaction that adds a primer sequence to the target nucleic acid as pre-processing. However, the additional process for the addition reaction makes the detection operation more complicated and take longer time, needs the reagents to be used, and also has risks of a decrease in sensitivity and of losing the quantitativity due to partial or complete loss of the sample. Furthermore, there is a risk that the quantitative ratio information between multiple samples is lost due to a variation in efficiency of the process of adding a different sequence.

Accordingly, methods for nucleic acid amplification that can be performed under isothermal conditions have been developed as alternatives to PCR. Examples of these methods include strand displacement amplification method (SDA) described in G. T. Walker, M. C. Little, J. G. Nadeau, and D. D. Shank, "Isothermal in vitro amplification of DNA by a restriction enzyme/DNA polymerase system", Proc. Natl. Acad. Sci. USA, 89, 392-396 (1992) and Japanese Patent Publication No. Hei 7-114718; loop-mediated isothermal amplification (LAMP) described in International Publication No. WO 00/28082; and isothermal and chimeric primer-initiated amplification of nucleic acids (ICAN) described in International Publication No. WO 02/16639.

In the SDA described by G. T. Walker et al., detection reactions occur even in systems not containing target nucleic acids in some cases, and the evaluation results in sensitivity and specificity are therefore questionable. The SDA described in Japanese Patent Publication No. Hei 7-114718 is a system of ultimately amplifying DNA and can amplify a target nucleic acid (and its complementary strand) in a sample through displacement of a double strand mediated by a DNA polymerase and a restriction enzyme. This method needs four different primers, of which two are required to be designed so as to include the recognition site of the restriction enzyme. This method cannot be used for direct amplification of short-chain nucleic acids.

The LAMP also needs four different primers that recognize six regions and thereby can amplify a target gene. In other words, in this method, a first primer anneals to the template strand to cause an extension reaction, and then the extended strand by the first primer is separated from the template strand by a strand displacement reaction by a second primer designed upstream of the first primer. On this occasion, a stem loop structure is formed at the 5' end portion of the extended strand due to the structure of the removed first primer extension product, and this method cannot be used for direct amplification of short-chain nucleic acids.

Additionally, in Y. Weizmann, M. K. Beissenhirtz, Z. Cheglakov, R. Nowarski, and I. Willner, "A virus spotlighted by an autonomous DNA machine", Angew. Chem. Int. Ed., 45, 7384-7388 (2006), DNA (deoxyribozyme) having an enzyme activity is synthesized using a sequence that binds to the detection target nucleic acid as a primer in the extension reaction by a DNA polymerase having nicking ability and strand displacement ability, and then detection is carried out using the molecules generated by the peroxidase reaction of the deoxyribozyme as a signal. In also this method, short-chain nucleic acids are not detected.

Patent Literature 1: U.S. Pat. No. 4,683,195
Patent Literature 2: U.S. Pat. No. 4,683,202
Patent Literature 3: U.S. Pat. No. 4,800,159
Patent Literature 4: Japanese Patent Publication No. Hei 7-114718
Patent Literature 5: International Publication No. WO 00/28082
Patent Literature 6: International Publication No. WO 02/16639
Non-Patent Literature 1: G. T. Walker, M. C. Little, J. G. Nadeau, and D. D. Shank, "Isothermal in vitro amplification of DNA by a restriction enzyme/DNA polymerase system", Proc. Natl. Acad. Sci. USA, 89, 392-396 (1992)
Non-Patent Literature 2: Y. Weizmann, M. K. Beissenhirtz, Z. Cheglakov, R. Nowarski, and I. Willner, "A virus spotlighted by an autonomous DNA machine", Angew. Chem. Int. Ed., 45, 7384-7388 (2006)

SUMMARY OF INVENTION

Technical Problem

Accordingly, it is an object of the present invention to provide a method for detecting a nucleic acid (such as DNA or RNA) under isothermal conditions with high sensitivity, in particular, a method that can directly detect even a short-chain nucleic acid.

Solution to Problem

The inventors have diligently studied in order to achieve the object and have found that the object can be achieved by performing a nucleic acid amplification reaction using a specific oligonucleotide in the presence of an endonuclease that is used in a nicking reaction. Thus, the present invention has been accomplished.

That is, the present invention provides a method for detecting a target nucleic acid in a sample, where the method comprises a step (a) of preparing a first oligonucleotide including, in the direction from 5' to 3', a first arbitrary sequence, an endonuclease recognition site that is used in a nicking reaction, and a sequence complementary to the target nucleic acid, a step (b) of carrying out a nucleic acid amplification reaction using the target nucleic acid contained in the sample as a primer in the presence of an endonuclease that recognizes the endonuclease recognition site that is used in the nicking reaction, and a step (c) of detecting the oligonucleotide obtained by the nucleic acid amplification reaction and having a sequence complementary to the first arbitrary sequence.

In addition, the present invention provides a method for detecting a target nucleic acid in a sample, where the method comprises a step (a) of preparing a first oligonucleotide including, in the direction from 5' to 3', a first arbitrary sequence, an endonuclease recognition site that is used in a nicking reaction, and a sequence complementary to the target nucleic acid and a second oligonucleotide including, in the direction from 5' to 3', a second arbitrary sequence having a sequence that is substantially homologous to the first arbitrary sequence, an endonuclease recognition site that is used in a nicking reaction, and a sequence that is substantially homologous to the first arbitrary sequence, a step (b) of carrying out a nucleic acid amplification reaction using the target nucleic acid contained in the sample as a primer in the presence of an endonuclease recognizing the endonuclease recognition site to be used in the nicking reaction, and a step (c) of detecting an oligonucleotide obtained by the nucleic acid amplification reaction and having a sequence complementary to the second arbitrary sequence.

The method of the present invention may further comprises a step (d) of performing a nucleic acid amplification reaction in the presence of the target nucleic acid having a known concentration, the first oligonucleotide, and the endonuclease and measuring an oligonucleotide obtained through the nucleic acid amplification reaction and having a sequence complementary to the first arbitrary sequence, a step (e) of forming a calibration curve from the measurement results obtained by performing the step (d) with the target nucleic acid at different concentrations, and a step (f) of determining the concentration of the target nucleic acid to be detected on the basis of the calibration curve.

Additionally, in the step (d), the nucleic acid amplification reaction may be further carried out in the presence of the second oligonucleotide.

In the method for detecting a target nucleic acid of the present invention, the nucleic acid amplification reaction is preferably carried out under isothermal conditions.

The endonuclease can be a nicking endonuclease.

Examples of the nicking endonuclease used in the present invention include Nb.BbvCI, Nb.BsmI, Nb.BsrDI, Nb.BtsI, Nt.AlwI, Nt.BbvCI, Nt.BspQI, Nt.BstNBI, Nt.CviPII, and Nt.BsmAI.

In the nucleic acid amplification reaction in the method for detecting a target nucleic acid of the present invention, a DNA polymerase having strand displacement ability is preferably used.

In the method for detecting a target nucleic acid of the present invention, the DNA polymerase used in the nucleic acid amplification reaction is one selected from the group consisting of Klenow fragments (including variants lacking 3'→5' exonuclease activity) of DNA polymerase I derived from *E. coli*, 5'→3' exonuclease-deficient Bst DNA polymerase derived from *Bacillus stearothermophilus*, and 5'→3' exonuclease-deficient Bca DNA polymerase derived from *Bacillus caldotenax*.

The 3' end of the first oligonucleotide is preferably modified.

The 3' end of the second oligonucleotide is also preferably modified.

In addition, the present invention provides a kit for detecting a target nucleic acid in a sample, wherein the kit comprises a first oligonucleotide including, in the direction from 5' to 3', a first arbitrary sequence, an endonuclease recognition site that is used in a nicking reaction, and a sequence complementary to the target nucleic acid.

The present invention further provides a kit for detecting a target nucleic acid in a sample, wherein the kit comprises a first oligonucleotide including, in the direction from 5' to 3', a first arbitrary sequence, an endonuclease recognition site that is used in a nicking reaction, and a sequence complementary to the target nucleic acid and a second oligonucleotide including, in the direction from 5' to 3', a second arbitrary sequence having a sequence that is substantially homologous to the first arbitrary sequence, an endonuclease recognition site that is used in a nicking reaction, and a sequence that is substantially homologous to the first arbitrary sequence.

Advantageous Effects of Invention

The method for detecting a target nucleic acid of the present invention can detect a nucleic acid (such as DNA or RNA) under isothermal conditions, in particular, it is possible to directly detect even a short-chain nucleic acid. Moreover, the method of the present invention can easily quantitatively measure a target nucleic acid. The method of the present invention also can detect and quantitatively measure a target nucleic acid in a sample that contains a variety of impurities.

BRIEF DESCRIPTION OF DRAWINGS

FIG. 1 is a diagram schematically illustrating the functional mechanism of the method for detecting a target nucleic acid of the present invention.

FIG. 2 is a diagram schematically illustrating the functional mechanism of the method for detecting a target nucleic acid of the present invention.

FIG. 3 is a graph showing the results of nucleic acid detection using sequence conversion DNAs.

FIG. 4 is a graph showing the results of nucleic acid detection using sequence conversion DNAs.

FIG. 5 is a graph showing the results of nucleic acid detection using sequence conversion DNAs.

FIG. 6 is a graph showing the results of nucleic acid detection using sequence conversion DNAs.

FIG. 7 is a graph showing the results of nucleic acid detection using sequence conversion DNAs.

FIG. 8 is a graph showing the results of nucleic acid detection using sequence conversion DNAs.

FIG. 9 is a graph showing the results of nucleic acid detection using sequence conversion DNAs.

FIG. 10 is a graph showing the results of nucleic acid detection using sequence conversion DNAs.

FIG. 11 is a graph showing the results of nucleic acid detection using sequence conversion DNAs.

FIG. 12 is a graph showing the results of nucleic acid detection using sequence conversion DNAs.

FIG. 13 is a graph showing the results of nucleic acid detection using sequence conversion DNAs.

FIG. 14 is a graph showing the results of nucleic acid detection using sequence conversion DNAs.

FIG. 15 is a graph showing the results of nucleic acid detection using sequence conversion DNAs.

FIG. 16 is a graph showing the results of nucleic acid detection using sequence conversion DNAs.

FIG. 17 is a graph showing the results of nucleic acid detection using sequence conversion DNAs.

FIG. 18 is a graph showing the results of nucleic acid detection using sequence conversion DNAs.

FIG. 19 is a graph showing the results of nucleic acid detection using sequence conversion DNAs.

FIG. 20 is a graph showing the results of nucleic acid detection using sequence conversion DNAs.

FIG. 21 is a graph showing the results of nucleic acid detection using a sequence conversion DNA and a signal amplification DNA.

FIG. 22 is a graph showing the results of nucleic acid detection using a sequence conversion DNA and a signal amplification DNA.

FIG. 23 is a graph showing the results of nucleic acid detection using a sequence conversion DNA and a signal amplification DNA.

FIG. 24 is a graph showing the results of nucleic acid detection using a sequence conversion DNA and a signal amplification DNA.

FIG. 25 is a graph showing the results of nucleic acid detection using a sequence conversion DNA and a signal amplification DNA.

FIG. 26 is a graph showing the results of nucleic acid detection using a sequence conversion DNA and a signal amplification DNA.

FIG. 27 is a graph showing the results of nucleic acid detection using a sequence conversion DNA and a signal amplification DNA.

FIG. 28 is a graph showing the results of nucleic acid detection using a sequence conversion DNA and a signal amplification DNA.

FIG. 29 is a graph showing the results of nucleic acid detection using a sequence conversion DNA and a signal amplification DNA.

FIG. 30 is a graph showing the results of nucleic acid detection using a sequence conversion DNA and a signal amplification DNA.

FIG. 31 is a graph showing the results of nucleic acid detection using a sequence conversion DNA and a signal amplification DNA.

FIG. 32 is a graph showing the results of nucleic acid detection using a sequence conversion DNA and a signal amplification DNA.

FIG. 33 is a graph showing the results of nucleic acid detection using a sequence conversion DNA and a signal amplification DNA.

FIG. 34 is a graph showing the results confirmed that two types of target nucleic acids can be each detected simultaneously using a solution containing the both target nucleic acids.

FIG. 35 is a graph showing the results confirmed that the time until the fluorescence intensity reaches a particular level changes depending on the concentration of the target nucleic acid.

FIG. 36 is a calibration curve formed from the results of FIG. 35.

FIG. 37 is a graph showing the results confirmed that a target nucleic acid can be detected even if the sample contains nucleic acids other than the target nucleic acid.

FIG. 38 is a graph showing the results of nucleic acid detection using a sequence conversion DNA.

FIG. 39 is a graph showing the results of nucleic acid detection using a sequence conversion DNA and a signal amplification DNA.

DESCRIPTION OF EMBODIMENTS

The method of the present invention for detecting a target nucleic acid in a sample will now be described.

A first embodiment of the method of the present invention for detecting a target nucleic acid in a sample will be described.

The method of the present invention for detecting a target nucleic acid in a sample comprises a step (a) of preparing a first oligonucleotide including, in the direction from 5' to 3', a first arbitrary sequence, an endonuclease recognition site that is used in a nicking reaction, and a sequence complementary to the target nucleic acid, a step (b) of carrying out a nucleic acid amplification reaction using the target nucleic acid contained in the sample as a primer in the presence of an endonuclease that recognizes the endonuclease recognition site that is used in the nicking reaction, and a step (c) of detecting the oligonucleotide obtained by the nucleic acid amplification reaction and having a sequence complementary to the first arbitrary sequence.

The step (a) will be described with reference to the figures. FIG. 1 is a diagram schematically illustrating the functional mechanism of a first embodiment of the method for detecting a target nucleic acid of the present invention. The first oligonucleotide (hereinafter also referred to as sequence conversion DNA throughout the specification) including, in the direction from 5' to 3', a first arbitrary sequence, an endonuclease recognition site that is used in a nicking reaction, and a sequence complementary to the target nucleic acid, will be first described. The sequence conversion DNA includes, in the direction from 5' to 3', a first arbitrary sequence (A), an endonuclease recognition site (B) that is used in a nicking reaction, and a sequence (C) complementary to the target nucleic acid.

In the method for detecting a target nucleic acid of the present invention, the sequence conversion DNA is prepared. The first arbitrary sequence in the sequence conversion DNA has a first arbitrary sequence at the 5' end. As will be described below, the first arbitrary sequence is a site serving as a template for the extension reaction by a DNA polymerase and may be any sequence. The number of nucleotides of the sequence is not specifically limited and may be about 5 to 50, about 5 to 30, or about 10 to 20, from the standpoint of ease in handling.

The endonuclease recognition site (B) that is used in a nicking reaction will be described. Throughout the specification, the "nicking reaction" refers to a reaction cleaving only one strand of a double-stranded nucleic acid. Consequently, the endonuclease recognition site (B) that is used in the nicking reaction is a site recognized by an endonuclease cleaving only one strand of a double-stranded DNA having a particular sequence, and, as will be described below, after the start of extension of the DNA by the DNA polymerase, the extended oligonucleotide portion is cleaved by DNA polymerase activity. The endonuclease used in the present invention can be any one that can be used in a nicking reaction. Many endonucleases are known, together with the recognition sequences, as those used in such a reaction, and a skilled person can select an appropriate one from such endonucleases. Examples of the endonuclease include nicking endonucleases and restriction enzymes.

A restriction enzyme is an enzyme that typically cleaves both strands of a double strand, but can be used in a nicking reaction, which cleaves only one strand, by, for example, applying a chemical modification that is not cleaved by the restriction enzyme to one strand of a double-stranded nucleic acid (see Patent Literature 4, for example). Specifically, for example, a restriction enzyme can be used in a nicking reaction by replacing the oxygen atom of phosphodiester linkage of one strand with sulfur atoms.

A nicking endonuclease is used as an endonuclease to be used in a nicking reaction. By using a nicking endonuclease, the phosphodiester linkage of one strand of a double-strand DNA is cleaved to generate a phosphate group on the 5' side of the cleavage site and a hydroxyl group on the 3' side. Examples of the nicking endonuclease include Nb.BbvCI, Nb.BsmI, Nb.BsrDI, Nb.BtsI, Nt.AlwI, Nt.BbvCI, Nt.BspQI, Nt.BstNBI, Nt.CviPII, and Nt.BsmAI.

The sequence (C) complementary to a target nucleic acid may be designed with consideration to the sequence and the number of nucleotides of the target nucleic acid to be detected, and the method for detecting a target nucleic acid of the present invention can also detect short-chain nucleic acids.

For example, in a case of detecting a sequence corresponding to a human micro-RNA sequence, TGGCTCAGTTCAGCAGGAACAG (SEQ ID NO 1) (hsa-miD-24), as the target nucleic acid, CTGTTCCTGCTGAACTGAGCCA (SEQ ID NO: 2) and CTGTTCCTGCTGAAC (SEQ ID NO: 3) are used as the sequence (C) of the sequence conversion DNA. In a case of detecting a sequence corresponding to a human micro-RNA sequence, AGCAGCATTGTACAGGGCTATCA (SEQ ID NO: 4) (hsa-miD-107), as the target nucleic acid, TGATAGCCCTGTACAATGC (SEQ ID NO: 5) and TGATAGCCCTGTACAATGCTGCT (SEQ ID NO: 6) are used as the sequence (C) of the sequence conversion DNA. In the case of detecting a sequence corresponding to a human micro-RNA sequence, AGCTACATTGTCTGCTGGGTTTC (SEQ ID NO: 7) (hsa-miD-107), as the target nucleic acid, GAAACCCAGCAG (SEQ ID NO: 8), GAAACCCAGC (SEQ ID NO: 9), and GAAACCCAGCAGACAATGTAGCT (SEQ ID NO: 10) are used as the sequence (C) of the sequence conversion DNA.

The method of the present invention for detecting a target nucleic acid in a sample can be used, for example, for diagnosis of cancer or infection. For example, cancer or infection can be diagnosed by detecting (quantitative detection) a specific nucleic acid held by a bacterium or virus that causes the cancer or the infection or a nucleic acid containing a nucleotide sequence specific to the cancer. Infection can be diagnosed by detecting a nucleic acid sequence specific to a bacterium or virus that causes the infection. Cancer can also be detected (quantitative detection) of an RNA of which amount of transcription in cancer cells is different from that in normal cells. That is, the detection is possible by cleaving a bacterial or viral nucleic acid with, for example, a restriction enzyme such that a nucleotide sequence specific to the bacterium or the virus is located at the 3' end to use the cleaved nucleic acid as a target nucleic acid and designing a sequence conversion DNA so as to contain a sequence complementary to the target nucleic acid. In addition, whether a specific sequence of a bacterial or viral nucleic acid is present can be detected by designing a DNA having a sequence complementary to the specific sequence and forming an appropriate hairpin structure to be used as an adapter and then designing a sequence conversion DNA so as to contain a sequence complementary to the 3' end portion of the hairpin DNA sequence for the adapter.

Throughout the specification, a nucleotide sequence is written from the nucleic acid 5' end to the 3' end of the nucleic acid.

The 3' end of the sequence conversion DNA is preferably modified such that an extension reaction does not occur from the 3' end side. Examples of the modification include TAMRA, DABCYL, and FAM. In addition, the modification may be, for example, biotinylation, fluorochromation, phosphorylation, thiolation, or amination.

The sequence conversion DNA may contain intervening sequence(s) that do not affect a nicking reaction between the first arbitrary sequence (A) and the endonuclease recognition site (B) used in the nicking reaction, between the endonuclease recognition site (B) used in the nicking reaction and the sequence (C) complementary to the target nucleic acid, and/or at the 3' end side of the sequence (C) complementary to the target nucleic acid. Alternatively, the nucleotides of the first arbitrary sequence (A) and the sequence of the endonuclease recognition site (B) used in the nicking reaction may partially overlap with each other and/or the nucleotides of the sequence of the endonuclease recognition site (B) used in the nicking reaction and the sequence (C) complementary to the target nucleic acid may partially overlap with each other. The sequence conversion DNA can be synthesized by a known method such as a phosphoramidite method, a phosphotriester method, an H-phosphonate method, or a thiophosphonate method.

The step (b) in the method for detecting a target nucleic acid of the present invention is a step of carrying out a nucleic acid amplification reaction using the target nucleic acid contained in the sample as a primer in the presence of an endonuclease that recognizes the endonuclease recognition site used in the nicking reaction.

As shown in FIG. 1, if a target nucleic acid (D) to be detected is present in a sample, the target nucleic acid (D) hybridizes to the sequence (C) complementary thereto. The target nucleic acid serves as a primer to start a nucleic acid amplification reaction by the action of a DNA polymerase. The reaction conditions for the nucleic acid amplification reaction can be appropriately determined by a skilled person depending on the nucleic acid amplification reaction used.

The sample used in the method for detecting a target nucleic acid of the present invention may be any sample possibly containing the target nucleic acid that is detected in the present invention or may be prepared or isolated from such a sample. The sample containing a nucleic acid is not specifically limited, and examples thereof include samples derived from living subjects, such as whole blood, serum, buffy coat, urine, feces, cerebrospinal fluid, seminal fluid, saliva, tissue (such as cancerous tissue or lymph nodes), cell cultures (such as mammalian cell cultures or bacterial cultures); samples containing nucleic acids, such as viroids, viruses, bacteria, fungi, yeast, plants, and animals; samples (such as food and biological preparations) that may contain or be infected with microorganisms such as viruses or bacteria, and samples that may contain biological substances, such as soil and wastewater. Furthermore, a nucleic acid-containing preparation prepared by treating such a sample by a known method may be used as a sample. Examples of the preparation include cell breakage and samples obtained by fractionation thereof, nucleic acids in the samples, and specific nucleic acid molecular groups such as mRNA-enriched samples. The ample used in the method for detecting a target nucleic acid of the present invention is not limited to those derived from biological and natural products as mentioned above and may be a sample containing a synthetic oligonucleotide.

The nucleic acid as a subject to be detected by the method for detecting a target nucleic acid of the present invention may be either DNA or RNA. DNA includes cDNA, genomic DNA, and synthetic DNA, and RNA includes total RNA, mRNA, rRNA, siRNA, hnRNA, piRNA, aRNA, miRNA, and synthetic RNA, but the subject is not limited to them, and all oligonucleotides classified as DNA or RNA can be the subject to be detected. Chimeric oligonucleotides composed of DNA and RNA, oligonucleotides containing unnatural nucleotides, and nucleic acid molecules other than DNA and RNA are also subjects to be detected in the present invention. The present invention can detect a nucleic acid with high sensitivity even if the nucleic acid is a short-chain nucleic acid.

In the method for detecting a target nucleic acid of the present invention, a nucleic acid amplification reaction is performed in the presence of a nicking endonuclease that recognizes the nicking endonuclease recognition site. The nicking endonuclease is as described above.

In the present invention, the nucleic acid amplification reaction is preferably performed under isothermal conditions. The term "isothermal" refers to that substantially constant temperature conditions are maintained so that an enzyme and a primer (in the present invention, the target nucleic acid in a sample functions as a primer) can substantially function. The term "substantially constant temperature conditions" refers to not only accurately maintaining the preset temperature, but also allowing a temperature change that does not impair the substantial functions of the enzyme and the primer. A nucleic acid amplification reaction under constant temperature conditions can be performed by maintaining a temperature at which the activity of the enzyme used can be maintained (this means that even if enzyme activity weakens with the progress of the reaction, a temperature at which the method of the present invention can be performed can be employed). Additionally, a stringency level is preferably set such that the target nucleic acid anneals to the first oligonucleotide as a primer in the nucleic acid amplification reaction. Accordingly, the reaction temperature is preferably approximately 20° C. to approximately 75° C. and more preferably approximately 35° C. to approximately 65° C.

The DNA polymerase used in the nucleic acid amplification reaction preferably has a chain displacement activity (chain displacement ability), and an ordinary mesophilic or thermal resistant DNA polymerase can be also suitably used. The DNA polymerase substantially not having 5'→3' exonuclease activity is preferred. Examples of the DNA polymerase include Klenow fragments (including variants lacking 3'→5' exonuclease activity) of DNA polymerase I derived from *E. coli*, 5'→3' exonuclease-deficient Bst DNA polymerases derived from *Bacillus stearothermophilus*, and 5'→3' exonuclease-deficient Bca DNA polymerases derived from *Bacillus caldotenax*.

Examples of other reagents that can be used in the nucleic acid amplification reaction include metallic salts such as sodium chloride, magnesium chloride, magnesium acetate, and magnesium sulfate; substrates such as dNTP mix; and buffer solutions such as Tris-HCl buffer, tricine buffer, sodium phosphate buffer, and potassium phosphate buffer. Furthermore, additives such as dimethyl sulfoxide and betaine (N,N,N-trimethylglycine); acidic substances described in International Publication No. WO 99/54455; and cationic complexes can be used.

Next, the step (c) will be described. The step (c) is a step of detecting the oligonucleotide obtained by the nucleic acid amplification reaction in the step (b) and having a sequence complementary to the first arbitrary sequence. The method for detecting a target nucleic acid of the present invention will be described with reference to the figures. As shown in FIG. 1, if a target nucleic acid (D) to be detected is present in a sample, the target nucleic acid (D) hybridizes to the complementary portion of the sequence conversion DNA (C). The target nucleic acid (D) serves as a primer to start a nucleic acid amplification reaction by the action of the DNA polymerase to generate a sequence (E) as the product of the extension reaction by the DNA polymerase. Subsequently, the generation of the sequence (E) makes the endonuclease recognition site (B) used in the nicking reaction double stranded, followed by recognition by the nicking endonuclease to cleave the sequence (E) to generate an oligonucleotide (F). The oligonucleotide (F) generated by the DNA polymerase having chain displacement ability is released from the sequence conversion DNA. The DNA polymerase repeats this reaction to linearly (proportionally) amplify the oligonucleotide (F). Throughout the specification, the oligonucleotide (F) (also the oligonucleotide in a second embodiment described below) is also referred to as a signal DNA.

The method for detecting a target nucleic acid of the present invention detects the thus-generated signal DNA. That is, if the target nucleic acid (D) shown in FIG. 1 does not exist, the nucleic acid amplification reaction shown in FIGS. 1 and 2 does not progress, resulting in no generation of the signal DNA. In contrast, if the target nucleic acid (D) exists, the signal DNA is generated, and the presence of the target nucleic acid (D) can be determined by detecting the signal DNA. In the method for detecting a target nucleic acid of the present invention, since the signal DNA is amplified as long as the target nucleic acid (D) exists even if the amount is very slight, the method is a highly sensitive detection.

The presence of the signal DNA, which is the amplification product obtained by the amplification reaction, can be detected by a method known in the art. For example, gel electrophoresis can detect an amplification product by staining the gel with ethidium bromide, and the sequence and length of the oligonucleotide as a product of the amplification can also be confirmed by performing gel electrophoresis after hybridization of the oligonucleotide to be detected to an oligonucleotide having a complementary sequence. The detection system for detecting the amplification product may be, for example, fluorescence polarization, immunoassay, fluorescence resonance energy transfer, enzyme labeling (such as peroxidase or alkaline phosphatase), fluorescent labeling (such as fluorescein or rhodamine), chemiluminescence, or bioluminescence. Detection can also be performed using a TaqMan probe or a molecular beacon. The amplification product can also be detected by using a labeled nucleotide labeled with a biotin, for example. In such a case, the biotin in the amplification product can be detected using fluorescence-labeled avidin or enzyme-labeled avidin, for example. The amplification product can also be detected with electrodes by using redox intercalator known to those skilled in the art. The amplification product can also be detected using surface plasmon resonance (SPR).

The method for detecting a target nucleic acid in a sample according to the present invention can also be used to quantitatively measure the target nucleic acid in the sample.

That is, the present invention provides a method that is the method described above further comprising a step (d) of performing a nucleic acid amplification reaction in the presence of the target nucleic acid having a known concentration, the first oligonucleotide, and the endonuclease and measuring an oligonucleotide obtained through the nucleic acid amplification reaction and having a sequence complementary to the first arbitrary sequence, a step (e) of forming a calibration curve from the measurement results obtained by performing the step (d) with the target nucleic acid at different concentrations, and a step (f) of determining the concentration of the target nucleic acid to be detected on the basis of the calibration curve.

In other words, the present invention provides a method including implementation of the method described above in a system containing a target nucleic acid with a known concentration, implementation of the method in systems containing the target nucleic acid with different concentrations, and formation of a calibration curve from the measurement results (step (e)). Subsequently, the concentration of the target nucleic acid to be detected is determined (step (f)) based on the calibration curve formed in the step (e).

The calibration curve can be formed from fluorescence intensities in the case of detecting a target nucleic acid by measuring fluorescence.

Next, a second embodiment of the method of the present invention for detecting a target nucleic acid in a sample will be described.

The second embodiment of the method of the present invention for detecting a target nucleic acid in a sample is a method comprising a step (a) of preparing a first oligonucleotide including, in the direction from 5' to 3', a first arbitrary sequence, an endonuclease recognition site that is used in a nicking reaction, and a sequence complementary to the target nucleic acid and a second oligonucleotide including, in the direction from 5' to 3', a second arbitrary sequence having a sequence that is substantially homologous to the first arbitrary sequence, an endonuclease recognition site that is used in a nicking reaction, and a sequence that is substantially homologous to the first arbitrary sequence, a step (b) of carrying out a nucleic acid amplification reaction using the target nucleic acid contained in the sample as a primer in the presence of an endonuclease that recognizes the endonuclease recognition site that is used in the nicking reaction, and a step (c) of detecting the oligonucleotide obtained by the nucleic acid amplification reaction and having a sequence complementary to the second arbitrary sequence.

The step (a) will be described with reference to the figures. FIGS. 1 and 2 are diagrams illustrating the functional mechanism of the method for detecting a target nucleic acid of the present invention. FIG. 1 has been described above. The second oligonucleotide (hereinafter also referred to as signal amplification DNA throughout the specification) that is used in the method for detecting a target nucleic acid of this invention includes, in the direction from 5' to 3', a second arbitrary sequence (A') having a sequence substantially homologous to the first arbitrary sequence, an endonuclease recognition site (B) that is used in a nicking reaction, and a sequence (C') that is substantially homologous to the first arbitrary sequence.

In the method for detecting a target nucleic acid of the present invention, a sequence conversion DNA and a signal amplification DNA are prepared. The first arbitrary sequence in the sequence conversion DNA has a first arbitrary sequence at the 5' end. As described below, the first arbitrary sequence is a site serving as a template for the extension reaction by a DNA polymerase and may be any sequence. The number of nucleotides of the sequence is not specifically limited and may be about 5 to 50, about 5 to 30, or about 10 to 20, from the standpoint of ease in handling.

The endonuclease recognition site (B) and the restriction enzyme used in the nicking reaction have been described above. The endonuclease used in the nicking reaction is a nicking endonuclease and is the same as that described above.

Next, the second oligonucleotide (signal amplification DNA) will be described. The signal amplification DNA has a second arbitrary sequence with a sequence substantially homologous to the first arbitrary sequence on the 5' end side. As described below, this second arbitrary sequence is a site serving as a template for the extension reaction by a DNA polymerase and has a sequence substantially homologous to the first arbitrary sequence. Moreover, the method of the present invention for detecting a target nucleic acid detects a chain that is complementary to the extended portion using the second arbitrary sequence as a template. That point will be described below. The second arbitrary sequence and the first arbitrary sequence have sequences substantially homologous to each other. Consequently, for example, in the case of detecting an amplification product using a molecular beacon as described below, it is possible to detect both the oligonucleotides having a sequence complementary to the first arbitrary sequence and a sequence complementary to the second arbitrary sequence.

Substantially homologous sequences may be completely identical sequences or may be, for example, in the case of detecting an amplification product using a molecular beacon as described below, sequences having deletion, substitution, or addition of one to five, one to four, one to three, one or two, or one nucleotide in a sequence complementary to the first arbitrary sequence generated through an amplification reaction and a sequence complementary to the second arbitrary sequence in a degree allowing detection by a single molecular beacon. Furthermore, sequences that do not obstruct the reaction with the molecular beacon may be added.

The endonuclease recognition site (B) used in the nicking reaction in the signal amplification DNA is the same as that described in the sequence conversion DNA. The nicking endonuclease recognition site included in the sequence conversion DNA and the endonuclease recognition site included in the signal amplification DNA may be identical to or different from to each other. The method of the present invention for detecting a target nucleic acid is carried out in the presence of an endonuclease that recognizes the endonuclease recognition site used in the nicking reaction. Therefore, if the sequence conversion DNA and the signal amplification DNA have identical endonuclease recognition sites, the reaction can be carried out using a single endonuclease. Accordingly, the same endonuclease recognition sites are preferred.

The sequence (C') substantially homologous to the first arbitrary sequence is a sequence that hybridizes to the oligonucleotide generated by the activity of a DNA polymerase from the first arbitrary sequence (A). It is therefore preferable that the sequence (C') substantially homologous to the first arbitrary sequence be completely identical to first arbitrary sequence (A). However, for example, the nucleotide length is not necessarily the same, and the sequence (C') may have deletion, substitution, or addition of one to five, one to four, one to three, one or two, or one nucleotide as long as the sequence serves as a primer in the reaction described below.

The 3' end of the signal amplification DNA is preferably modified such that the extension reaction does not occur from the 3' end side. Examples of the modification are the same as those described in the sequence conversion DNA.

The signal amplification DNA may contain intervening sequence(s) that do not affect the reaction between the second arbitrary sequence (A') and the endonuclease recognition site (B) used in the nicking reaction, between the endonuclease recognition site (B) used in the nicking reaction and the sequence (C') substantially homologous to the first arbitrary sequence, and/or at the 3' end side of the sequence (C) complementary to the target nucleic acid. Alternatively, the nucleotides of the second arbitrary sequence (A') and the sequence of the endonuclease recognition site (B) used in the nicking reaction may partially overlap with each other and/or the nucleotides of the sequence of the endonuclease recognition site (B) used in the nicking reaction and the sequence (C') substantially homologous to the first arbitrary sequence may partially overlap with each other. The signal amplification DNA can be synthesized by a known method such as a phosphoramidite method, a phosphotriester method, an H-phosphonate method, or a thiophosphonate method.

The step (b) in the method for detecting a target nucleic acid of the present invention is a step of carrying out a nucleic acid amplification reaction using the target nucleic acid contained in the sample as a primer in the presence of an endonuclease that recognizes the endonuclease recognition site used in the nicking reaction and is the same as that in the first embodiment.

The sample used in the method for detecting a target nucleic acid of the present invention, i.e., the nucleic acid as a subject to be detected, may be either DNA or RNA. DNA includes cDNA, genomic DNA, and synthetic DNA, and RNA includes any of total RNA, mRNA, rRNA, siRNA, hnRNA, piRNA, aRNA, miRNA, and synthetic RNA, but the subject is not limited to them, and all oligonucleotides classified as DNA or RNA can be the subject to be detected. Chimeric oligonucleotides composed of DNA and RNA, oligonucleotides containing unnatural nucleotides, and nucleic acid molecules other than DNA and RNA are also subjects to be detected in the present invention. The present invention can detect a nucleic acid with high sensitivity even if the nucleic acid is a short-chain nucleic acid.

In the method for detecting a target nucleic acid of the present invention, a nucleic acid amplification reaction is performed in the presence of a nicking endonuclease that recognizes the nicking endonuclease recognition site. The nicking endonuclease is as described above.

In the present invention, the nucleic acid amplification reaction is preferably performed under isothermal conditions. The term "isothermal" refers to that substantially constant temperature conditions are maintained so that an enzyme and a primer (in the present invention, the target nucleic acid in a sample functions as a primer) can substantially function. The term "substantially constant temperature conditions" refers to not only accurately maintaining the preset temperature, but also allowing a temperature change that does not impair the substantial functions of the enzyme or the primer. A nucleic acid amplification reaction under constant temperature conditions can be performed by maintaining a temperature at which the activity of the enzyme used can be maintained (this means that even if enzyme activity weakens with the progress of the reaction, a temperature at which the method of the present invention can be performed can be employed). Additionally, a stringency level is preferably set such that the target nucleic acid anneals to the first oligonucleotide as a primer in the nucleic acid amplification reaction. Accordingly, the reaction temperature is preferably approximately 20° C. to approximately 75° C. and more preferably approximately 35° C. to approximately 65° C.

The DNA polymerase used in the nucleic acid amplification reaction preferably has a chain displacement activity (chain displacement capability), and an ordinary mesophilic or thermal resistant DNA polymerase can be also suitably used. The DNA polymerase substantially not having 5'→3' exonuclease activity is preferred. Examples of the DNA polymerase include Klenow fragments (including variants lacking 3'→5' exonuclease activity) of DNA polymerase I derived from *E. coli*, 5'→3' exonuclease-deficient Bst DNA polymerases derived from *Bacillus stearothermophilus*, and 5'→3' exonuclease-deficient Bca DNA polymerases derived from *Bacillus caldotenax*.

Examples of other reagents that can be used in the nucleic acid amplification reaction include metallic salts such as sodium chloride, magnesium chloride, magnesium acetate, and magnesium sulfate; substrates such as dNTP mix; and buffer solutions such as Tris-HCl buffer, tricine buffer, sodium phosphate buffer, and potassium phosphate buffer. Furthermore, additives such as dimethyl sulfoxide and betaine (N,N,N-trimethylglycine); acidic substances described in International Publication No. WO 99/54455; and cationic complexes can be used.

Next, the step (c) in the method of the present invention for detecting a target nucleic acid in a sample will be described. The step (c) is a step detecting the oligonucleotide obtained by the nucleic acid amplification reaction in the step (b) and having a sequence complementary to the first arbitrary sequence.

The method for detecting a target nucleic acid of the present invention will be described with reference to the figures. As shown in FIG. 1, if a target nucleic acid (D) to be detected is present in a sample, the target nucleic acid (D) hybridizes to the complementary portion of the sequence conversion DNA (C). The target nucleic acid (D) serves as a primer to start a nucleic acid amplification reaction by the action of the DNA polymerase to generate a sequence (E) as the product of the extension reaction by the DNA polymerase. Subsequently, the generation of the sequence (E) makes the endonuclease recognition site (B) used in the nicking reaction double stranded, followed by recognition by the nicking endonuclease to cleave the sequence (E) to generate an oligonucleotide (F). The oligonucleotide (F) generated by the DNA polymerase having chain displacement ability is released from the sequence conversion DNA. The DNA polymerase repeats this reaction to linearly (proportionally) amplify the oligonucleotide (F).

Subsequently, as shown in FIG. 2, the oligonucleotide (F) amplified linearly as described above has a sequence complementary to first arbitrary sequence (A) and is therefore hybridizes to the sequence (C') of the signal amplification DNA, i.e., the sequence (C') substantially homologous to the first arbitrary sequence (A) of the sequence conversion DNA. As shown in FIG. 2, the oligonucleotide (F) functions as a primer by hybridizing to the sequence (C') of the signal amplification DNA to start the nucleic acid amplification reaction by the action of the DNA polymerase to generate a sequence (G) as a product of the extension reaction of the DNA polymerase. Subsequently, the generation of the sequence (G) makes the endonuclease recognition site (B) used in the nicking reaction double stranded, followed by recognition by the nicking endonuclease to cleave the sequence (G) to generate an oligonucleotide (H). The oligonucleotide (H) generated by the DNA polymerase having chain displacement ability is released from the signal amplification DNA. The oligonucleotide (H) has a sequence homologous to oligonucleotide (F), and the both are each referred to as a signal DNA.

The method for detecting a target nucleic acid of the present invention detects the thus-generated signal DNA. That is, if the target nucleic acid (D) shown in FIG. 1 does not exist, the nucleic acid amplification reaction shown in FIGS. 1 and 2 does not progress, resulting in no generation of the signal DNA. In contrast, if the target nucleic acid (D) exists, the signal DNA is generated, and that the presence of the target nucleic acid (D) can be determined by detecting the signal DNA. In the method for detecting a target nucleic acid of the present invention, since the signal DNA is exponentially amplified as long as the target nucleic acid (D) exists even if the amount is very slight, the method is a highly sensitive detection.

The presence of oligonucleotide (H) as the amplification product obtained through the reaction can be detected by a method known in the art. For example, gel electrophoresis can detect an amplification product by staining the gel with ethidium bromide, and the sequence and length of the oligonucleotide as a product of the amplification can also be confirmed by performing gel electrophoresis after hybridization of the oligonucleotide to be detected to an oligonucleotide having a complementary sequence. The detection system for detecting the amplification product may be, for example, fluorescence polarization, immunoassay, fluorescence resonance energy transfer, enzyme labeling (such as peroxidase or alkaline phosphatase), fluorescent labeling (such as fluorescein or rhodamine), chemiluminescence, or bioluminescence. Detection can also be performed using a TaqMan probe or a molecular beacon. The amplification product can also be detected by using a labeled nucleotide labeled with a biotin, for example. In such a case, the biotin in the amplification product can be detected using fluorescence-labeled avidin or enzyme-labeled avidin, for example. The amplification product can also be detected with electrodes by using redox intercalator known to those skilled in the art.

The amplification product can also be detected using surface plasmon resonance (SPR).

The second embodiment of the present invention can detect a target nucleic acid with extremely high sensitivity. Though the first embodiment can also detect a target nucleic acid with high sensitivity, the sensitivity of the second embodiment is further increased.

The second embodiment can be used for quantitatively measuring a target nucleic acid in a sample. That is, the present invention provides a method that is the method described above further comprising a step (d) of performing a nucleic acid amplification reaction in the presence of the target nucleic acid having a known concentration, the first oligonucleotide, and the endonuclease and measuring an oligonucleotide obtained through the nucleic acid amplification reaction and having a sequence complementary to the first arbitrary sequence; a step (e) of forming a calibration curve from the measurement results obtained by performing the step (d) with the target nucleic acid at different concentrations; and a step (f) of determining the concentration of the target nucleic acid to be detected on the basis of the calibration curve.

Next, a kit for detecting a target nucleic acid in a sample according to the present invention will be described.

The kit for detecting a target nucleic acid in a sample according to the present invention includes a first oligonucleotide containing, in the direction from 5' to 3', a first arbitrary sequence, an endonuclease recognition site that is used in a nicking reaction, and a sequence complementary to the target nucleic acid. The kit for detecting a target nucleic acid in a sample according to the present invention may further include a second oligonucleotide containing, in the direction from 5' to 3', a second arbitrary sequence having a sequence substantially homologous to the first arbitrary sequence, an endonuclease recognition site that is used in a nicking reaction, and a sequence substantially homologous to the first arbitrary sequence. In other words, the present invention provides a kit for detecting a target nucleic acid in a sample, wherein the kit includes a first oligonucleotide containing, in the direction from 5' to 3', a first arbitrary sequence, an endonuclease recognition site that is used in a nicking reaction, and a sequence complementary to the target nucleic acid and a second oligonucleotide containing, in the direction from 5' to 3', a second arbitrary sequence having a sequence substantially homologous to the first arbitrary sequence, an endonuclease recognition site that is used in a nicking reaction, and a sequence substantially homologous to the first arbitrary sequence.

That is, the kit for detecting a target nucleic acid of the present invention includes the first oligonucleotide (sequence conversion DNA) used in the method for detecting a target nucleic acid in the present invention or further includes the second oligonucleotide (signal amplification DNA). The details of the first oligonucleotide and the second oligonucleotide are as described above.

The kit for detecting a target nucleic acid in a sample according to the present invention may further include a DNA polymerase and a nicking endonuclease. The DNA polymerase and the nicking endonuclease are as described above. The kit of the present invention may further include other reagents such as buffers that are used in order to prepare a sample solution.

The kit of the present invention for detecting a target nucleic acid in a sample is used to carry out the method for detecting a target nucleic acid of the present invention.

EXAMPLES

The present invention will now be described in further detail by examples. Note that the scope of the present invention is not limited to the following examples.

In the following examples, unless otherwise noted, the nucleic acid amplification reaction was performed in 25 µL of a solution of 1×NE buffer 2 (10 mM Tris-HCl, 10 mM $MgCl_2$, 50 mM NaCl, 1 mM DTT (pH 7.9, 25° C.)) containing FAM-DABCYL modification molecular beacon for detecting an amplification product at a concentration of 100 nM at 37° C. with a real-time PCR machine Mx3005P (Stratagene Corporation). Unless otherwise noted, the reaction was carried out using 0.08 units/µL of Large Fragment of Bst DNA polymerase and 0.1 units/µL of Nt.Alwl. Furthermore, unless otherwise noted, the Mx3005P gain setting was ×1. The oligonucleotides and molecular beacons used in the following examples were produced by common methods. In the following examples, those indicated as blank in the figures each show the results of a case of using only a buffer. In the graphs showing the measurement results, the horizontal axis shows the number of measurement cycles, and the vertical axis shows the fluorescence intensity.

Example 1

Detection of Target Nucleic Acid Using Sequence Conversion DNA

An experiment of detecting target nucleic acids was performed using sequence conversion DNAs. The following three oligonucleotides (DNA) having sequences corresponding to human micro RNA molecules: hsa-miR-24, hsa-miR-107, and hsa-miR-221, respectively, were used as the target nucleic acids:

TGGCTCAGTTCAGCAGGAACAG, (SEQ ID NO: 1)

AGCAGCATTGTACAGGGCTATCA, (SEQ ID NO: 4)
and

AGCTACATTGTCTGCTGGGTTTC. (SEQ ID NO: 7)

The sequence conversion DNA used to detect the target nucleic acid of SEQ ID NO: 1 has the following sequence:
TGATAGCCCTGTACAATGCTGCT
CAGAGATCCCTGTTCCTGCTGAACTGAGCCA-(TAMRA) (SEQ ID NO: 11, hereinafter referred to as C2(22)), The sequence conversion DNA used to detect the target nucleic acid of SEQ ID NO: 4 has the following sequence:
TCAACATCAGTCTGATAAGCTA
CAGAGATCCTGATAGCCCTGTACAATGC-(TAMRA) (SEQ ID NO: 12, hereinafter referred to as C3(19)), and The sequence conversion DNA used to detect the target nucleic acid of SEQ ID NO: 7 has the following sequence:
CTGTTCCTGCTGAACTGAGCCA
CAGAGATCCGAAACCCAGCAGACA-(TAMRA) (SEQ ID NO: 13, hereinafter referred to as C1(15)).

C2(22), C3(19), and C1(15) all contain GATCC, which is a nicking endonuclease Nt.AlwI recognition site, and the 3' end side of the sequence GGATCTCTG, which is the complementary sequence to CAGAGATCC, is cleaved by Nt.AlwI.

A target nucleic acid (100 nM: final concentration, hereinafter the same applies in the specification) and a sequence conversion DNA (100 nM) were put in a reaction system, and an amplification reaction was carried out. The results were measured every 30 seconds, and 255 measurement cycles were performed. The same procedure was performed using only a buffer as a control. The results of the experiment performed using only the buffer are shown as "blank" in the figures.

The molecular beacons used in measurement are as follows:

The molecular beacon used in detection of the nucleic acid of SEQ ID NO: 1:
(FAM)-CGCGATGATAGCCCTGTACAATGCTGCT-TCGCG-(DABCYL) (SEQ ID NO: 14), The molecular beacon used in detection of the nucleic acid of SEQ ID NO: 4:
(FAM)-CGCGATCAACATCAGTCTGATAAGC-TATCGCG-(DABCYL) (SEQ ID NO: 15), and The molecular beacon used in detection of the nucleic acid of SEQ ID NO: 7:
(FAM)-CGCGA-CTGTTCCTGCTGAACTGAGC-CATCGCG-(DABCYL) (SEQ ID NO: 16).

The results are shown in FIG. 3. In FIG. 3, the vertical axis shows the fluorescence intensity, and the horizontal axis shows the number of cycles. As obvious from FIG. 3, in all cases of using C2(22), C3(19), or C1(15), the fluorescence intensity increased, and it was revealed that each target nucleic acid functioned as a primer to cause nucleic acid amplification by the action of the DNA polymerase. It was therefore revealed that this system can detect the target nucleic acids of SEQ ID NO: 1, SEQ ID NO: 4, and SEQ ID NO: 7. This experimental example was a system including a target nucleic acid at a high concentration of 100 nM and showed that such a high concentration of a target nucleic acid allows sufficiently rapid amplification of the oligonucleotide as an amplification product to a detectable level and that, therefore, the system can detect whether a target nucleic acid exists in a sample through this reaction system.

Example 2

Detection of Target Nucleic Acid Using Sequence Conversion DNA

An experiment was performed as in Example 1 except that the concentration of each target nucleic acid was 30 nM and that the concentration of each sequence conversion DNA was 30 nM. The following sequence conversion DNAs were used in addition to those used in Example 1. In addition, the same procedure was performed using only a buffer as a control.

The sequence conversion DNA used to detect the target nucleic acid of SEQ ID NO: 1 has the following sequence:
TGATAGCCCTGTACAATGCTGCT
CAGAGATCCCTGTTCCTGCTGAAC-(TAMRA) (SEQ ID NO: 17, hereinafter referred to as C2(15)), The sequence conversion DNA used to detect the target nucleic acid of SEQ ID NO: 7 has the following sequence:
CTGTTCCTGCTGAACTGAGCCA
CAGAGATCCGAAACCCAGCAG-(TAMRA) (SEQ ID NO: 18, hereinafter referred to as C1(12)), and The sequence conversion DNA used to detect the target nucleic acid of SEQ ID NO: 7 has the following sequence:
CTGTTCCTGCTGAACTGAGCCA
CAGAGATCCGAAACCCAGC-(TAMRA) (SEQ ID NO: 19, hereinafter referred to as C1(10)).

In this experiment, the Mx3005P gain setting was ×8, and measurements were performed every 60 seconds for 255 cycles.

The results are shown in FIG. 4. As obvious from FIG. 4, in also cases using C2(22) or C2(15), the fluorescence intensity increased and it was revealed that each target nucleic acid functioned as a primer to sufficiently rapidly amplify the oligonucleotide as an amplification product to a detectable level. It was therefore revealed that the use of C2(22) or C2(15) can detect whether the target nucleic acid of SEQ ID NO: 1 exists in a sample. Moreover, it was revealed that this reaction system also can detect whether the target nucleic acid of SEQ ID NO: 4 exists in a sample using C3(19) and can detect whether the target nucleic acid of SEQ ID NO: 7 exists in a sample using C1(15), C1(12), or C1(10).

Example 3

Detection of Target Nucleic Acid Using Sequence Conversion DNA

An experiment was performed as in Example 1 except that the concentration of each target nucleic acid was 10 nM and that the concentration of each sequence conversion DNA was 10 nM. C1(15), C2(22), and C3(19) were used as sequence conversion DNAs. In this experiment, the Mx3005P gain setting was ×8, measurements were performed every 60 seconds for 255 cycles, and the same procedure was performed using only a buffer as a control. The results are shown in FIG. 5. As obvious from FIG. 5, in also this experiment, the fluorescence intensity increased, and it was revealed that each target nucleic acid functioned as a primer to sufficiently rapidly amplify the oligonucleotide as an amplification product to a detectable level. Thus, this reaction system can detect whether a target nucleic acid exists in a sample.

Example 4

Detection of Target Nucleic Acid Using Sequence Conversion DNA

An experiment was performed as in Example 1 except that the concentration of the target nucleic acid was 30 nM and that the concentration of the sequence conversion DNA was 30 nM. The same procedure was performed using only a buffer as a control. As the sequence conversion DNA for detecting a target nucleic acid of SEQ ID NO 7, C1 (23) having the following sequence was used:

```
                                                       (SEQ ID NO: 22)
CTGTTCCTGCTGAACTGAGCCACAGAGATCCGAAACCCAGCAGACAATGTAGCT-(TAMRA).
```

The experiment was performed simultaneously using three PCR tubes for measurement. In this experiment, the Mx3005P gain setting was ×8, and measurements were performed every 120 seconds for 255 cycles. The results are shown in FIG. 6. The concentration of the FAM-DABCYL modification molecular beacon was 60 nM. In FIG. 6, the results in the three PCR tubes are shown as C1(23)-1, C1(23)-2, and C1(23)-2. As obvious from FIG. 6, in also the case of using C1(23) as the sequence conversion DNA, the fluorescence intensity increased, and it was revealed that the target nucleic acid functions as a primer to sufficiently rapidly amplify the oligonucleotide as an amplification product to a detectable level. It was therefore revealed that use of C1(23) can detect whether the target nucleic acid of SEQ ID NO: 1 exists in a sample. In addition, the results obtained in the three PCR tubes were substantially the same to show good reproducibility.

Example 5

Detection of Target Nucleic Acid Using Sequence Conversion DNA

An experiment was performed as in Example 4 except that the oligonucleotide represented by SEQ ID NO: 1 and C2(22) represented by SEQ ID NO: 11 were respectively used as a target nucleic acid and a sequence conversion DNA for detecting the target nucleic acid of SEQ ID NO: 1, and the same procedure was performed using only a buffer as a control. The results are shown in FIG. 7. As shown in FIG. 7, also in the case of using C2(22) as a sequence conversion DNA, the results in three PCR tubes were substantially the same to show good reproducibility.

Example 6

Detection of Target Nucleic Acid Using Sequence Conversion DNA

An experiment was performed as in Example 4 except that the oligonucleotide represented by SEQ ID NO: 4 and C3(23) (SEQ ID NO: 23) having the following sequence were respectively used as a target nucleic acid and a sequence conversion DNA for detecting the target nucleic acid of SEQ ID NO: 4, and the same procedure was performed using only a buffer as a control. The results are shown in FIG. 8. As shown in FIG. 8, also in the case of using C3(23) as a sequence conversion DNA, the results in three PCR tubes were substantially the same to show good reproducibility.

Example 7

Detection of Target Nucleic Acid Using Sequence Conversion DNA

Next, an experiment was performed as in Example 1 except that the concentrations of the target nucleic acid were 10 nM and 0 nM and that the concentration of the sequence conversion DNA was 10 nM, and the same procedure was performed using only a buffer as a control. As the sequence conversion DNA used to detect the target nucleic acid of SEQ ID NO: 7, C1(23) represented by SEQ ID NO: 22 was used.

In this experiment, the Mx3005P gain setting was ×1, and measurements were performed every 60 seconds for 255 cycles. The results are shown in FIG. 9. The concentration of the FAM-DABCYL modification molecular beacon was set at 100 nM. As obvious from FIG. 9, in also the case of using C1(23) as the sequence conversion DNA, the fluorescence intensity increased, and it was revealed that the target nucleic acid functioned as a primer to sufficiently rapidly amplify the oligonucleotide as an amplification product to a detectable level. Moreover, it was demonstrated that when a sequence conversion DNA is not present, the amplification reaction does not occur even if the target nucleic acid exists.

Example 8

Detection of Target Nucleic Acid Using Sequence Conversion DNA

An experiment was performed as in Example 7 except that the oligonucleotide represented by SEQ ID NO: 1 and C2(22) represented by SEQ ID NO: 11 were respectively used as a target nucleic acid and a sequence conversion DNA for detecting the target nucleic acid of SEQ ID NO: 1, and the same procedure was performed using only a buffer as a control. The results are shown in FIG. 10. As shown in FIG. 10, also in the case of using C2(22) as a sequence conversion DNA, the fluorescence intensity increased, and it was revealed that the target nucleic acid functioned as a primer to sufficiently rapidly amplify the oligonucleotide as an amplification product to a detectable level. Moreover, it was demonstrated that when a sequence conversion DNA is not present, the amplification reaction does not occur even if the target nucleic acid exists.

Example 9

Detection of a Target Nucleic Acid Using Sequence Conversion DNA

An experiment was performed as in Example 7 except that the oligonucleotide represented by SEQ ID NO: 4 and C3(23) represented by SEQ ID NO: 23 were respectively used as a target nucleic acid and a sequence conversion DNA for detecting the target nucleic acid of SEQ ID NO: 4, and the same procedure was performed using only a buffer

```
                                                      (SEQ ID NO: 23)
TCAACATCAGTCTGATAAGCTACAGAGATCCTGATAGCCCTGTACAATGCTGCT-(TAMRA)
``` as a control. The results are shown in FIG. 11. As shown in FIG. 11, also in the case of using C3(22) as a sequence conversion DNA, the fluorescence intensity increased, and it was revealed that the target nucleic acid functioned as a primer to sufficiently rapidly amplify the oligonucleotide as an amplification product to a detectable level. Moreover, it was demonstrated that when a sequence conversion DNA is not present, the amplification reaction does not occur even if the target nucleic acid exists.

Example 10

Detection of Target Nucleic Acid Using Sequence Conversion DNA

An experiment was performed as in Example 7 except that the oligonucleotide represented by SEQ ID NO: 1 and C2(15) represented by SEQ ID NO: 17 were respectively used as a target nucleic acid and a sequence conversion DNA for detecting the target nucleic acid of SEQ ID NO: 1, and the same procedure was performed using only a buffer as a control. The results are shown in FIG. 12. As shown in FIG. 12, also in the case of using C2(15) as a sequence conversion DNA, the fluorescence intensity increased, and it was revealed that the target nucleic acid functioned as a primer to sufficiently rapidly amplify the oligonucleotide as an amplification product to a detectable level. Moreover, it was demonstrated that when a sequence conversion DNA is not present, the amplification reaction does not occur even if the target nucleic acid exists.

Example 11

Detection of a Target Nucleic Acid Using Sequence Conversion DNA

An experiment was performed as in Example 7 except that the oligonucleotide represented by SEQ ID NO: 4 and C3(19) represented by SEQ ID NO: 12 were respectively used as a target nucleic acid and a sequence conversion DNA for detecting the target nucleic acid of SEQ ID NO: 4, and the same procedure was performed using only a buffer as a control. The results are shown in FIG. 13. As shown in FIG. 13, also in the case of using C3(19) as a sequence conversion DNA, the fluorescence intensity increased, and it was revealed that the target nucleic acid functioned as a primer to sufficiently rapidly amplify the oligonucleotide as an amplification product to a detectable level. Moreover, it was demonstrated that when a sequence conversion DNA is not present, the amplification reaction does not occur even if the target nucleic acid exists.

Example 12

Detection of Target Nucleic Acid Using Sequence Conversion DNA

An experiment was performed as in Example 1 except that the oligonucleotide represented by SEQ ID NO: 1 was used at concentrations of 100 nM, 10 nM, and 0 nM as the target nucleic acid, that C2(22) represented by SEQ ID NO: 11 was used at a concentration of 100 nM as the sequence conversion DNA for detecting the target nucleic acid of SEQ ID NO: 1, that 0.05 units/µL of a Klenow fragment (a variant lacking 3'→5' exonuclease activity) of DNA polymerase I was used as the DNA polymerase, and that the results were measured every 60 seconds, and the same procedure was performed using only a buffer as a control. The results are shown in FIG. 14. As shown in FIG. 14, it was demonstrated that in the system not containing the target nucleic acid and the system of only the buffer, the amplification reaction did not occur. It was revealed that when a target nucleic acid is present, the target nucleic acid functioned as a primer to sufficiently rapidly amplify the oligonucleotide as an amplification product to a detectable level. The greater volume of the target nucleic acid, the more quickly the amplification product was detected.

The concentration of the FAM-DABCYL modification molecular beacon for detecting an amplification product was 100 nM in Example 12 and was 60 nM in Examples 13 to 18, and the Mx3005P gain stetting was ×8 in Examples 12 to 18.

Example 13

Detection of Target Nucleic Acid Using Sequence Conversion DNA

An experiment was performed as in Example 12 except that the oligonucleotide represented by SEQ ID NO: 7 was used at concentrations of 0 nM and 30 nM as the target nucleic acid and that C1(23) represented by SEQ ID NO: was used at a concentration of 30 nM as the sequence conversion DNA for detecting the target nucleic acid of SEQ ID NO: 7. As a control, the same procedure was performed using only a buffer. The results are shown in FIG. 15. As shown in FIG. 15, it was demonstrated that in the system not containing the target nucleic acid and the system of only the buffer, the amplification reaction did not occur. It was revealed that in a system containing a target nucleic acid, the target nucleic acid functions as a primer to sufficiently rapidly amplify the oligonucleotide as an amplification product to a detectable level.

Example 14

Detection of Target Nucleic Acid Using Sequence Conversion DNA

An experiment was performed as in Example 13 except that the oligonucleotide represented by SEQ ID NO: 1 was used at concentrations of 0 nM and 30 nM as the target nucleic acid and that C2(22) represented by SEQ ID NO: 11 was used as the sequence conversion DNA for detecting the target nucleic acid of SEQ ID NO: 1. As a control, the same procedure was performed using only a buffer. The results are shown in FIG. 16. As shown in FIG. 16, it was demonstrated that in the system not containing the target nucleic acid and the system of only a buffer, the amplification reaction did not occur. It was revealed that in a system containing a target nucleic acid, the target nucleic acid functions as a primer to sufficiently rapidly amplify the oligonucleotide as an amplification product to a detectable level.

Example 15

Detection of Target Nucleic Acid Using Sequence Conversion DNA

An experiment was performed as in Example 13 except that the oligonucleotide represented by SEQ ID NO: 4 was used at concentrations of 0 nM and 30 nM as the target nucleic acid and that C3(23) represented by SEQ ID NO: 23 was used as the sequence conversion DNA for detecting the target nucleic acid of SEQ ID NO: 4. As a control, the same procedure was performed using only a buffer. The results are shown in FIG. 17. As shown in FIG. 17, it was demonstrated that in the system not containing a target nucleic acid and in the system of only a buffer, the amplification reaction did not occur. It was revealed that in a system containing a target nucleic acid, the target nucleic acid functions as a primer to sufficiently rapidly amplify the oligonucleotide as an amplification product to a detectable level.

Example 16

Detection of Target Nucleic Acid Using Sequence Conversion DNA

An experiment was performed as in Example 13 except that C1(15) represented by SEQ ID NO: 13 was used as the sequence conversion DNA for detecting the target nucleic acid of SEQ ID NO: 7. As a control, the same procedure was performed using only a buffer. The results are shown in FIG. 18. As shown in FIG. 18, it was demonstrated that in the system not containing a target nucleic acid and in the system of only a buffer, the amplification reaction did not occur. It was revealed that in a system containing a target nucleic acid, the target nucleic acid functions as a primer to sufficiently rapidly amplify the oligonucleotide as an amplification product to a detectable level.

Example 17

Detection of Target Nucleic Acid Using Sequence Conversion DNA

An experiment was performed as in Example 13 except that the oligonucleotide represented by SEQ ID NO: 1 and C2(15) represented by SEQ ID NO: 17 were respectively used as a target nucleic acid and a sequence conversion DNA for detecting the target nucleic acid of SEQ ID NO: 1. As a control, the same procedure was performed using only a buffer. The results are shown in FIG. 19. As shown in FIG. 19, it was demonstrated that in the system not containing the target nucleic acid and the system of only a buffer, the amplification reaction did not occur. It was revealed that in a system containing a target nucleic acid, the target nucleic acid functions as a primer to sufficiently rapidly amplify the oligonucleotide as an amplification product to a detectable level.

Example 18

Detection of Target Nucleic Acid Using Sequence Conversion DNA

An experiment was performed as in Example 13 except that the oligonucleotide represented by SEQ ID NO: 4 and C3(19) represented by SEQ ID NO: 17 were respectively used as a target nucleic acid and a sequence conversion DNA for detecting the target nucleic acid of SEQ ID NO: 4. As a control, the same procedure was performed using only a buffer. The results are shown in FIG. 20. As shown in FIG. 20, it was demonstrated that in the system not containing the target nucleic acid and the system of only a buffer, the amplification reaction did not occur. It was revealed that in a system containing a target nucleic acid, the target nucleic acid functions as a primer to sufficiently rapidly amplify the oligonucleotide as an amplification product to a detectable level.

Example 19

Detection of Target Nucleic Acid Using Sequence Conversion DNA and Signal Amplification DNA A procedure was performed as in Example 1 except that 100 nM of C2(22) as a sequence conversion DNA and 100 nM of A2(23) having the following sequence as a signal amplification DNA were used or that only C2(22) was used. In this experiment, 10 nM of the nucleic acid represented by SEQ ID NO: 1 was used as a target nucleic acid. As a control, the same procedure was performed using only a buffer. Measurements were performed every 60 seconds for 255 cycles.

Sequence of A2(23):

(SEQ ID NO: 20)
TGATAGCCCTGTACAATGCTGCT<u>CAGAGATCC</u>TGATAGCCCTGTACAATGCTGCT-(TAMRA)

A2(23) represented by SEQ ID NO: 20 contains <u>GATCC</u>, which is a nicking endonuclease Nt.AlwI recognition site, and the 3' end side of the sequence GGATCTCTG, which is the complementary sequence to CAGAGATCC, is cleaved by Nt.AlwI.

The results are shown in FIG. 21.

In FIG. 21, C2(22) & A2(23)_10 nm shows a system containing a sequence conversion DNA and a signal amplification DNA, and C2(22)_10 nM is a system containing a sequence conversion DNA, but not containing any signal amplification DNA. As obvious from FIG. 21, in both the systems containing and not containing the signal amplification DNA, the fluorescence intensity increased, but the system containing the signal amplification DNA was confirmed to be quick in the increase of the fluorescence intensity and to be high in the increase rate. Thus, it was demonstrated that in the case of a low content, 10 nM, of a target nucleic acid to be detected under such a reaction condition, a system containing a signal amplification DNA has higher detection sensitivity than a system not containing any signal amplification DNA.

Example 20

Detection of Target Nucleic Acid Using Sequence Conversion DNA and Signal Amplification DNA A procedure was performed as in Example 19 except that the concentration of the target nucleic acid was 1 nM. As a control, the same procedure was performed using only a buffer. The results are shown in FIG. 22.

As obvious from FIG. 22, in the system not containing any signal amplification DNA, the fluorescence intensity hardly increased. Thus, this system cannot detect a target nucleic acid having a low concentration of 1 nM under such a reaction condition. It was revealed that in the system containing a signal amplification DNA, the signal DNA functions as a primer, and the nucleic acid amplification reaction exponentially progressed to allow confirmation of an increase in fluorescence intensity. Thus, it was revealed that a nucleic acid having a low concentration of 1 nM can be detected by a system containing both a sequence conversion DNA and a signal amplification DNA.

Example 21

Detection of Target Nucleic Acid Using Sequence Conversion DNA and Signal Amplification DNA A procedure was performed as in Example 19 except that the oligonucleotide represented by SEQ ID NO: 7 was used as a target nucleic acid, 100 nM of C1(10) was used as a sequence conversion DNA for detecting the target nucleic acid of SEQ ID NO: 7, and 100 nM of A1 (15) having the following sequence below was used as a signal amplification DNA and that the amount of Large Fragment of Bst DNA polymerase was 0.016 units/μL. In this experiment, 10 nM of the nucleic acid represented by SEQ ID NO: 7 was used. As a control, the same procedure was performed using only a buffer. Measurements were performed every 60 seconds for 255 cycles. The results are shown in FIG. 23.

Sequence of A1 (15):

(SEQ ID NO: 21)
CTGTTCCTGCTGAACTGAGCCACAGAGATCCCTGTTCCTGCTGAAC- (TAMRA)

A1(15) represented by SEQ ID NO: 21 contains GATCC, which is a nicking endonuclease Nt.Alwl recognition site, and the 3' end side of the sequence GGATCTCTG, which is the complementary sequence to CAGAGATCC, is cleaved by Nt.Alwl.

As obvious from FIG. 23, an increase in fluorescence intensity was observed in both the system containing the signal amplification DNA and the system not containing the signal amplification DNA, but the fluorescence intensity in the system containing the signal amplification DNA reached near the upper limit earlier than the system not containing the signal amplification DNA (when a signal DNA acts on the same quantity of a molecular beacon, the fluorescence intensity is saturated and does not increase even if the amplification of the signal DNA excessively progresses). Thus, it was revealed that in the case of a low concentration, 10 nM, of a target nucleic acid to be detected, a system containing both a sequence conversion DNA and a signal amplification DNA can detect a target nucleic acid more quickly and with greater sensitivity.

Example 22

Detection of Target Nucleic Acid Using Sequence Conversion DNA and Signal Amplification DNA A procedure was performed as in Example 21 except that C1(12) was used as a sequence conversion DNA. As a control, the same procedure was performed using only a buffer. The results are shown in FIG. 24.

As obvious from FIG. 24, an increase in fluorescence intensity was observed in both the system containing the signal amplification DNA and system not containing the signal amplification DNA, but the fluorescence intensity in the system containing the signal amplification DNA reached near the upper limit earlier than the system not containing the signal amplification DNA (when a signal DNA acts on the same quantity of a molecular beacon, the fluorescence intensity is saturated and does not increase even if the amplification of the signal DNA excessively progresses). Thus, it was revealed that in the case of a low concentration, 10 nM, of a target nucleic acid to be detected, a system containing both a sequence conversion DNA and a signal amplification DNA can detect a target nucleic acid more quickly and with greater sensitivity.

Example 23

Detection of Target Nucleic Acid Using Sequence Conversion DNA and Signal Amplification DNA A procedure was performed as in Example 21 except that C1(15) was used as the sequence conversion DNA for detecting the target nucleic acid of SEQ ID NO 7. As a control, the same procedure was performed using only a buffer. The results are shown in FIG. 25.

As obvious from FIG. 25, an increase in fluorescence intensity was observed in both the system containing the signal amplification DNA and the system not containing the signal amplification DNA, but the fluorescence intensity in the system containing the signal amplification DNA reached near the upper limit earlier than the system not containing the signal amplification DNA (when a signal DNA acts on the same quantity of a molecular beacon, the fluorescence intensity is saturated and does not increase even if the amplification of the signal DNA excessively progresses). Thus, it was revealed that in the case of a low concentration, 10 nM, of a target nucleic acid to be detected, a system containing both a sequence conversion DNA and a signal amplification DNA can detect a target nucleic acid more quickly and with greater sensitivity.

Example 24

Detection of Target Nucleic Acid Using Sequence Conversion DNA and Signal Amplification DNA A procedure was performed as in Example 19 except that the oligonucleotide represented by SEQ ID NO: 1, 10 nM of C2(22), and 30 nM of A2(23) were respectively used as a target nucleic acid, a sequence conversion DNA for detecting the target nucleic acid of SEQ ID NO: 1, and a signal amplification DNA or that A2(23) was not used. In this experiment, 10 nM of the nucleic acid represented by SEQ ID NO: 1 was used as the target nucleic acid. As a control, the same procedure was performed using only a buffer. In the experiment, the Mx3005P gain setting was ×8, and measurements were performed every 60 seconds for 255 cycles. The results are shown in FIG. 26.

As obvious from FIG. 26, an increase in fluorescence intensity was observed in both the system containing the signal amplification DNA and the system not containing the signal amplification DNA, but the fluorescence intensity in the system containing the signal amplification DNA reached near the upper limit earlier than the system not containing the signal amplification DNA (when a signal DNA acts on the same quantity of a molecular beacon, the fluorescence intensity is saturated and does not increase even if the amplification of the signal DNA excessively progresses). Thus, it was revealed that in the case of a low concentration, 10 nM, of a target nucleic acid to be detected, a system containing both a sequence conversion DNA and a signal amplification DNA can detect a target nucleic acid more quickly and with greater sensitivity.

Example 25

Detection of Target Nucleic Acid Using Sequence Conversion DNA and Signal Amplification DNA A procedure was performed as in Example 19 except that the oligonucleotide represented by SEQ ID NO: 1, 10 nM of C2(22), and 30 nM of A2(23) were respectively used as a target nucleic acid, a sequence conversion DNA for detecting the target nucleic acid of SEQ ID NO: 1, and a signal amplification DNA. This experiment was carried out using 0 nM, 0.1 nM, and 1 nM of the nucleic acid represented by SEQ ID NO: 1 as a target nucleic acid. In this experiment, the Mx3005P gain setting was ×8, and measurements were performed every 60 seconds for 255 cycles. The results are shown in FIG. 27.

As obvious from FIG. 27, it was revealed that the stage at which an increase in fluorescence intensity is confirmed becomes earlier with an increase of the amount of the target nucleic acid.

Example 26

A procedure was performed as in Example 19 except that the oligonucleotide represented by SEQ ID NO: 1 was used as a target nucleic acid, the concentration of the FAM-DABCYL modification molecular beacon for detecting the amplification product was 60 nM (hereinafter the same applies in the following Examples), 10 nM of C2(22) was used as a sequence conversion DNA for detecting the target nucleic acid of SEQ ID NO: 1, and 30 nM of A2(23) was used as a signal amplification DNA or that A2(23) was not used. In this experiment, the oligonucleotide represented by SEQ ID NO: 1 was used at concentrations of 0 nM, 1 nM, and 10 nM as the target nucleic acid. The DNA polymerase used was 0.08 units/µL of Large Fragment of Bst DNA polymerase, and the nicking endonuclease used was 0.1 units/µL of Nt.Alwl. As a control, the same procedure was performed using only a buffer. In this experiment, the Mx3005P gain setting was ×8, and measurements were performed every 60 seconds for 255 cycles. The results are shown in FIG. 28. As obvious from FIG. 28, the fluorescence intensity did not increase in the case of using only the buffer. The fluorescence intensity increased when the concentration of the target nucleic acid was 10 nM, but reached near the upper limit in the system containing the signal amplification DNA earlier than the system not containing the signal amplification DNA. When the concentration of the target nucleic acid was 1 nM, the fluorescence intensity increased in the systems containing the signal amplification DNA, but hardly increased in the system not containing the signal amplification DNA. Thus, it was revealed that in the case of containing a signal DNA, even if the concentration of a target nucleic acid to be detected is low, it is possible to detect the target nucleic acid with greater sensitivity.

Example 27

A procedure was performed as in Example 19 except that the oligonucleotide represented by SEQ ID NO: 1 was used as a target nucleic acid, 10 nM of C2(22) was used as a sequence conversion DNA for detecting the target nucleic acid of SEQ ID NO: 1, and 10 nM of A2(23) was used as a signal amplification DNA. The DNA polymerase used was 0.05 units/µL of a Klenow fragment (a variant lacking 3'→5' exonuclease activity) of DNA polymerase I. The target nucleic acid was 0 nM, 10 nM, and 100 nM oligonucleotide represented by SEQ ID NO: 1. As a control, the same procedure was performed using only a buffer. In this experiment, the Mx3005P gain setting was ×8, and measurements were performed every 60 seconds for 150 cycles. The results are shown in FIG. 29.

As obvious from FIG. 29, the fluorescence intensity did not increase when the target nucleic acid was not present, but increased when the target nucleic acid was present, and the fluorescent intensity reached near the upper limit earlier when the concentration of the target nucleic acid was larger.

Example 28

A procedure was performed as in Example 19 except that the oligonucleotide (RNA) represented by SEQ ID NO: 24 was used as a target nucleic acid, 10 nM of C2(22) was used as a sequence conversion DNA for detecting the target nucleic acid of SEQ ID NO: 24, and 10 nM of A2(23) was used as a signal amplification DNA. The DNA polymerase used was 0.05 units/µL of a Klenow fragment (a variant lacking 3'→5' exonuclease activity) of DNA polymerase I. The target nucleic acid was 0 nM and 10 nM oligonucleotide represented by SEQ ID NO: 24. As a control, the same procedure was performed using only a buffer. In this experiment, the Mx3005P gain setting was ×8, and measurements were performed every 60 seconds for 255 cycles. The results are shown in FIG. 30.

As obvious from FIG. 30, the fluorescence intensity hardly increased when the RNA as the target nucleic acid was not present, but increased when the RNA as the target nucleic acid was present.

```
                                              (SEQ ID NO: 24)
          UGGCUCAGUUCAGCAGGAACAG
```

Example 29

A procedure was performed as in Example 19 using the oligonucleotide represented by SEQ ID NO: 4 as a target nucleic acid, 10 nM of C3(23) represented by SEQ ID NO: 23 as a sequence conversion DNA for detecting the target nucleic acid in SEQ ID NO: 23, and 10 nM of A3(19) represented by SEQ ID NO: 25 as a signal amplification DNA. The DNA polymerase used was 0.05 units/µL of a Klenow fragment (a variant lacking 3'→5' exonuclease activity) of DNA polymerase I. The concentrations of the nucleic acid represented by SEQ ID NO: 4 as the target nucleic acid were 0 nM and 10 nM. As a control, the same procedure was performed using only a buffer. In this experiment, the concentration of the FAM-DABCYL modification molecular beacon for detecting the amplification product was 60 nM, the Mx3005P gain setting was ×8, and measurements were performed every 60 seconds for 255 cycles. The results are shown in FIG. 31.

As shown in FIG. 31, it was revealed that the fluorescence intensity did not increase when the target nucleic acid was not present, but increased when the target nucleic acid was present.

Sequence of A3(19):

```
                                              (SEQ ID NO: 25)
  TCAACATCAGTCTGATAAGCTACAGAGATCCTCAACATCAGTCTGATAA
  G-(TAMRA).
```

A3(19) contains GATCC, which is a nicking endonuclease Nt.Alwl recognition site, and the 3' end side of the sequence GGATCTCTG, which is the complementary sequence to CAGAGATCC, is cleaved by the Nt.Alwl.

Example 30

A procedure was performed as in Example 19 using the oligonucleotide represented by SEQ ID NO: 7 as a target nucleic acid, 10 nM of C1 (10) as a sequence conversion DNA for detecting the target nucleic acid of SEQ ID NO: 7, and 30 nM of A1 (22) (SEQ ID NO: 26) having the following sequence as a signal amplification DNA. The procedure was performed using 0.08 units/µL of Large Fragment of Bst DNA polymerase as a DNA polymerase and 0.1 units/µL of Nt.Alwl. In this experiment, the concentrations of the nucleic acid represented by SEQ ID NO: 7 as the target nucleic acid were 0 nM and 10 nM for the target nucleic acid. As a control, the same procedure was performed using only a buffer. In this experiment, the Mx3005P gain setting was ×8, and measurements were performed every 60 seconds for 255 cycles. The results are shown in FIG. 32.

As shown in FIG. 32, the fluorescence intensity did not increase when the target nucleic acid was not present. In addition, in the system containing a signal amplification DNA, but not containing any signal amplification DNA, fluorescence intensity hardly increased even when the target nucleic acid was present. In contrast, in the system containing a sequence conversion DNA and a signal amplification DNA, the fluorescence intensity increased.

Sequence of A1 (22):

(SEQ ID NO: 26)
CTGTTCCTGCTGAACTGAGCCA<u>CAGAGATCCC</u>TGTTCCTGCTGAACTGAGCCA-(TAMRA)

A1 (22) contains <u>GATCC</u>, which is a nicking endonuclease Nt.Alwl recognition site, and the 3' end side of the sequence GGATCTCTG, which is the complementary sequence to CAGAGATCC, is cleaved by the Nt.Alwl.

Example 31

A procedure was performed as in Example 19 using the oligonucleotide represented by SEQ ID NO: 7 as a target nucleic acid, 10 nM of C1 (15) as a sequence conversion DNA for detecting the target nucleic acid of SEQ ID NO: 7, and 10 nM of A1(22) (SEQ ID NO: 26) represented by SEQ ID NO: 26 or not using A1(22). The procedure was performed using 0.08 units/μL of Large Fragment of Bst DNA polymerase as a DNA polymerase and 0.1 units/μL of Nt.Alwl. In this experiment, the concentrations of the nucleic acid represented by SEQ ID NO: 7 as the target nucleic acid were 0 nM and 10 nM. As a control, the same procedure was performed using only a buffer. In this experiment, the Mx3005P gain setting was ×8, and measurements were performed every 60 seconds for 255 cycles. The results are shown in FIG. 33.

As shown in FIG. 33, the fluorescence intensity hardly increased when the target nucleic acid was not present. In addition, in the system containing a signal amplification DNA, but not containing any signal amplification DNA, the fluorescence intensity hardly increased even when the target nucleic acid was present. In contrast, in the system containing a sequence conversion DNA and a signal amplification DNA, the fluorescence intensity increased.

Example 32

This Example investigates whether two types of target nucleic acids can be simultaneously detected.

The oligonucleotide represented by SEQ ID NO: 7, 30 nM of C1 (23), and 30 nM of A1 (22) were respectively used as a target nucleic acid, a sequence conversion DNA for detecting the target nucleic acid of SEQ ID NO: 7, and a signal amplification DNA. Additionally, the oligonucleotide represented by SEQ ID NO: 4, 30 nM of C3(23), and 30 nM of A3(19) were respectively used as a target nucleic acid, a sequence conversion DNA for detecting the target nucleic acid of SEQ ID NO: 4, and a signal amplification DNA. A procedure was performed as in Example 19 using 0.08 units/μL of Large Fragment of Bst DNA polymerase units as a DNA polymerase and 0.1 units/μL of Nt.Alwl. In this experiment, the concentrations of the nucleic acids represented by SEQ ID NO: 7 and SEQ ID NO: 4 as the target nucleic acids were each 0 nM and 30 nM. As a control, the same procedure was performed using only a buffer. In addition, experiments were also carried out for a case of containing only the oligonucleotide represented by SEQ ID NO: 7 and a case of containing only the oligonucleotide represented by SEQ ID NO: 4. In the experiments, the Mx3005P gain setting was ×4, and measurements were performed every 60 seconds for 255 cycles. The results are shown in FIG. 34.

As shown in FIG. 34, the fluorescence intensity did not increase when the target nucleic acid was not present and when only the buffer was used. In the case of using only the oligonucleotide represented by SEQ ID NO: 7 as the target nucleic acid, the fluorescence intensity increased by using C1(23) as the sequence conversion DNA and A1 (22) as the signal amplification DNA. In the case of using only the oligonucleotide represented by SEQ ID NO: 4 as the target nucleic acid, the fluorescence intensity increased by using C3(23) as the sequence conversion DNA and A3(19) as the signal amplification DNA. In the case of including both the oligonucleotide represented by SEQ ID NO: 4 and the oligonucleotide represented by SEQ ID NO: 7, it was observed that the fluorescence intensity increases with the number of cycles, demonstrating that two types of nucleic acids can be simultaneously detected even when the both are present.

Example 33

A procedure was performed as in Example 19 using the oligonucleotide represented by SEQ ID NO: 1 as a target nucleic acid, 10 nM of C2(22) as a sequence conversion DNA for detecting the target nucleic acid of SEQ ID NO: 1, and 30 nM of A2(23) as a signal amplification DNA. The procedure was performed using 0.08 units/μL of Large Fragment of Bst DNA polymerase as a DNA polymerase and 0.1 units/μL of Nt.Alwl. The concentrations of the nucleic acid represented by SEQ ID NO: 1 were 0 nM, 2 nM, 4 nM, 6 nM, 8 nM, and 10 nM as the target nucleic acid. As a control, the same procedure was performed using only a buffer. In this experiment, the Mx3005P gain setting was ×8, and measurements were performed every 60 seconds for 60 cycles. The results are shown in FIG. 35.

As shown in FIG. 35, the fluorescence intensity did not increase when a target nucleic acid was not present and when only a buffer was used. Moreover, the fluorescence intensity increased with the concentration of the target nucleic acid.

In the results of FIG. 35, a calibration curve was formed by plotting the number of cycles when the fluorescence intensity level reaches 10000 on the vertical axis and the concentrations of the target nucleic acid on the horizontal axis. The results are shown in FIG. 36. As shown in FIG. 36, it was revealed that there is a certain relationship between the fluorescence intensity and the concentration of the target nucleic acid and that the concentration of the target nucleic acid in a sample can be quantitatively measured using this calibration curve.

Example 34

A procedure was performed as in Example 32 using the oligonucleotide represented by SEQ ID NO: 1 as a target nucleic acid, 10 nM of C2(22) as a sequence conversion DNA for detecting the target nucleic acid of SEQ ID NO: 1, and 30 nM of A2(23) as a signal amplification DNA. The concentrations of the nucleic acid represented of SEQ ID NO: 1 as the target nucleic acid were 0 nM, 2 nM, and 10 nM. The same experiment was performed using 10 nM of the oligonucleotide represented by SEQ ID NO: 7 as an additional nucleic acid. In this experiment, the Mx3005P gain setting was ×8, and measurements were performed every 60 seconds for 50 cycles. The results are shown in FIG. 37.

As shown in FIG. 37, the fluorescence intensity did not increase when only a buffer was used and when both the target nucleic acid and the oligonucleotide represented by SEQ ID NO: 7 were not present. The fluorescence intensity increased with the concentration of the target nucleic acid as shown in the cases where the concentrations were 2 nM and 10 nM. This fluorescence intensity did not substantially change even when the oligonucleotide represented by SEQ ID NO: 7 was present together. These results demonstrate that even if nucleic acids other than the target nucleic acid are present in the system, the presence does not affect the measurement results.

Example 35

Detection of Target Nucleic Acid Using Sequence Conversion DNA

The oligonucleotide represented by SEQ ID NO: 29 was used as a target nucleic acid, 10 nM of Bbv_C2(12) represented by SEQ ID NO: 27 was used as a sequence conversion DNA for detecting the target nucleic acid of SEQ ID NO: 29. The concentrations of the target nucleic acid represented by SEQ ID NO: 29 as the target nucleic acid were 0 nM and 10 nM. The nicking endonuclease used was 0.1 units/µL of Nb.BbvCl. The same procedure was performed using only a buffer as a control. In this experiment, the Mx3005P gain setting was ×8, and measurements were performed every 60 seconds for 255 cycles. The results are shown in FIG. 38.

Bbv_C2(12) includes CCTCAGC, which is an Nb.BbvCl recognition site, and Nb.BbvCl cleaves between GC and TGAGG of CGTGAGG, which is the sequence complementary to CCTCAGC.

(SEQ ID NO: 27)
TGATAGCCCTGTACAATGCTGCTCCTCAGCCACACGATCCT-(TAMRA)

As obvious from FIG. 38, the fluorescence intensity did not increase when only a buffer was used and when the target nucleic acid was not present, but the fluorescence intensity increased when the target nucleic acid was present.

SEQ ID NO: 29
(TAGCTTATCAGACTGATGTTGA)

Example 36

Detection of Target Nucleic Acid Using Sequence Conversion DNA and Signal Amplification DNA The oligonucleotide represented by SEQ ID NO: 29 was used as a target nucleic acid, 10 nM of Bbv_C2(12) was used as a sequence conversion DNA for detecting the target nucleic acid of SEQ ID NO: 29, and 30 nM of Bbv_A2(22) represented by SEQ ID NO: 28 was used as a signal amplification DNA. The concentrations of the nucleic acid represented by SEQ ID NO: 29 as the target nucleic acid were 0 nM, 1 nM, and 10 nM. The nicking endonuclease used was 0.1 units/µL of Nb.BbvCl. The same procedure was performed using only a buffer as a control. In this experiment, the Mx3005P gain setting was ×8, and measurements were performed every 60 seconds for 120 cycles. The results are shown in FIG. 39.

Bbv_C2(12) and Bbv_A2(22) both comprise CCTCAGC, which is an Nb.BbvCl recognition site, and Nb.BbvCl cleaves between GC and TGAGG of GCTGAGG, which is the sequence complementary to CCTCAGC.

(SEQ ID NO: 28)
TGATAGCCCTGTACAATGCTGCTCCTCAGCTGATAGCCCTGTACAATGCTGCT-(TAMRA)

As obvious from FIG. 40, the fluorescence intensity did not increase when only a buffer was used and when the target nucleic acid was not present, but the fluorescence intensity increased when the target nucleic acid was present. The higher the target nucleic acid concentration, the faster the fluorescence intensity increased.

As was described in detail above, it has been shown that the method for detecting a target nucleic acid of the present invention can specifically detect a target nucleic acid with high sensitivity and can specifically detect a target nucleic acid, even if the nucleic acid is a short-chain nucleic acid, with high sensitivity.

The invention claimed is:

1. A method for detecting a target nucleic acid in a sample, the method comprising:
   (a) preparing a first oligonucleotide comprising, in a direction from 5' to 3', (i) a first arbitrary sequence having about 5 to about 50 nucleotides, (ii) an endonuclease recognition site that is used in a nicking reaction, and (iii) a sequence complementary to the 3' end of the target nucleic acid; and a second oligonucleotide comprising, in a direction from 5' to 3', (i) a second arbitrary sequence having about 5 to about 50 nucleotides and a sequence substantially homologous to the first arbitrary sequence, (ii) an endonuclease recognition site that is used in a nicking reaction, and (iii) a sequence substantially homologous to the first arbitrary sequence;
   (b) preparing a reaction mixture comprising the sample, the first oligonucleotide, the second oligonucleotide, a polymerase, and an endonuclease;
   (c) maintaining the reaction mixture at a temperature of about 35° C. to about 37° C. under conditions wherein the 3' end of a target nucleic acid binds to the sequence of the first oligonucleotide complementary to the 3' end of the target nucleic acid and primes replication to produce an extended target nucleic acid which is nicked by the endonuclease to produce a nick which further primes replication to produce a signal DNA complementary to the second arbitrary sequence of the second oligonucleotide; and
   wherein said signal DNA binds to the second oligonucleotide at the 3' end sequence substantially homologous to the first arbitrary sequence and primes replication to produce an extended signal DNA which is nicked by the endonuclease to produce a nick which further primes replication to produce additional signal DNA;
   (d) detecting the signal DNA, wherein the presence of the signal DNA detects the target nucleic acid.

2. The method according to claim 1 further comprising:
   (e) performing a nucleic acid amplification reaction in the presence of the target nucleic acid having a known concentration, the first oligonucleotide, the second oligonucleotide, and the endonuclease and measuring an oligonucleotide obtained through the nucleic acid amplification reaction;
   (f) performing step (e) using target nucleic acid having a different known concentration and forming a calibration curve from the measurement results; and
   (g) determining the concentration of the target nucleic acid to be detected on the basis of the calibration curve.

3. The method according to claim 1 or claim 2 wherein steps c and d are performed together.

4. The method according to claim 1 or claim 2 wherein the temperature is 37° C.

5. The method according to claim 1 or claim 2 wherein the endonuclease is Nt.Alwl and the first oligonucleotide includes the sequence GATCC.

6. The method according to claim 1 or claim 2 wherein the endonuclease is Nb.BbvCl and the first oligonucleotide includes the sequence CCTCAGC.

7. The method according to claim 1 or claim 2 wherein the nucleic acid amplification reaction uses a DNA polymerase having strand displacement ability.

8. The method according to claim 7 wherein the DNA polymerase is selected from the group consisting of Klenow fragments of DNA polymerase I derived from *E. coli*, 5' to 3' exonuclease-deficient Bst DNA polymerases derived from *Bacillus stearothermophilus*, and 5' to 3' exonuclease-deficient Bca DNA polymerases derived from *Bacillus caldotenax*.

9. The method according to claim 1 or claim 2 wherein at least one of the first or second oligonucleotide has a modified 3' end.

10. A method for detecting a target nucleic acid in a sample, said method comprising combining said sample with:
   (a) a first oligonucleotide comprising, in a 5' to 3' direction, (i) a first arbitrary sequence having about 5 to about 50 nucleotides, (ii) an endonuclease recognition site, and (iii) a sequence complementary to the 3' end of said target nucleic acid;
   (b) a second oligonucleotide comprising, in a 5' to 3' direction, (i) a second arbitrary sequence having about 5 to about 50 nucleotides substantially homologous to said first arbitrary sequence, (ii) an endonuclease recognition site, and (iii) a sequence substantially homologous to the first arbitrary sequence;

(c) a polymerase; and (d) at least one endonuclease for a nicking reaction;

maintaining a temperature of about 35° C. to about 37° C. under conditions wherein the 3' end of the target nucleic acid binds to the sequence of the first oligonucleotide complementary to the 3' end of the target nucleic acid and primes replication to produce an extended target nucleic acid which is nicked by the endonuclease to produce a nick which further primes replication to produce a signal DNA complementary to the second arbitrary sequence of the second oligonucleotide; and wherein said signal DNA binds to the second oligonucleotide at the 3' end sequence substantially homologous to the first arbitrary sequence and primes replication to produce an extended signal DNA which is nicked by the endonuclease to produce a nick which further primes replication to produce additional signal DNA; and detecting the signal DNA, wherein the presence of the signal DNA detects the target nucleic acid.

11. The method according to claim 10 further comprising forming a calibration curve and determining the concentration of said target nucleic acid on the basis of the calibration curve.

12. The method according to claim 10 wherein said endonuclease is an enzyme selected from the group consisting of Nb.BbvCl, Nt.Alwl, Nt.BbvCl, and Nt.BsmAl.

13. The method according to claim 10 wherein said polymerase is a DNA polymerase having strand displacement ability.

14. The method according to claim 10 wherein said polymerase is selected from the group consisting of Klenow fragments, DNA polymerase I derived from *E. coli*, 5' to 3' exonuclease-deficient Bst DNA polymerases derived from *Bacillus stearothermophilus*, and 5' to 3' exonuclease-deficient Bca DNA polymerases derived from *Bacillus caldotenax*.

15. The method according to claim 10 wherein at least one of the first and second oligonucleotides have a modified 3' end.

16. A composition for detecting a target nucleic acid, said composition comprising:

a) a first oligonucleotide comprising, in a 5' to 3' direction, (i) a first arbitrary sequence, (ii) a nicking endonuclease recognition site, and (iii) a sequence complementary to said target nucleic acid;

(b) a second oligonucleotide comprising, in a 5' to 3' direction, (i) a second arbitrary sequence substantially homologous to said first arbitrary sequence, (ii) a nicking endonuclease recognition site, and (iii) a sequence substantially homologous to the first arbitrary sequence;

(c) a polymerase; and (d) at least one nicking endonuclease;

said composition maintained at a temperature of about 35° C.

17. The method according to claim 1 or claim 10 wherein the first arbitrary sequence comprises about 20 bases.

18. The method according to claim 17 wherein the first arbitrary sequence comprises 22 or 23 bases.

* * * * *

SEQUENCE LISTING

<160> NUMBER OF SEQ ID NOS: 29

<210> SEQ ID NO 1
<211> LENGTH: 22
<212> TYPE: DNA
<213> ORGANISM: Artificial
<220> FEATURE:
<223> OTHER INFORMATION: Synthetic DNA

```
<400> SEQUENCE: 1
tggctcagtt cagcaggaac ag                                          22

<210> SEQ ID NO 2
<211> LENGTH: 22
<212> TYPE: DNA
<213> ORGANISM: Artificial
<220> FEATURE:
<223> OTHER INFORMATION: Synthetic DNA

<400> SEQUENCE: 2
ctgttcctgc tgaactgagc ca                                          22

<210> SEQ ID NO 3
<211> LENGTH: 15
<212> TYPE: DNA
<213> ORGANISM: Artificial
<220> FEATURE:
<223> OTHER INFORMATION: Synthetic DNA

<400> SEQUENCE: 3
ctgttcctgc tgaac                                                  15

<210> SEQ ID NO 4
<211> LENGTH: 23
<212> TYPE: DNA
<213> ORGANISM: Artificial
<220> FEATURE:
<223> OTHER INFORMATION: Synthetic DNA

<400> SEQUENCE: 4
agcagcattg tacagggcta tca                                         23

<210> SEQ ID NO 5
<211> LENGTH: 19
<212> TYPE: DNA
<213> ORGANISM: Artificial
<220> FEATURE:
<223> OTHER INFORMATION: Synthetic DNA

<400> SEQUENCE: 5
tgatagccct gtacaatgc                                              19

<210> SEQ ID NO 6
<211> LENGTH: 23
<212> TYPE: DNA
<213> ORGANISM: Artificial
<220> FEATURE:
<223> OTHER INFORMATION: Synthetic DNA

<400> SEQUENCE: 6
tgatagccct gtacaatgct gct                                         23

<210> SEQ ID NO 7
<211> LENGTH: 23
<212> TYPE: DNA
<213> ORGANISM: Artificial
<220> FEATURE:
<223> OTHER INFORMATION: Synthetic DNA

<400> SEQUENCE: 7
agctacattg tctgctgggt ttc                                         23

<210> SEQ ID NO 8
```

<211> LENGTH: 12
<212> TYPE: DNA
<213> ORGANISM: Artificial
<220> FEATURE:
<223> OTHER INFORMATION: Synthetic DNA

<400> SEQUENCE: 8
gaaacccagc ag                                                            12

<210> SEQ ID NO 9
<211> LENGTH: 10
<212> TYPE: DNA
<213> ORGANISM: Artificial
<220> FEATURE:
<223> OTHER INFORMATION: Synthetic DNA

<400> SEQUENCE: 9
gaaacccagc                                                               10

<210> SEQ ID NO 10
<211> LENGTH: 23
<212> TYPE: DNA
<213> ORGANISM: Artificial
<220> FEATURE:
<223> OTHER INFORMATION: Synthetic DNA

<400> SEQUENCE: 10
gaaacccagc agacaatgta gct                                                23

<210> SEQ ID NO 11
<211> LENGTH: 54
<212> TYPE: DNA
<213> ORGANISM: Artificial
<220> FEATURE:
<223> OTHER INFORMATION: Synthetic DNA

<400> SEQUENCE: 11
tgatagccct gtacaatgct gctcagagat ccctgttcct gctgaactga gcca              54

<210> SEQ ID NO 12
<211> LENGTH: 50
<212> TYPE: DNA
<213> ORGANISM: Artificial
<220> FEATURE:
<223> OTHER INFORMATION: Synthetic DNA

<400> SEQUENCE: 12
tcaacatcag tctgataagc tacagagatc ctgatagccc tgtacaatgc                   50

<210> SEQ ID NO 13
<211> LENGTH: 46
<212> TYPE: DNA
<213> ORGANISM: Artificial
<220> FEATURE:
<223> OTHER INFORMATION: Synthetic DNA

<400> SEQUENCE: 13
ctgttcctgc tgaactgagc cacagagatc cgaaacccag cagaca                       46

<210> SEQ ID NO 14
<211> LENGTH: 33
<212> TYPE: DNA
<213> ORGANISM: Artificial
<220> FEATURE:
<223> OTHER INFORMATION: Synthetic DNA

<400> SEQUENCE: 14
cgcgatgata gccctgtaca atgctgcttc gcg                                    33

<210> SEQ ID NO 15
<211> LENGTH: 32
<212> TYPE: DNA
<213> ORGANISM: Artificial
<220> FEATURE:
<223> OTHER INFORMATION: Synthetic DNA

<400> SEQUENCE: 15
cgcgatcaac atcagtctga taagctatcg cg                                     32

<210> SEQ ID NO 16
<211> LENGTH: 32
<212> TYPE: DNA
<213> ORGANISM: Artificial
<220> FEATURE:
<223> OTHER INFORMATION: Synthetic DNA

<400> SEQUENCE: 16
cgcgactgtt cctgctgaac tgagccatcg cg                                     32

<210> SEQ ID NO 17
<211> LENGTH: 47
<212> TYPE: DNA
<213> ORGANISM: Artificial
<220> FEATURE:
<223> OTHER INFORMATION: Synthetic DNA

<400> SEQUENCE: 17
tgatagccct gtacaatgct gctcagagat ccctgttcct gctgaac                     47

<210> SEQ ID NO 18
<211> LENGTH: 43
<212> TYPE: DNA
<213> ORGANISM: Artificial
<220> FEATURE:
<223> OTHER INFORMATION: Synthetic DNA

<400> SEQUENCE: 18
ctgttcctgc tgaactgagc cacagagatc cgaaacccag cag                         43

<210> SEQ ID NO 19
<211> LENGTH: 41
<212> TYPE: DNA
<213> ORGANISM: Artificial
<220> FEATURE:
<223> OTHER INFORMATION: Synthetic DNA

<400> SEQUENCE: 19
ctgttcctgc tgaactgagc cacagagatc cgaaacccag c                           41

<210> SEQ ID NO 20
<211> LENGTH: 55
<212> TYPE: DNA
<213> ORGANISM: Artificial
<220> FEATURE:
<223> OTHER INFORMATION: Synthetic DNA

<400> SEQUENCE: 20
tgatagccct gtacaatgct gctcagagat cctgatagcc ctgtacaatg ctgct            55

<210> SEQ ID NO 21
<211> LENGTH: 46
<212> TYPE: DNA

<213> ORGANISM: Artificial
<220> FEATURE:
<223> OTHER INFORMATION: Synthetic DNA

<400> SEQUENCE: 21
ctgttcctgc tgaactgagc cacagagatc cctgttcctg ctgaac    46

<210> SEQ ID NO 22
<211> LENGTH: 54
<212> TYPE: DNA
<213> ORGANISM: Artificial
<220> FEATURE:
<223> OTHER INFORMATION: Synthetic DNA

<400> SEQUENCE: 22
ctgttcctgc tgaactgagc cacagagatc cgaaacccag cagacaatgt agct    54

<210> SEQ ID NO 23
<211> LENGTH: 54
<212> TYPE: DNA
<213> ORGANISM: Artificial
<220> FEATURE:
<223> OTHER INFORMATION: Synthesis DNA

<400> SEQUENCE: 23
tcaacatcag tctgataagc tacagagatc ctgatagccc tgtacaatgc tgct    54

<210> SEQ ID NO 24
<211> LENGTH: 22
<212> TYPE: RNA
<213> ORGANISM: Artificial
<220> FEATURE:
<223> OTHER INFORMATION: Synthetic RNA

<400> SEQUENCE: 24
uggcucaguu cagcaggaac ag    22

<210> SEQ ID NO 25
<211> LENGTH: 50
<212> TYPE: DNA
<213> ORGANISM: Artificial
<220> FEATURE:
<223> OTHER INFORMATION: Synthetic DNA

<400> SEQUENCE: 25
tcaacatcag tctgataagc tacagagatc ctcaacatca gtctgataag    50

<210> SEQ ID NO 26
<211> LENGTH: 53
<212> TYPE: DNA
<213> ORGANISM: Artificial
<220> FEATURE:
<223> OTHER INFORMATION: Synthetic DNA

<400> SEQUENCE: 26
ctgttcctgc tgaactgagc cacagagatc cctgttcctg ctgaactgag cca    53

<210> SEQ ID NO 27
<211> LENGTH: 41
<212> TYPE: DNA
<213> ORGANISM: Artificial
<220> FEATURE:
<223> OTHER INFORMATION: Synthetic DNA

<400> SEQUENCE: 27
tgatagccct gtacaatgct gctcctcagc cacacgatcc t    41

```
<210> SEQ ID NO 28
<211> LENGTH: 53
<212> TYPE: DNA
<213> ORGANISM: Artificial
<220> FEATURE:
<223> OTHER INFORMATION: Synthetic DNA

<400> SEQUENCE: 28
tgatagccct gtacaatgct gctcctcagc tgatagccct gtacaatgct gct            53

<210> SEQ ID NO 29
<211> LENGTH: 22
<212> TYPE: DNA
<213> ORGANISM: Artificial
<220> FEATURE:
<223> OTHER INFORMATION: Synthetic DNA

<400> SEQUENCE: 29
tagcttatca gactgatgtt ga                                              22
```